United States Patent
Mao et al.

(10) Patent No.: US 12,364,980 B2
(45) Date of Patent: Jul. 22, 2025

(54) NON-INVASIVE CANCER DETECTION AND ANALYSIS BY SINGLE-MOLECULE IMAGING

(71) Applicant: The Johns Hopkins University, Baltimore, MD (US)

(72) Inventors: Chih-Ping Mao, Baltimore, MD (US); Shih-Chin Wang, Baltimore, MD (US); Jie Xiao, Baltimore, MD (US); T. C. Wu, Baltimore, MD (US); Chien-Fu Hung, Timmonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 18/437,439

(22) Filed: Feb. 9, 2024

(65) Prior Publication Data

US 2024/0246076 A1 Jul. 25, 2024

Related U.S. Application Data

(63) Continuation of application No. 16/336,124, filed as application No. PCT/US2017/053354 on Sep. 26, 2017, now abandoned.

(60) Provisional application No. 62/399,545, filed on Sep. 26, 2016.

(51) Int. Cl.
| | |
|---|---|
| *B01L 3/00* | (2006.01) |
| *B01F 33/30* | (2022.01) |
| *G01N 21/552* | (2014.01) |
| *G01N 21/64* | (2006.01) |
| *G01N 33/543* | (2006.01) |
| *G01N 33/574* | (2006.01) |
| *B01F 25/431* | (2022.01) |

(52) U.S. Cl.
CPC ........ *B01L 3/502715* (2013.01); *B01F 33/30* (2022.01); *B01L 3/5027* (2013.01); *B01L 3/502761* (2013.01); *G01N 21/552* (2013.01); *G01N 21/6428* (2013.01); *G01N 33/543* (2013.01); *G01N 33/57484* (2013.01); *B01F 25/43172* (2022.01); *B01F 25/431971* (2022.01); *B01L 2200/10* (2013.01); *B01L 2300/0636* (2013.01); *B01L 2300/12* (2013.01); *B01L 2400/0487* (2013.01); *G01N 2021/6439* (2013.01); *G01N 21/648* (2013.01); *G01N 2021/6482* (2013.01)

(58) Field of Classification Search
None
See application file for complete search history.

(56) References Cited

U.S. PATENT DOCUMENTS

| | | | | |
|---|---|---|---|---|
| 8,440,093 | B1 * | 5/2013 | Nassef | G01N 15/1031 |
| | | | | 216/84 |
| 8,680,023 | B2 * | 3/2014 | Coyer | G01N 33/6845 |
| | | | | 506/32 |
| 2004/0258571 | A1 | 12/2004 | Lee et al. | |
| 2009/0053732 | A1 * | 2/2009 | Vermesh | G01N 33/54393 |
| | | | | 435/7.1 |
| 2011/0044865 | A1 * | 2/2011 | Groisman | C12M 41/36 |
| | | | | 422/503 |
| 2011/0312518 | A1 * | 12/2011 | Davis | B01L 3/502761 |
| | | | | 435/7.1 |
| 2013/0209991 | A1 * | 8/2013 | Wang | A61B 5/1473 |
| | | | | 435/7.1 |
| 2016/0334396 | A1 * | 11/2016 | Cheng | G01N 15/0656 |
| 2019/0308190 | A1 * | 10/2019 | Mao | B01L 3/5027 |

FOREIGN PATENT DOCUMENTS

WO    WO 2013166024    11/2013

OTHER PUBLICATIONS

Anderson, et al., The human plasma proteome: history, character, and diagnostic prospects. Mol Cell Proteomics. Nov. 2002;1(11):845-67.
Bardelli et al., Liquid Biopsies, What We Do Not Know (Yet). Cancer Cell. Feb. 13, 2017;31(2):172-179.
Barletta, et al., Lowering the detection limits of HIV-1 viral load using real-time immuno-PCR for HIV-1 p24 antigen. Am J Clin Pathol. Jul. 2004;122(1):20-7.
Baumeister, et al., Coinhibitory Pathways in Immunotherapy for Cancer. Annu Rev Immunol. May 20, 2016;34:539-73.
Bettegowda, et al., Detection of circulating tumor DNA in early- and late-stage human malignancies. Sci Transl Med. Feb. 19, 2014;6(224):224ra24.
Boyd, et al., An intact HDM2 RING-finger domain is required for nuclear exclusion of p53. Nat Cell Biol. Sep. 2000;2(9):563-8.
Brahmer, et al., Safety and activity of anti-PD-L I antibody in patients with advanced cancer. N Engl J Med. Jun. 28, 2012;366(26):2455-65.
Brown, et al., Role of PD-1 in regulating acute infections. Curr Opin Immunol, Jun. 2010;22(3):397-401.
Cai et al., "A molecular-imprint nanosensor for ultrasensitive detection of proteins," Nat Nanotechnol., Aug. 2010, 5:8:597-601.
Cancer Genome Atlas Research Network, "Comprehensive genomic characterization of squamous cell lung cancers," Nature. Sep. 27, 2012;489(7417):519-25.
Cancer Genome Atlas Research Network, et al. Integrated genomic analyses of ovarian carcinoma. Nature. Jun. 29, 2011;474(7353):609-15.
Carlson, et al., Somatic integration of an oncogene-harboring Sleeping Beauty transposon models liver tumor development in the mouse. Proc Natl Acad Sci U S A. Nov. 22, 2005;102(47):17059-64.

(Continued)

*Primary Examiner* — Ann Montgomery
(74) *Attorney, Agent, or Firm* — Fish & Richardson P.C.

(57) ABSTRACT

Described are chips for detecting a target in a sample including a microfluidic flow chamber comprising one or more flow channels having a capture surface and at least one micromixer. Described are methods of using this chip wherein targets are identified by total internal reflection fluorescence (TIRF).

15 Claims, 30 Drawing Sheets

(56) References Cited

OTHER PUBLICATIONS

Charles, et al., Reduction of Non-Specific Protein Adsorption Using Poly(ethylene) Glycol (PEG) Modified Polyacrylate Hydrogels In Immunoassays for Staphylococcal Enterotoxin B Detection. Sensors (Basel). 2009;9(1):645-55.
Chen, et al., Exosomal PD-L 1 contributes to immunosuppression and is associated with anti-PD-1 response. Nature. Aug. 2018;560(7718):382-386.
Cohen, et al., Combined circulating tumor DNA and protein biomarker-based liquid biopsy for the earlier detection of pancreatic cancers. Proc Natl Acad Sci U S A. Sep. 19, 2017;114(38):10202-10207.
Cohen, et al., Detection and localization of surgically resectable cancers with a multi-analyte blood test. Science. Feb. 23, 2018;359(6378):926-930.
Diamandis, et al., The failure of protein cancer biomarkers to reach the clinic: why, and what can be done to address he problem? BMC Med. Aug. 9, 2012;10:87.
Fortner, et al., Ovarian cancer early detection by circulating CA125 in the context of anti-CA 125 autoantibody levels: Results from the EPIC cohort. Int J Cancer. Apr. 1, 2018;142(7):1355-1360.
Fredriksson et al., "Protein detection using proximity-dependent DNA ligation assays," Nat Biotechnol., May 2002;20(5):473-7.
Fredriksson, et al., Multiplexed protein detection by proximity ligation for cancer biomarker validation. Nat Methods. Apr. 2007;4(4):327-9.
Gardiner, et al., A randomized, double-blind, placebo-controlled assessment of BMS-936558, a fully human monoclonal antibody to programmed death-1 (PD-1), in patients with chronic hepatitis C virus infection. PLoS One. May 22, 2013;8(5):e63818.
Genega, et al., Immunophenotype of high-grade prostatic adenocarcinoma and urothelial carcinoma. Mod Pathol. Nov. 2000;13(11):1186-91.
Gibbons, et al., Smoking, p53 mutation, and lung cancer. Mol Cancer Res. Jan. 2014; 12(1):3-13.
Giljohann, et al., Drivers of biodiagnostic development. Nature. Nov. 26, 2009;462(7272):461-4.
Havrilesky, et al., Prognostic significance of p53 mutation and p53 overexpression in advanced epithelial ovarian cancer; a Gynecologic Oncology Group Study. J Clin Oncol. Oct. 15, 2003;21(20):3814-25.
Ivics, et al., Molecular reconstruction of Sleeping Beauty, a Tc1-like transposon from fish, and its transposition in human cells. Cell. Nov. 14, 1997;91(4):501-10.
Jain et al., "Probing cellular protein complexes using single-molecule pull-down," Nat., May 2011, 26:473(7348):484-8.
Jain, et al., Single-molecule pull-down for studying protein interactions. Nat Protoc. Feb. 9, 2012;7(3):445-52.
Jones, et al., "Core signaling pathways in human pancreatic cancers revealed by global genomic analyses," Science, Sep. 26, 2008;321(5897):1801-6.
Kim, D., et al., " Protein immobilization techniques for microfluidic assays," Biomicrofluidics 7, 041501 (2013).
Lee, H., et al., "Real-time single-molecule co-immunoprecipitation analyses reveal cancer-specific Ras signaling dynamics," Nature Communications (2013), 4:1505, DOI: 10.1038/ncomms2507.
Lee, et al., p53, secreted by K-Ras-Snail pathway, is endocytosed by K-Ras-mutated cells; implication of target- specific drug delivery and early diagnostic marker. Oncogene. May 14, 2009;28(19):2005-14.
Levine, et al., p53, the cellular gatekeeper for growth and division. Cell. Feb. 7, 1997;88(3):323-31.
Levine, et al., The first 30 years of p53: growing ever more complex, Nat Rev Cancer: Oct. 2009;9(10):749-58.
Lilja, et al., Prostate-specific antigen and prostate cancer: prediction, detection and. monitoring. Nat Rev Cancer. Apr. 2008;8(4):268-78.
Lin, et al., Treatment of established tumors with a novel vaccine that enhances major histocompatibility class II presentation of tumor antigen, Cancer Res., Jan. 1, 1996;56(1):21-6.
Linder, V., et al., "Surface biopassivation of replicated poly(dimethylsiloxane) microfluidic channels and application to heterogeneous immunoreaction with on-chip fluorescence" Anal. Chem., 2001, 73, 4181-4189.
Litwin, et al., The Diagnosis and Treatment of Prostate Cancer: A Review. JAMA. Jun. 27, 2017;317(24):2532-2542.
Liu, K., et al., "Microfludic systems for biosensing" Sensors, 2010, 10, 6623-6661; doi:10.3390/s100706623.
Lokshin, et al., Circulating IL-8 and anti-IL-8 autoantibody in patients with ovarian cancer. Gynecol Oncol. Aug. 2006; 102(2):244-51.
Mahal, et al., Association of very low prostate-specific antigen levels with increased cancer-specific death in men with high-grade prostate cancer. Cancer. Jan. 1, 2016;122(1):78-83.
Moskaluk et al., "p16 and K-ras gene mutations in the intraductal precursors of human pancreatic adenocarcinoma," Cancer Res., Jun. 1, 1997;57(11):2140-3.
Muller, et al., Mutant p53 in cancer: new functions and therapeutic opportunities. Cancer Cell. Mar. 17, 2014; 25(3):304-317.
Muller, et al., p53 mutations in cancer. Nat Cell Biol. Jan. 2013; 15(1):2-8.
Nam et al., "Nanoparticle-based bio-bar codes for the ultrasensitive detection of proteins," Science, Sep. 26, 2003;301(5641):1884-6.
Nishino, et al., Monitoring immune-checkpoint blockade: response evaluation and biomarker development. Nat Rev Clin Oncol. Nov. 2017;14(11):655-668.
Okazaki, et al., A rheostat for immune responses: the unique properties of PD-1 and their advantages for clinical application., Nat. Immunol., Dec. 2013;14(12):1212-8.
Ovesny, "ThunderSTORM: a comprehensive ImageJ plug-in for PALM and STORM data analysis and super-resolution imaging," Bioinformatics, Aug. 2014, 30:16:2389-90.
Pardoll, et al., The blockade of immune checkpoints in cancer immunotherapy. Nat Rev Cancer. Mar. 22, 2012;12(4):252-64.
PCT International Preliminary Report on Patentability in Appln. No. PCT/US2017/053354, dated Dec. 11, 2017, 7 pages.
PCT International Search Report and Written Opinion in Appln. No. PCT/US2017/053354, dated Dec. 11, 2017, 8 pages.
Polanski, et al., A list of candidate cancer biomarkers for targeted proteomics. Biomark Insights. Feb. 7, 2007;1 :1-48.
Reddy, et al., Programmed death-ligand 1 (PD-L 1) is expressed in a significant No. of the uterine cervical carcinomas. Diagn Pathol. 2017; 12: 45.
Rissin et al., "Single-molecule enzyme-linked immunosorbent assay detects serum proteins at subfemtomolar concentrations," Nat. Biotechnol., Jun. 2010;28(6):595-9.
Roden, et al., How will HPV vaccines affect cervical cancer? Nat Rev Cancer. Oct. 2006;6(10):753-63.
Ruzicka, et al., Immuno-PCR with a commercially available avidin system. Science. Apr. 30, 1993;260(5108):698-9.
Saglam, et al., PD-1/PD-L 1 immune checkpoint inhibitors in advanced cervical cancer. Front Pharmacol. 2019; 10:65.
Sano, et al., Immuno-PCR: very sensitive antigen detection by means of specific antibody-DNA conjugates. Science. Oct. 2, 1992;258(5079):120-2.
Scarpa, et al., Pancreatic adenocarcinomas frequently show p53 gene mutations. Am J Pathol. May 1993; 142(5):1534-43.
Schroder, et al., Prostate cancer detection at low prostate specific antigen. J Urol. Mar. 2000;163(3):806-12.
Schroder, et al., Screening and prostate cancer mortality: results of the European Randomised Study of Screening or Prostate Cancer (ERSPC) at 13 years of follow-up. Lancet. Dec. 6, 2014;384(9959):2027-35.
Schroder, et al., Screening and prostate-cancer mortality in a randomized European study. N Engl J Med. Mar. 26, 2009;360(13):1320-8.
Shashkova, et al., Single-molecule fluorescence microscopy review: shedding new light on old problems. Biosci Rep. Jul. 21, 2017;37(4).

(56) References Cited

OTHER PUBLICATIONS

Sokoloff, et al., Characterizing prostatic adenocarcinomas in men with a serum prostate specific antigen level of<4.0 ng/ml. BJU Int. Mar. 2004;93(4):499-502.
Soussi, et al., p53 Antibodies in the sera of patients with various types of cancer: a review. Cancer Res. Apr. 1, 2000;60(7):1777-88.
Srinivas, et al., Trends in biomarker research for cancer detection. Lancet Oncol. Nov. 2001;2(11):698-704.
Stroock, et al., "Chaotic mixer for microchannels," Science. Jan. 25, 2002;295(5555):647-51.
Sweeney, et al., Visualizing the kinetics of tumor-cell clearance in living animals. Proc Natl Acad Sci U S A. Oct. 12, 1999;96(21):12044-9.
Topalian, et al., Safety, activity, and immune correlates of anti-PD-1 antibody in cancer. N Engl J Med. Jun. 28, 2012;366(26):2443-54.
Wang et al., Mutant proteins as cancer-specific biomarkers. Proc Natl Acad Sci U S A. Feb. 8, 2011;108(6):2444-9.
Wang, et al., Multisite aggregation of p53 and implications for drug rescue. Proc Natl Acad Sci U S A. Mar. 28, 2017;114(13):E2634-E2643.
Zhang et al., "A sensitive and high-throughput assay to detect low-abundance proteins in serum," Nat. Med., Apr. 2006, 12:4:473-7.
Zhou, et al., Soluble PD-L 1 as a Biomarker in Malignant Melanoma Treated with Checkpoint Blockade. Cancer Immunol Res. Jun. 2017;5(6):480-492.
Zou, Inhibitory B7-family molecules in the tumour microenvironment, Nat Rev Immunol. Jun. 2008;8(6):467-77.

\* cited by examiner

NON-INVASIVE CANCER DETECTION AND ANALYSIS BY SINGLE-MOLECULE IMAGING

REFERENCE TO RELATED APPLICATIONS

This application is a continuation of U.S. application Ser. No. 16/336,124, filed Mar. 25, 2019, which is a 35 U.S.C. § 371 U.S. national entry of International Application PCT/US2017/053354 having an international filing date of Sep. 26, 207, which claims the benefit of U.S. Provisional Application No. 62/399,545, filed Sep. 26, 2016, the content of each of the aforementioned applications is herein incorporated by reference in their entirety.

STATEMENT OF GOVERNMENTAL INTEREST

This invention was made with government support under grant no. RO1CA114425 awarded by the National Institutes of Health. The government has certain rights in the invention.

BACKGROUND OF THE INVENTION

Over 8 million people around the world die of cancer each year. This high mortality rate is primarily due to belated detection of the disease at an advanced stage, after the tumor has spread to a distant site. This point is vividly illustrated by epidemiologic data from cancer types for which effective screening methods are available (i.e., cervical, breast, colon, skin cancer). For each of these cancer types, detection of the disease at an early stage translates into a >90% 5-year survival rate, while late detection has a <20% survival rate. Furthermore, for ovarian and pancreatic cancer—highly lethal cancer types which lack effective screening methods—the disease is almost always not found until it has progressed to stage III/IV, which carries a <10% 5-year survival rate. However, even for these lethal cancer types, early detection (stage I) translates into a close to 100% survival rate. Together, these statistics indicate that, in the vast majority of cases, cancer can be successfully treated if found early on. Therefore, effective early detection methods have the potential to dramatically bring down the mortality rate of cancer.

SUMMARY OF THE INVENTION

One embodiment of the present invention is a chip for detecting a target in a sample comprising: a microfluidic flow chamber comprising one or more flow channels comprising a capture surface and at least one micromixer wherein the capture surface comprises a binding molecule. Suitable materials used to make the capture surface include glass, silicon, PDMS, polystyrene, polycarbonate, polyvinylchloride, polymethyl methacrylate, a cyclic olefin polymer or a combination thereof, as examples. The binding molecule may be a chemical conjugate and a suitable chemical conjugate is a silane based compound. It is preferred that a silane based compound used in the present invention is a silane group comprising one or more moieties selected from the group comprising an amino, a vinyl, an epoxy, an acryloxy, a methacryloxy, a styryl, an isocyanurate, an ureide, a sulfide, an isocyanate, a mercapto, or a combination thereof. Other suitable silane based compounds for use in the present invention may be further conjugated to a chemical compound comprising: (a) one or more reactive groups selected from the group comprising succinimidyl valerate, and also including N-hydroxysuccinimide ester, imidoester, epoxide, isothiocyanate, isocyanate, sulfonyl chloride, aldehyde, carbodiimide, acyl azide, anhydride, fluorobenzene, carbonate, fluorophenyl ester, or a combination thereof; and (b) one or more passivation groups with or without biotin modification selected from the group comprising polyethylene glycol, polyacrylamide, poly(acrylic acid), poly(N-hydroxyethyl acrylamide), poly(2-hydroxyethyl methacrylate), poly(2-methacryloyloxyethyl phosphorylcholine), poly(vinyl alcohol), poly(vinyl pyrrolidone), hydroxyethylcellulose, hydroxypropyl methylcellulose, dextran, hyaluronic acid, or a combination thereof.

Alternatively, a suitable chemical conjugate may comprise: (a) one or more reactive groups selected from the group comprising succinimidyl valerate, and also including N-hydroxysuccinimide ester, imidoester, epoxide, isothiocyanate, isocyanate, sulfonyl chloride, aldehyde, carbodiimide, acyl azide, anhydride, fluorobenzene, carbonate, fluorophenyl ester, or a combination thereof; and (b) one or more passivation groups with or without biotin modification selected from the group comprising polyethylene glycol, polyacrylamide, poly(acrylic acid), poly(N-hydroxyethyl acrylamide), poly(2-hydroxyethyl methacrylate), poly(2-methacryloyloxyethyl phosphorylcholine), poly(vinyl alcohol), poly(vinyl pyrrolidone), hydroxyethylcellulose, hydroxypropyl methylcellulose, dextran, hyaluronic acid, or a combination thereof. The chip of the present invention may include a capture molecule covalently conjugated to the capture surface by the chemical conjugate.

Other suitable binding molecules used in the present invention include a first biotin binding complex selected from the group comprising biotin, avidin, NeutrAvidin, streptavidin, or a combination thereof. Such a chip may include a capture molecule that comprises a second biotin-labeled complex that is bound to the chip by the first biotin binding complex. A suitable second biotin binding complex may be selected from the group comprising biotin, avidin, NeutrAvidin, streptavidin, or a combination thereof.

Suitable micromixers used in a chip of the present invention may be a passive micromixer selected from the group comprising embedded barriers, staggered herringbone grooves, intersecting channels, lamination, serpentine structure, slanted walls, walls with boxes, twisted channels, surface chemistry, zigzag channels or a combination thereof. Other suitable micromixers include active micromixer selected from the group comprising acoustic, dielectophoretic, electrohydrodynamic force, electrokinetic instability, electrokinetic time-pulsed, magnetic, magneto-hydrodynamic force, pressure perturbation, thermal, or a combination thereof. Alternatively, a chip of the present invention may have a combination of a passive micromixer and an active micromixer.

A suitable microfluidic flow chamber of the present invention may be made of a material selected from the group comprising polydimethylsiloxane (PDMS), silicon, glass, polystyrene, polycarbonate, polyvinylchloride, polymethyl methacrylate, cyclic olefin copolymer, or a combination thereof. Suitable dimensions of a flow channel include a width in the range of 0.025 mm to 10 mm, 1 mm to 6 mm, and 2 mm to 4 mm; a length in the range of 0.1 mm to 10 mm, 0.5 mm to 5 mm, and 1 mm to 3 mm; and a height in the range of 0.001 mm to 2 mm, 0.001 mm to 1 mm, and 0.01 mm to 1 mm. The most preferred width range is 0.05 mm to 0.5 mm.

Another embodiment of the present invention is a system for detecting a target in a sample comprising: a chip of the present invention; and a total internal reflection fluorescence (TIRF) microscopy system wherein the TIRF microcopy system is able to detect individual target molecules if present on the chip. This system further comprising an external pump able to drive continuous, unidirectional, or bidirectional fluid flow through the flow channels in a single pass or by recirculation.

Another embodiment of the present invention is a method of sealing a chip comprising: a) providing a surface comprising one or more flow channels comprising a binding molecule; b) placing an elastomer cover fabricated with the dimensions of the one or more flow channels on top of the one or more flow channels; c) exposing the elastomer surface and the microfluidic flow chamber with plasma to form a treated surface preferably in the inside of a plasm etcher; d) removing the elastomer cover from the treated surface; e) sealing the treated microfluidic flow chamber to the treated surface forming a covalently bonded chip. The sealing step using a plasma etcher occurs with atmospheric or oxygen plasma for 1 to 300 seconds, 50 to 200 seconds, or 100 to 300 seconds; at an RF power in the range of 5-500 W, 10-400 W, or 100-300 W; at a pressure of 10 to 1,000 mtorr, or 100 to 900 mtorr, or 200 to 800 mtorr. The most preferred range is from 10 to 60 seconds and an RF power of 10-50 W. The surface maybe composed of a material including glass, silicon, PDMS, polystyrene, polycarbonate, polyvinylchloride, polymethyl methacrylate, cyclic olefin polymer, or a combination thereof as examples. Suitable binding molecules used in the present invention are describe above.

Another embodiment of the present invention includes a method of detecting a target in a sample comprising: a) providing a chip comprising a microfluidic flow chamber comprising one or more flow channels comprising a capture surface and at least one micromixer wherein the capture surface comprises a binding molecule b) placing a capture molecule specific to a target molecule into the one or more flow channels of the chip so it binds to the first binding molecule; c) placing a sample containing a target molecule recognized by the capture molecule into the one or more flow channels of a chip; d) placing a detection molecule specific for the target molecule into one or more flow channels of the chip; and e) detecting the target molecule. It is preferred that the chip is connected to an external pump able to drive continuous, either unidirectional or bidirectional, fluid flow through the flow channels, either in a single pass or recirculation format and the target molecule is detected digitally in the sample by total internal reflection fluorescence (TIRF) microscopy. It is also preferred that the detection molecule is labeled with a fluorophore and binds to the target creating a fluorophore-labeled target complex wherein the fluorophore-labeled target complex may be individually detected by TIRF, and the TIRF signal is collected by an electron multiplying charge coupled device camera with single photon sensitivity. A capture molecule maybe conjugated to a chip surface by the first binding molecule having: (a) one or more reactive groups selected from the group comprising: succinimidyl valerate, N-hydroxysuccinimide ester, imidoester, epoxide, isothiocyanate, isocyanate, sulfonyl chloride, aldehyde, carbodiimide, acyl azide, anhydride, fluorobenzene, carbonate, fluorophenyl ester, or a combination thereof; and (b) one or more passivation groups with or without biotin modification, selected from the group comprising polyethylene glycol, polyacrylamide, poly(acrylic acid), poly(N-hydroxyethyl acrylamide), poly(2-hydroxyethyl methacrylate), poly(2-methacryloyloxyethyl phosphorylcholine), poly(vinyl alcohol), poly(vinyl pyrrolidone), hydroxyethylcellulose, hydroxypropyl methylcellulose, dextran, hyaluronic acid, or a combination thereof. Alternative suitable first binding molecules includes biotin, avidin, streptavidin, or NeutrAvidin, or a combination thereof as examples. In some applications a capture molecule may have a second binding molecule that is able to form a biotin-associated complex selected from the group comprising biotin, avidin, streptavidin, or NeutrAvidin, or a combination thereof. Suitable capture molecules of the present invention include an antibody, a peptide, a protein, a nucleic acid, a lipid, a carbohydrate, an aptamer, or a combination thereof as examples. In the many embodiments of the present invention one or more flow channels may be a positive control (or reference) or a negative control (or reference). Examples of suitable target molecules are a tumor-specific nucleocytoplasmic protein; a mutant oncoprotein selected from the group comprising RAS, BRAF, PIK3CA, EGFR, NOTCH1 or a combination thereof; a mutant tumor suppressor protein selected from the group comprising P53, CDKN2A, PTEN, RB, APC, SMAD, ARID1A, MLL2, MLL3, GATA3, VHL, PBRM1 or a combination thereof; and a pathogen-encoded an oncoprotein derived from an oncogenic pathogen selected from the group comprising HPV, EBV, HBV, HCV, HTLV-1, KSHV, Merkel cell polyomavirus, or a combination thereof as examples. Suitable samples used in the embodiments of the present invention include whole blood, plasma, serum, RBC fraction, urine, saliva, cerebrospinal fluid, semen, sweat, bile, gastric contents, breast milk, exudates, ascites, lymph, sputum, lavage fluid, and bronchial fluid. The sample is a preferable a human sample. It is also suitable for a detection molecule of the present invention to have a label such as a fluorophore label, a colorimetric label, a radioactive label, a luminescence label, an electromagnetic label or a combination thereof as examples.

Another embodiment of the present invention is a method of detecting one or more biomarkers in a clinical sample comprising: a) providing a chip comprising a capture surface comprising a first binding molecule; and a microfluidic flow chamber comprising one or more flow channels comprising the capture surface and at least one micromixer, b) placing a capture molecule specific to a biomarker into the one or more flow channels of the chip so it binds to the first binding molecule; c) placing a sample potentially containing a biomarker into one or more flow channels of the chip; d) placing a detection molecule specific for the biomarker into one or more flow channels of the chip; and e) detecting the biomarker in the sample by TIRF microscopy. As mentioned it is preferred that chips of the present invention are connected to an external pump able to drive continuous, either unidirectional or bidirectional, fluid flow through the flow channels, either in a single pass or recirculation format. In embodiments of the present invention a TIRF signal is generated that is collected by an electron multiplying charge coupled device camera with single photon sensitivity. It is suitable that the detection molecule is labeled with a fluorophore and binds to the biomarker creating a fluorophore-labeled biomarker complex wherein a fluorophore-labeled biomarker complex is detected digitally by a TIRF microscopy system that is capable of detecting single biomarker molecules. Through digital signal processing and analysis, the TIRF signal can be quantified and converted into the absolute amount of target molecules by counting the number of fluorophore-labeled target complexes that score over a set threshold fluorescence value over a defined imaging region.

Unless defined otherwise, all technical and scientific terms used herein have the meaning commonly understood by a person skilled in the art to which this invention belongs.

The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function such as Indoleamine 2, 3-dioxygenase (an oxidoreductase) catalyzing the degradation of the essential amino acid tryptophan (trp) to N-formyl-kynurenine.

The term "antibody," as used in this disclosure, refers to an immunoglobulin or a fragment or a derivative thereof, and encompasses any polypeptide comprising an antigen-binding site, regardless of whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')$_2$, Fv, scFv, Fd, dAb, and other antibody fragments that retain antigen-binding function, i.e., the ability to bind, for example, PD-Li, specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CHl domain of the heavy chain.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "biomarker" or "marker" is meant any protein or polynucleotide having an alteration in expression level or activity that is associated with a disease or disorder.

By "biotin binding complex" or "biotin binding complex molecule" is meant a molecule such as avidin, neutravidin, or strepavidin that binds to biotin or a molecule that binds to biotin such as avidin, neutravidin, or streptavidin.

By "capture molecule" is meant a molecule, such as antibody, peptide, protein, nucleic acid, lipid, carbohydrate, or aptamer, or a combination thereof for example, preferably attached to biotin binding complex molecule that binds to a target, for example a biomarker.

The term "detection molecule" refers to a molecule, such as an Ab or aptamer for example that preferably is labelled and binds to a target, for example a target or a peptide.

By "detect" or "detecting" means to identify the presence, absence or amount of the analyte, target, biomarker, for example, to be detected.

By"labelled," "label" or "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "Diagnostic" is meant identifying the presence or nature of a pathologic condition, i.e., cancer. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

By "disease" is meant any condition or disorder that damages or interferes with the normal function of a cell, tissue, or organ. Examples of diseases include pancreatic cancer. By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "express" refers to the ability of a gene to express the gene product including for example its corresponding mRNA or protein sequence (s).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "Immunoassay" is meant an assay that uses an antibody to specifically bind an antigen (e.g., a marker). The immunoassay is characterized by the use of specific binding properties of a particular antibody to isolate, target, and/or quantify the antigen.

By, "obtaining" as in "obtaining an agent" is meant synthesizing, purchasing, or otherwise acquiring the agent.

By "mAb" is meant monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

By "polypeptide," "peptide" and "protein" is meant that these terms are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" is meant a negative alteration of at least 10%, 25%, 50%, 75%, or 100%.

By "reference" is meant a standard or control conditions such as a sample (human cells) or a subject that is a free, or substantially free, of an agent such as one or more inhibitors or a vaccine.

By "sensitivity" is meant the percentage of subjects with a particular disease.

By "specificity" is meant the percentage of subjects correctly identified as having a particular disease i.e., normal or healthy subjects. For example, the specificity is calculated as the number of subjects with a particular disease as compared to non-cancer subjects (e.g., normal healthy subjects).

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Such treatment (surgery and/or chemotherapy) will be suitably administered to subjects, particularly humans, suffering from, having, susceptible to, or at risk for pancreatic cancer or disease, disorder, or symptom thereof. Determination of those subjects "at risk" can be made by any objective or subjective determination by a diagnostic test or opinion of a subject or health care provider (e.g., genetic test, enzyme or protein marker, a marker (as defined herein), family history, and the like).

BRIEF DESCRIPTION OF THE DRAWINGS

FIG. 23 3D confocal micrographs of micromixers on top layer of SMAC chip at different view angles. The staggered herringbone micromixer is a single design example out of multiple potential design variations which could be incorporated into a chip.

Continuous, closed-loop flow within the channels is actuated by an automated pump; the pump may act through peristaltic, pneumatic, or infusion-withdrawal mechanisms. Our continuous flow design enables high efficiency capture of target proteins onto the SMAC chip surface and rapid concentration of these target proteins by >10,000-fold.

Figure 25:
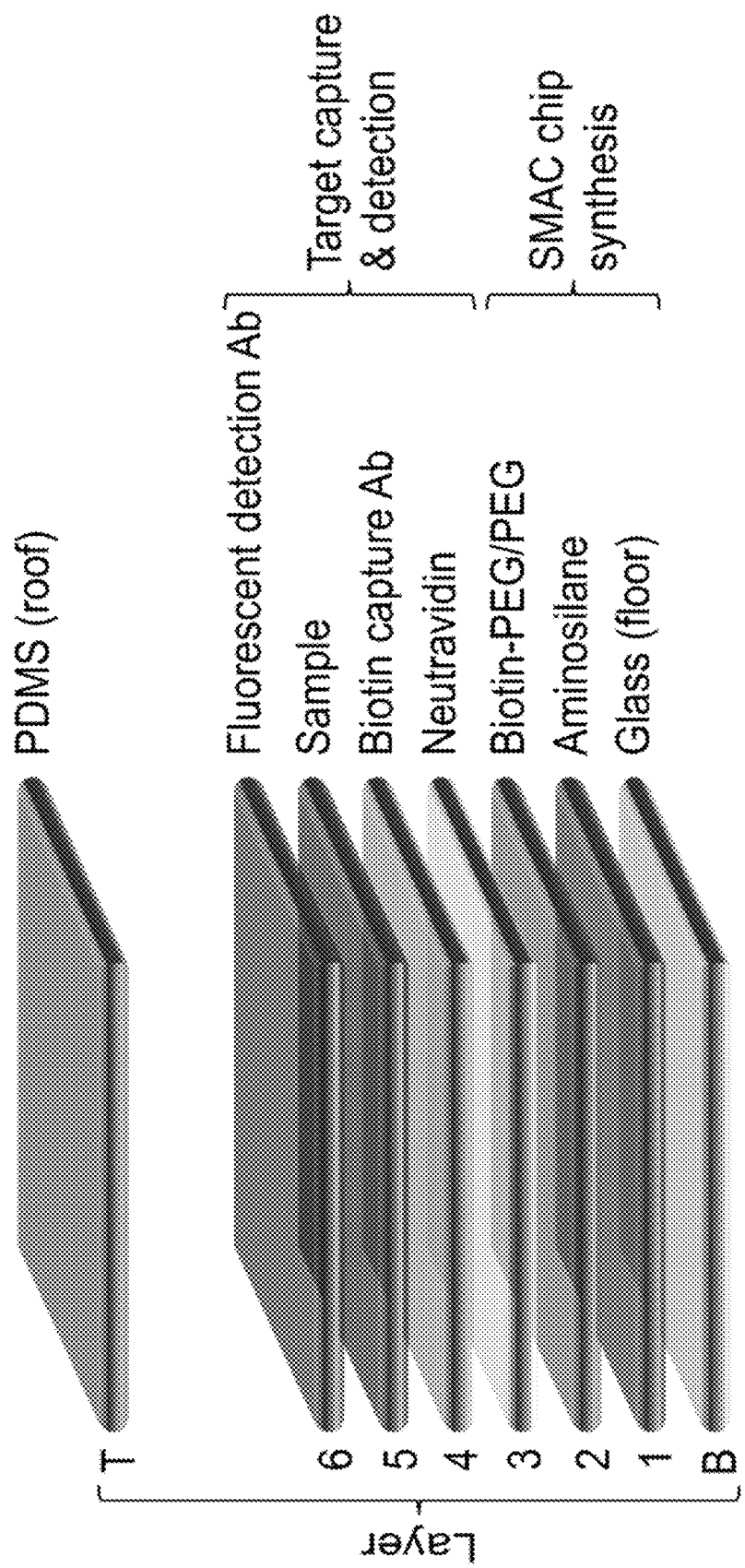

FIG. 25 Components of a SMAC Chip. Layers B, 1, 2, 3 are part of the SMAC chip synthesis process and layers 4, 5, and 6 are part of target capture and detection. Layer T is the top or roof.

Figure 26:
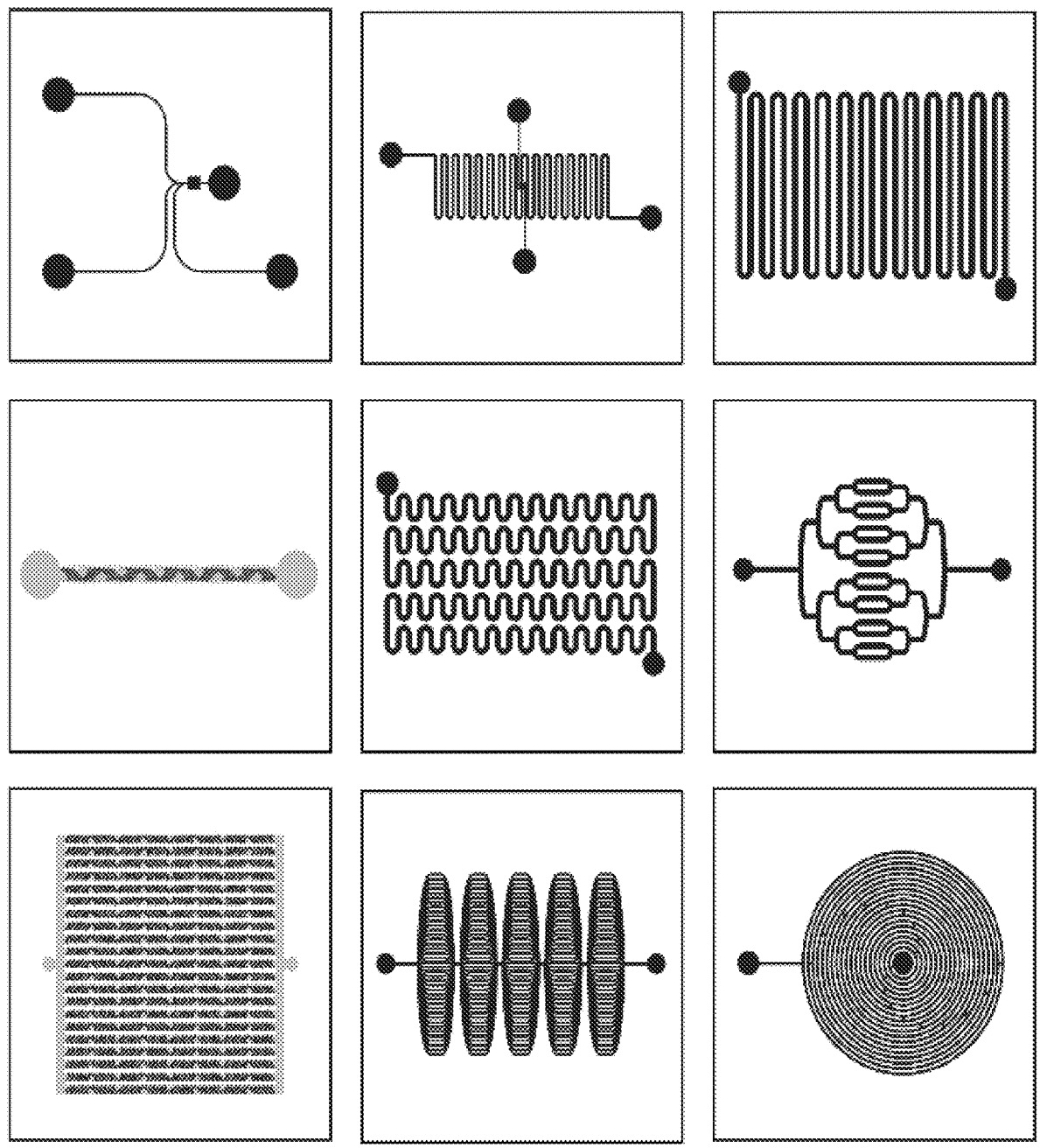

FIG. 26 Examples of potential SMAC chip flow channel designs. The flow channels are formed by the design present in the bottom (FIG. 25) and is enclosed by the top (roof) (FIG. 25). The channels may have many shapes depending upon the application.

Figure 27:
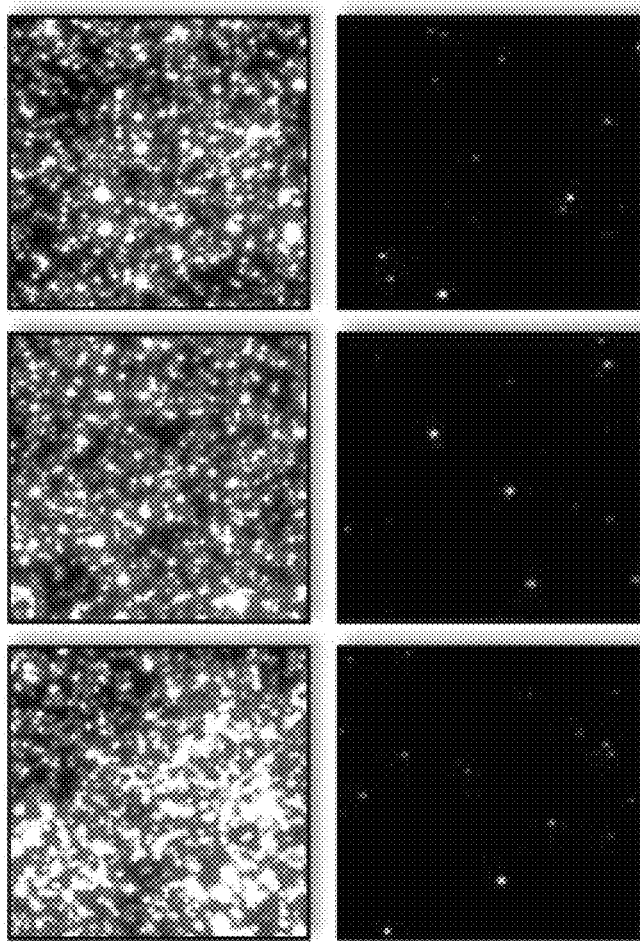

FIG. 27 Effect of oxygen plasma exposure on non-specific binding of a pre-coated glass substrate. Shown is a non-specific binding test in which fluorophore-labeled detection reagent was added to SMAC chips with pre-coated glass substrate that underwent either conventional plasma bonding (top panel) or adhesive bonding (bottom panel). Note that conventional plasma bonding damages the PEG surface coating, leading to a high degree of non-specific detection Ab binding as assessed by single molecule imaging.

Figure 28:
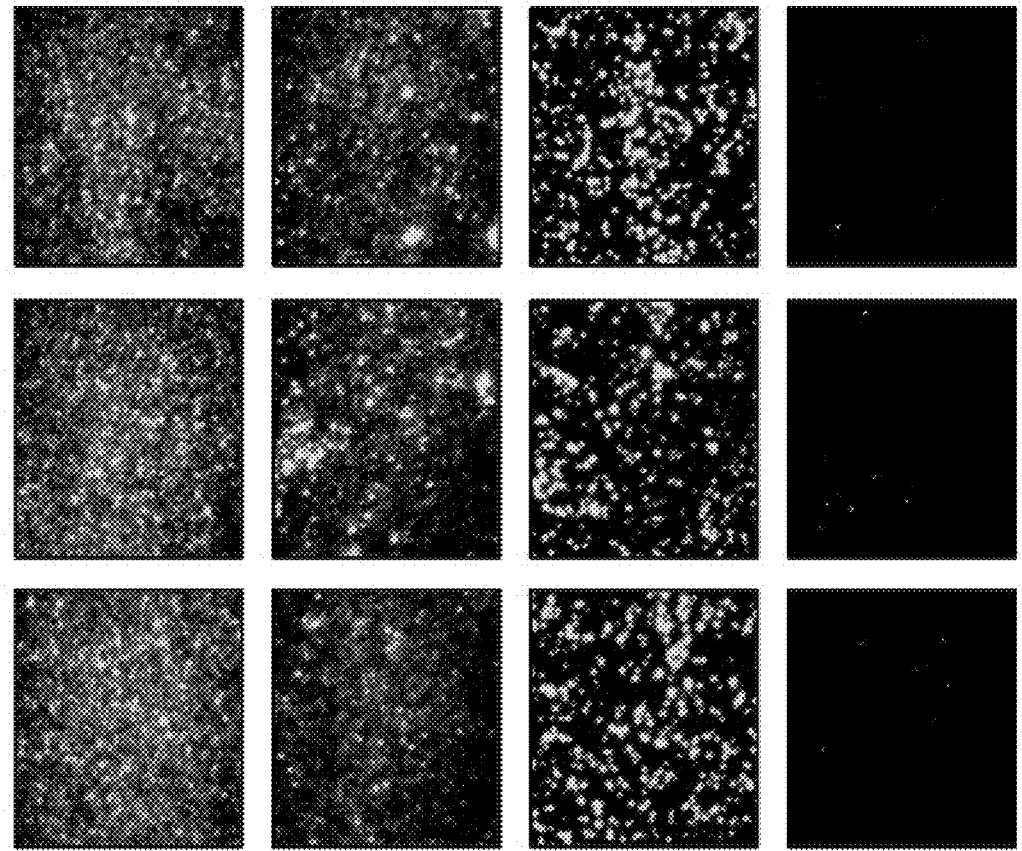

FIG. 28 Specific binding and background analysis of SMAC chips conjugated to PEG/biotin-PEG by in situ coating or conventional coating. Shown is a specific binding and background comparison of SMAC chips conjugated with PEG/biotin-PEG by either in situ coating or the standard coating technique. Note that, compared to conventional coating, in situ coating is prone to a large amount of non-specific detection Ab binding. Therefore, conventional coating is the preferred method for single-molecule techniques. Our plasma protection bonding method allows precise microfluidic devices to be produced using an intact conventional surface coating (see FIG. 29).

Figure 29:
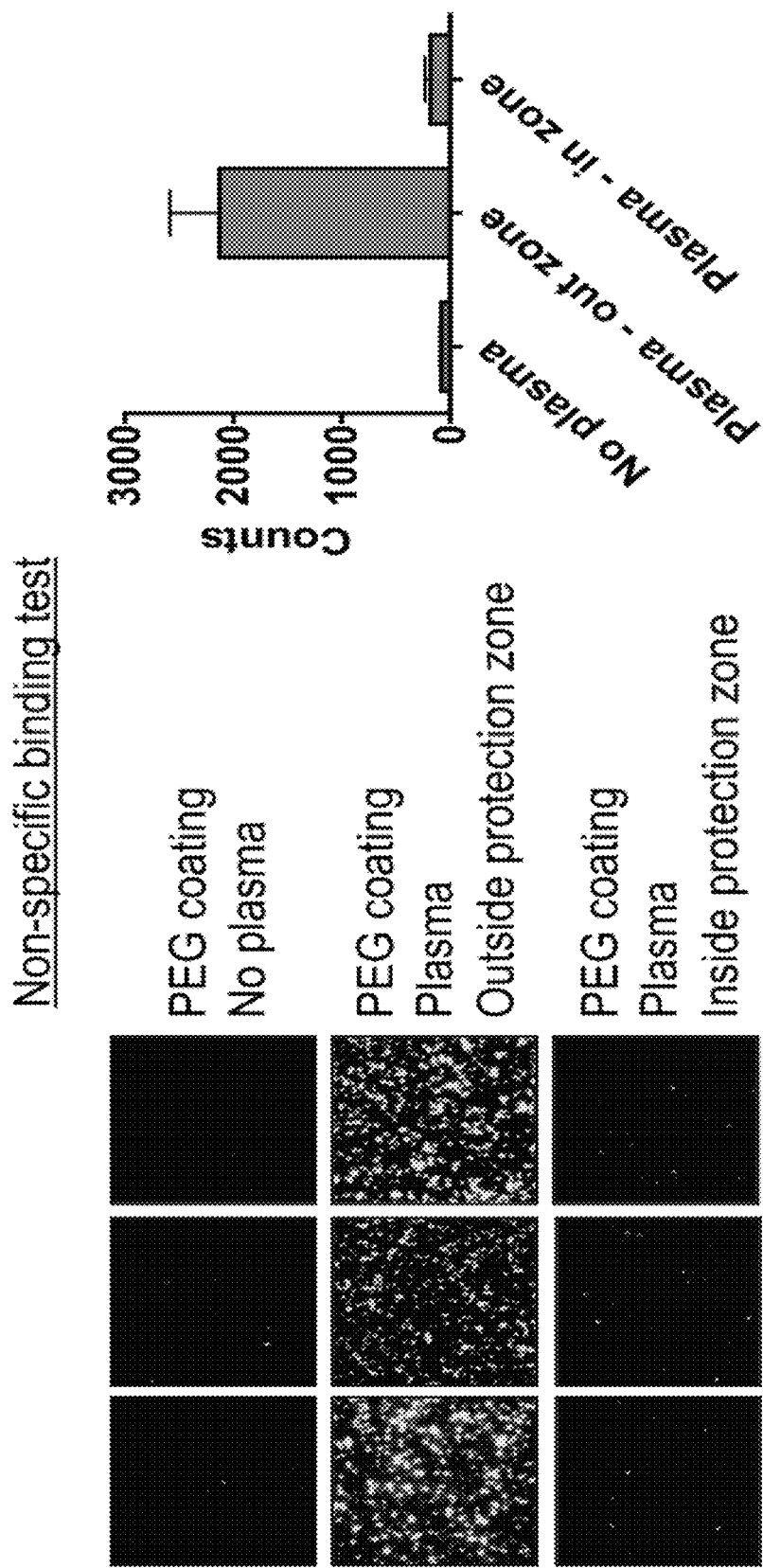

FIG. 29 Non-specific binding analysis of regions of a SMAC chip inside or outside of a "plasma protection zone." Shown is a non-specific binding test of a SMAC chip in which the elastomer cover was placed on only part of the PEG/biotin-PEG-conjugated glass substrate in the channel. Note that regions of the capture surface that lie outside the 'plasma protection zone' (cover) display a high level of non-specific detection Ab binding, while regions inside this protection zone are have very low non-specific detection Ab binding (similar to a capture surface without plasma exposure). Thus, our plasma protection bonding technique enables precise bonding geometries to be achieved without altering the capture surface coating.

Figure 30:
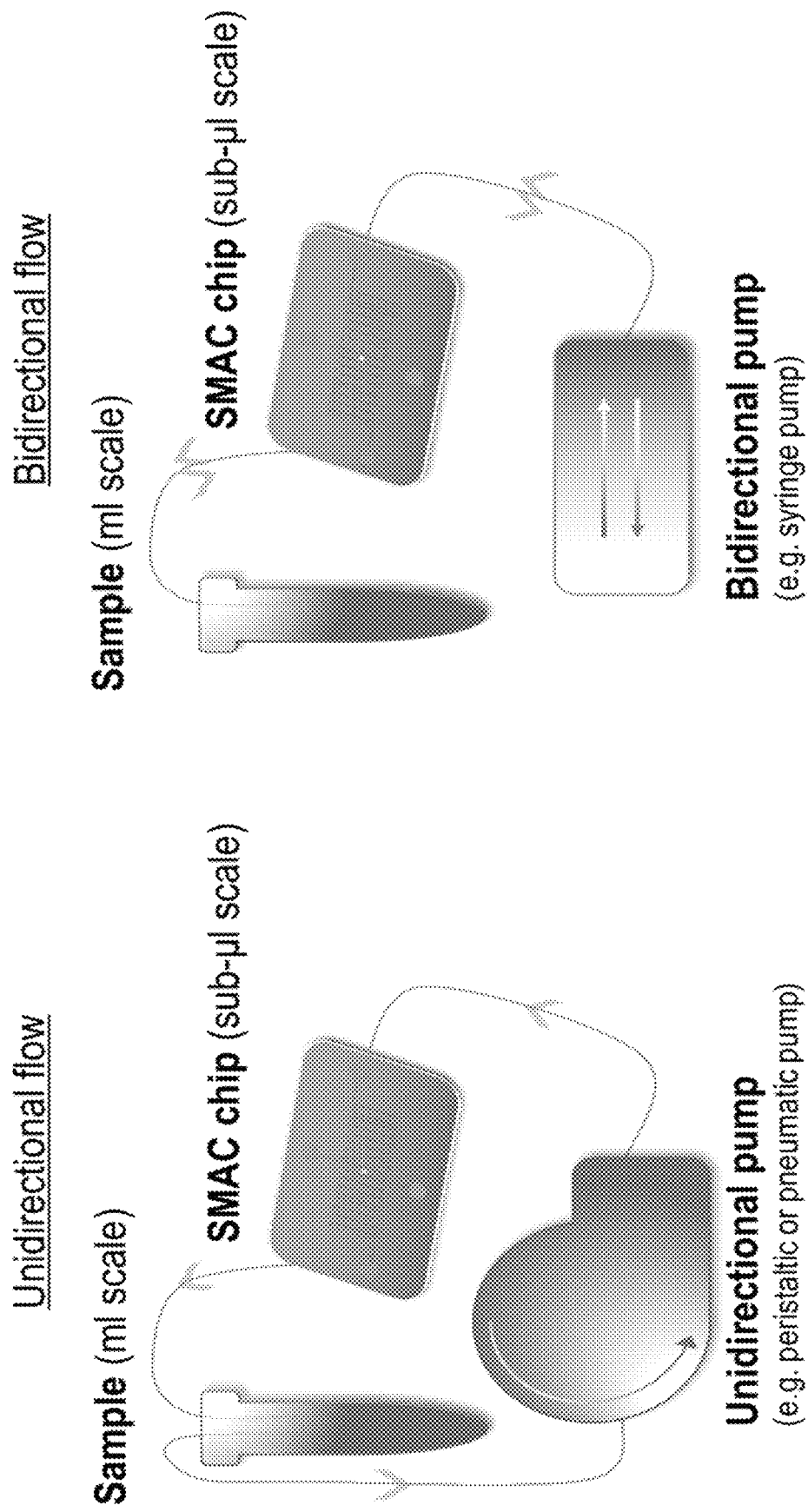

FIG. 30 Schematic diagrams of possible circulation systems configurations. Shown are diagrams of two potential configurations for the circulation system, with either a unidirectional pump or bidirectional pump.

DETAILED DESCRIPTION OF THE INVENTION

Unfortunately, effective non-invasive early detection methods do not exist for the most lethal cancer types due to the lack of true tumor-specific biomarkers. Current ELISA-based detection methods rely on biomarkers that are merely associated with a particular cancer but could also be found under other non-malignant physiologic conditions. This drawback precludes the use of these methods for universal cancer screening. Furthermore, while PCR-based analysis of mutant tumor DNA is an attractive alternative strategy because it is in principle highly cancer-specific, mutant tumor DNA is in most cases not found in the circulation until the disease has progressed to late stage. These challenges led us to search for a new class of biomarkers that are exquisitely tumor-specific and also present in the circulation in early-stage cancer. The inventors reasoned that there are 2 types of true tumor-specific biomarkers: first, mutant endogenous proteins (i.e., oncoproteins, tumor suppressor proteins) encoded within the genome of tumor cells; and second, exogenous oncoproteins encoded within the genome of cancer-causing pathogens (e.g., *H. pylori*, EBV, HBV, HCV, HPV). Because these true tumor-specific biomarkers virtually all reside within the nucleus or cytoplasm of tumor cells, and hence would be invisible in the circulation to current ELISA-based detection methods (which have a detection limit in the pM range), the inventors have created an entirely new way to 'see' vanishingly low levels (fM and below) of these biomarkers known as the SMAC chip technology.

The inventors developed SMAC technology, a platform technology for the ultra-sensitive detection and digital quantification of proteins or other therapeutic molecules. The inventors have named this technology SMAC, for Single Molecule Analysis after Capture. SMAC integrates microfluidics with single-molecule imaging and possesses a detection limit several orders of magnitude superior to ELISA-based methods. The inventors discovered by SMAC that tumor-derived nucleocytoplasmic proteins are released into the circulation in early-stage cancer, prior to the onset of clinical signs, at trace levels far below the ELISA detection limit. Indeed, in multiple preclinical models, the inventors found that SMAC could readily identify early-stage cancer with 100% accuracy simply from a small sample of blood. By contrast, qPCR detection of tumor DNA in the circulation could only identify late-stage cancer in a fraction of cases, when the tumor mass was already well-established ($\geq 500$ mm$^3$). Furthermore, in a cohort of ovarian cancer patients, SMAC blood analysis of the transcription factor p53 could reliably identify the presence of cancer with 90% sensitivity and 100% specificity. The inventors' data underscore the potential for SMAC—together with the constellation of tumor-specific biomarkers this platform enables—to revolutionize the field of early cancer detection and diagnosis.

Figure 1:
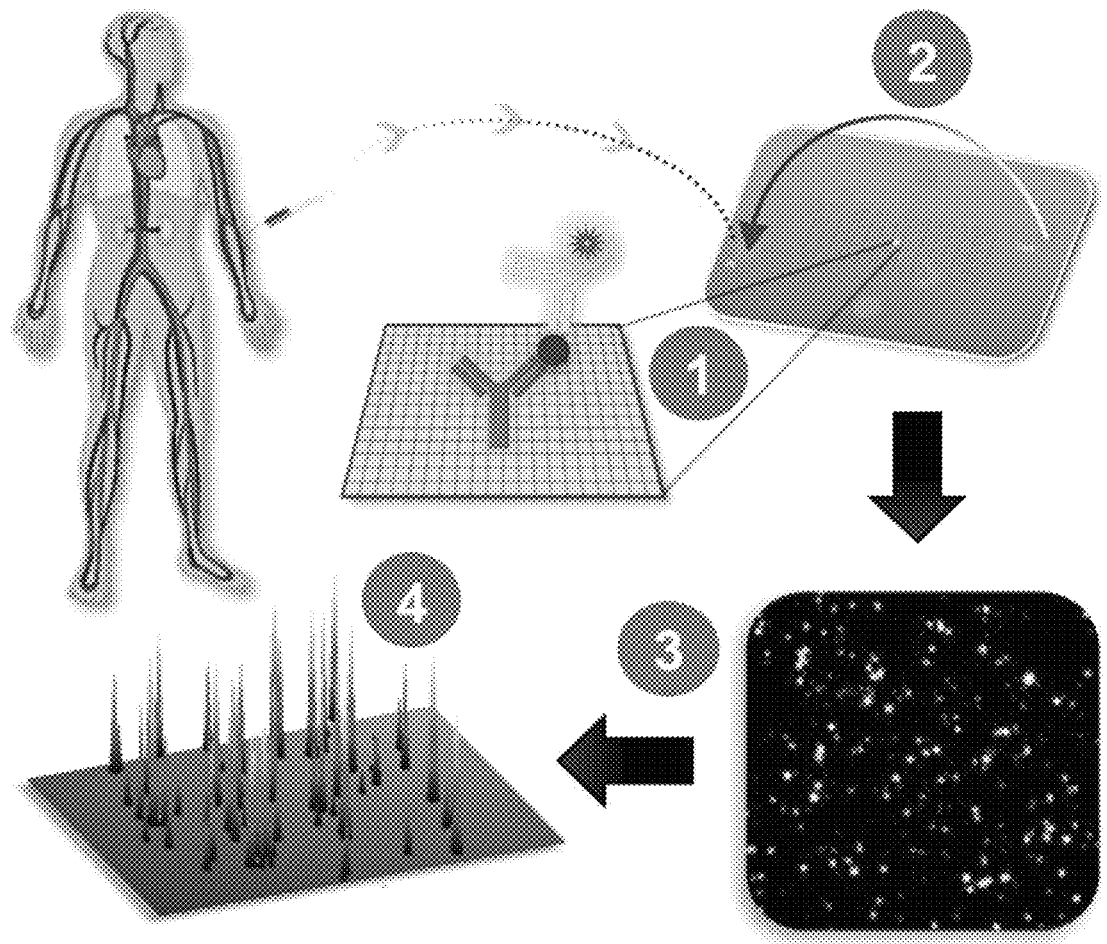
FIG. 1 Schematic diagram of Single Molecule Analysis after Capture (SMAC) technology. The SMAC platform is built on 4 fundamental innovations. (1) Target proteins are captured on a precisely engineered microfluidic SMAC chip that is conjugated with an ultra-high density of target-specific antibodies and exhibits extremely low non-specific absorption of proteins. (2) High velocity, closed-loop flow through the chip is actuated by a pump that acts synergistically with the staggered herringbone roof geometry of the SMAC chip to efficiently concentrate target proteins. (3) Target proteins are probed with fluorophore-labeled detection antibodies and visualized in space by single-molecule TIRF microscopy. Each dot in the representative SMAC micrograph depicts 1 (or occasionally 2) absolute copies of target molecule. (4) Target molecule number is automatically determined by a specially designed computer algorithm that discriminates between specific and non-specific binding events and calculates the number of fluorescence spots that score above a set intensity threshold.
Figure 2:
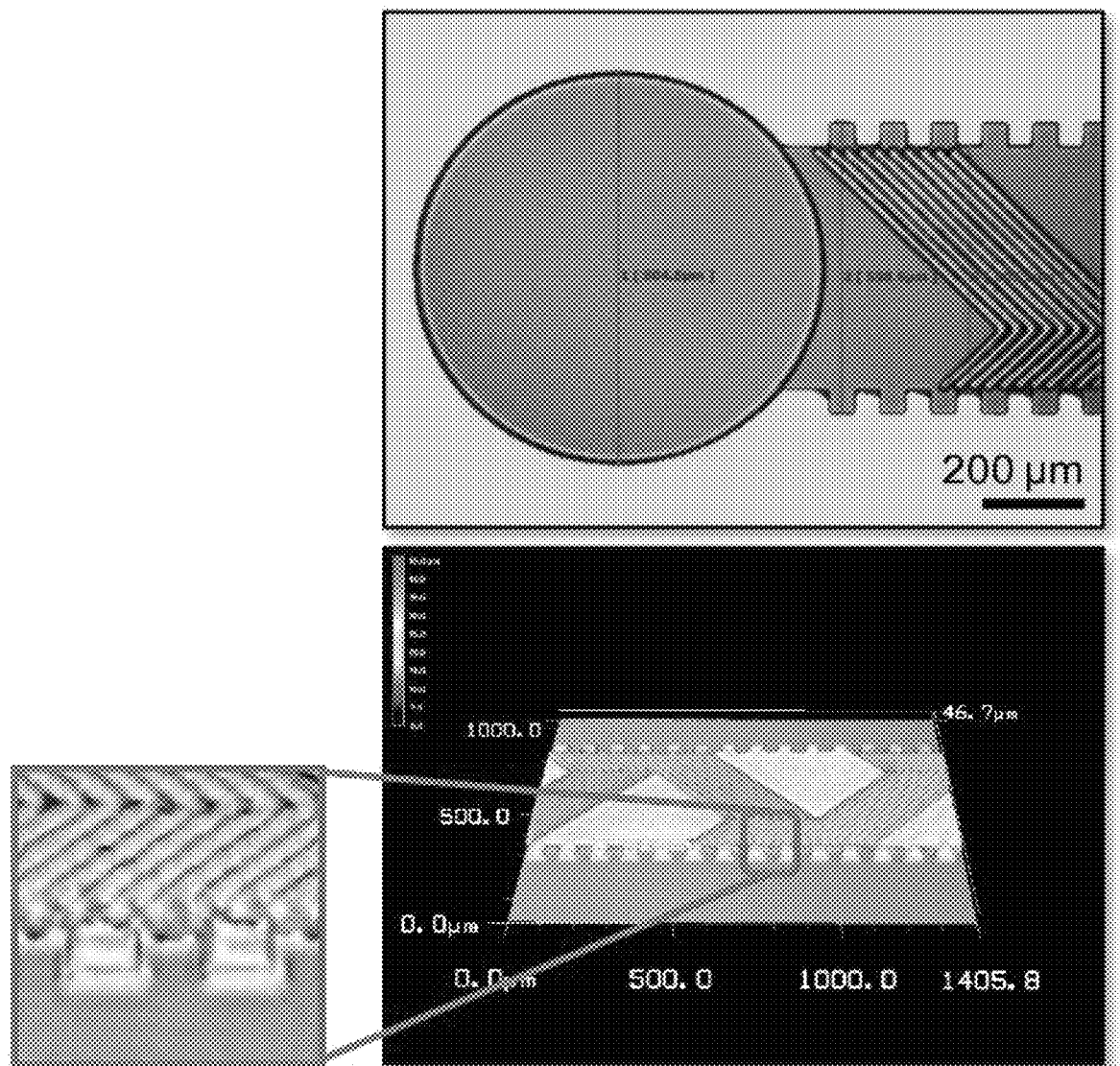
FIG. 2 Microfluidic SMAC chip design prototype. Representative 2D (top) and 3D (bottom) confocal micrographs of a SMAC chip prototype are shown. Inlet/outlet holes (800 μm diameter) are connected to a rectangular flow channel (200-1,000 μm width×5,000 μm length). Chaotic flow patterns are achieved by introducing side ridges into the channel. The side ridges can be complemented with a staggered herringbone roof to create counter-rotating microvortices. Alternating arrays of 5 herringbone grooves are offset at 33% distance into the channels. Multiple channel and roof heights are possible depending on the intended application. In general, the roof depth should be ~25-50% of the channel height. We have fabricated devices over a wide range of total heights, from ~20-70 μm to >250 μm. Note that other passive/active micromixer design variations could be incorporated into the chip to improve capture efficiency.
Figure 3:
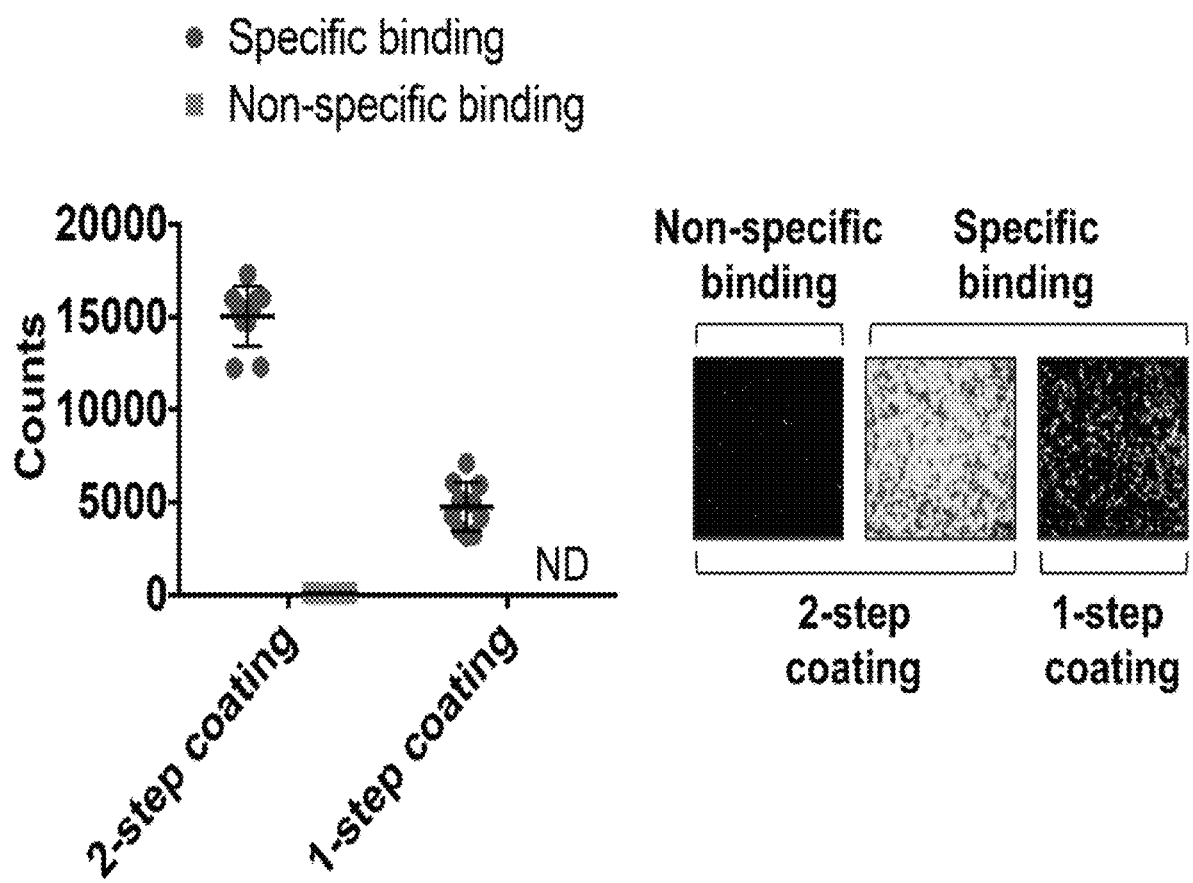
FIG. 3 Effect of 2-step versus 1-step PEG/biotin-PEG coating on target capture and detection. Glass coverslips were passivated with PEG and biotin-PEG by either 1- or 2-step coating. In 1-step coating, coverslips were passivated overnight with a PEG/biotin-PEG mixture. In 2-step coating, coverslips were passivated first with biotin-PEG for 4 hr, washed, and then passivated with a PEG/biotin-PEG mixture overnight. Coverslips were assembled with PDMS flow channels and passed with GFP under continuous circulation. Samples were examined by single molecule imaging. Our 2-step coating method improves protein detection by 3-fold relative to 1-step coating.
Figure 4:
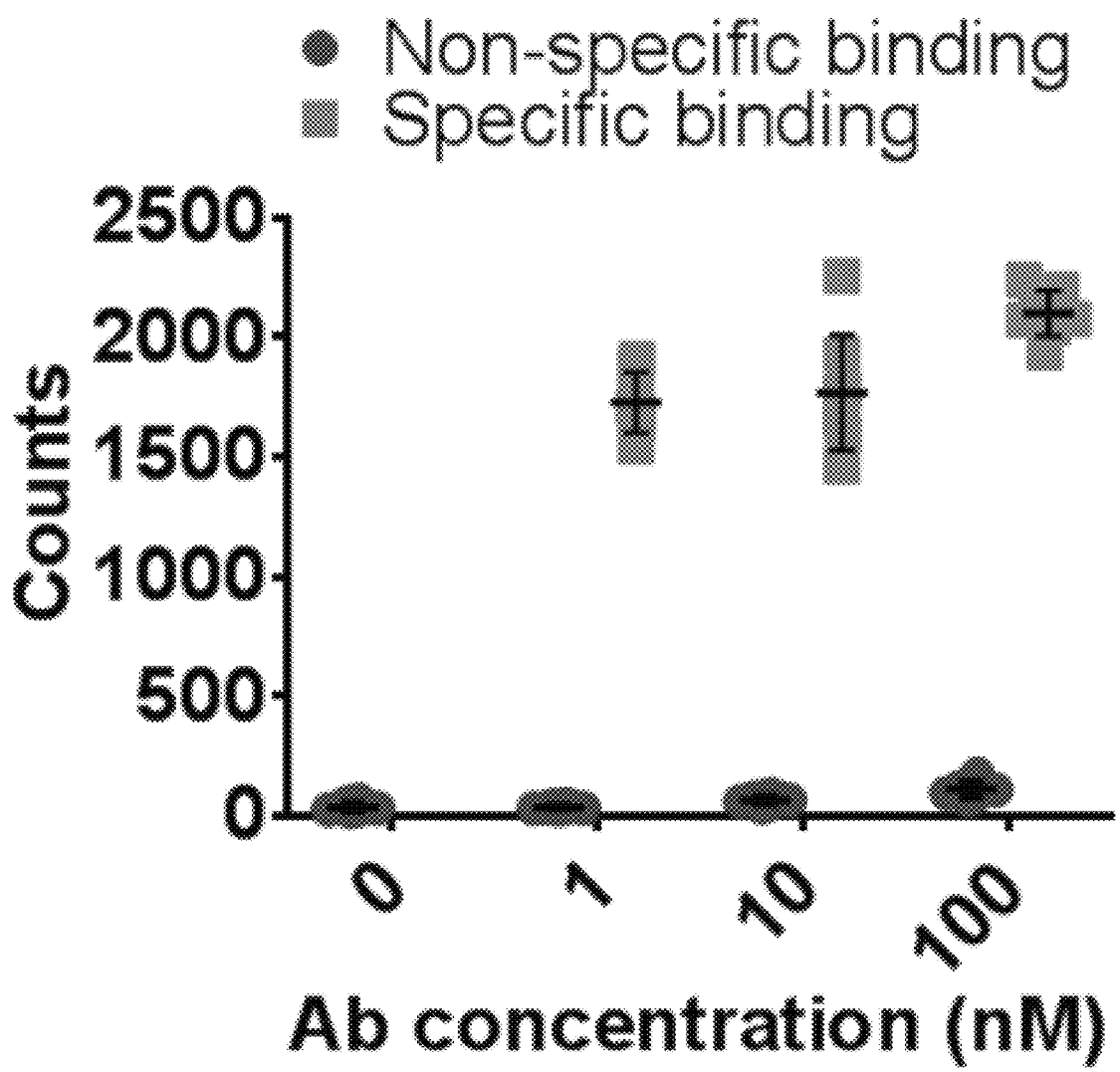
FIG. 4 Chip surface chemistry enables efficient target capture with negligible background and non-specific binding. Microfluidic chips conjugated with α-p53 Ab were incubated with or without p53 (1 pM) under continuous circulation (700 μl/min flow rate) actuated via a peristaltic pump. Chips were incubated with various concentrations of fluorescence-labeled α-p53 detection Ab, visualized by SMAC, and p53 spots were measured.

The fundamental innovations behind the SMAC platform are illustrated in FIG. 1. SMAC technology achieves detection sensitivity at the single-molecule level and is vastly superior to ELISA-based methods for multiple reasons. First, SMAC does not rely on any biochemical signal amplification steps, thereby circumventing the background levels inherent in ELISA. Second, SMAC utilizes a specially designed microfluidic chip that may be based on staggered herringbone geometry (FIG. 2) (or incorporate other types of active and/or passive micromixers) and a 2 step-coated glass imaging surface that permits efficient capture of target proteins with extremely low non-specific adsorption of proteins (FIG. 3 and FIG. 4). Because of bonding constraints, state-of-the-art methods are currently incapable of producing microfluidic devices with precise (m resolution) geometry that also exhibit the extremely low levels of background and non-specific surface binding required for single molecule imaging. Thus, in order to create this type of chip, the inventors engineered an entirely new way of bonding microfluidic devices. Conventional methods for bonding microfluidic devices require harsh conditions (such as exposure to atmospheric or oxygen plasma followed by high temperature) and are incompatible with coated substrates (FIG. 27 and FIG. 29). As a result, single molecule imaging on coated glass is currently performed in flow chambers sealed by adhesives (e.g. tape or epoxy). These bonding methods, however, are prone to leakage under prolonged, high velocity flow and, critically, suffer from lack of precise control over chip size and shape. The inventors' unique bonding technique utilizes a fine elastomer fabricated to the exact dimensions of the SMAC chip flow channel; this elastomer serves as a cover that protects the coated substrate from the destructive effects of oxygen plasma. With this technique, the inventors have achieved rapid (~3 min bonding time), high-resolution (m scale), covalent bonding of microfluidic devices without altering the coated surface in any way.

Figure 5:
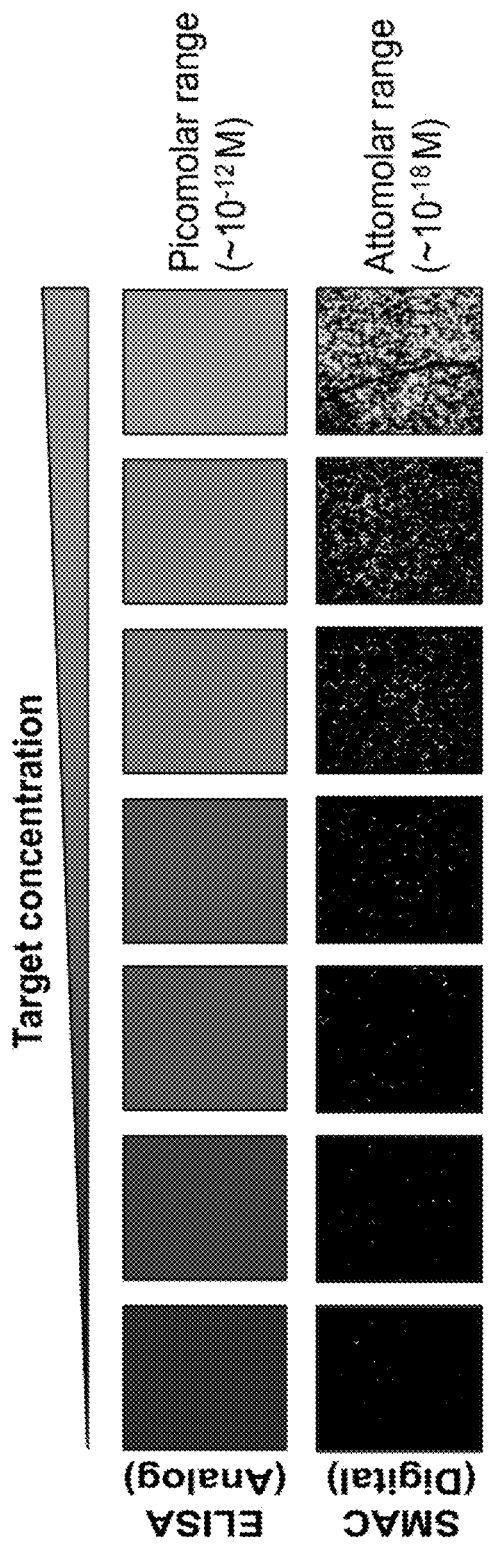
FIG. 5 SMAC provides digital information about the spatial positions of target proteins. Conventional methods such as ELISA produce an ensemble readout of target concentration and typically have a detection limit in the $10^{-12}$ M range. By contrast, SMAC provides spatial and stoichiometric information about individual target proteins via digital analysis and has a detection limit in the $10^{-18}$ M range. By processing this spatial information through an algorithm, we can discriminate between on-target and off-target binding events, thereby solving the problem of non-specific binding.
Figure 6:
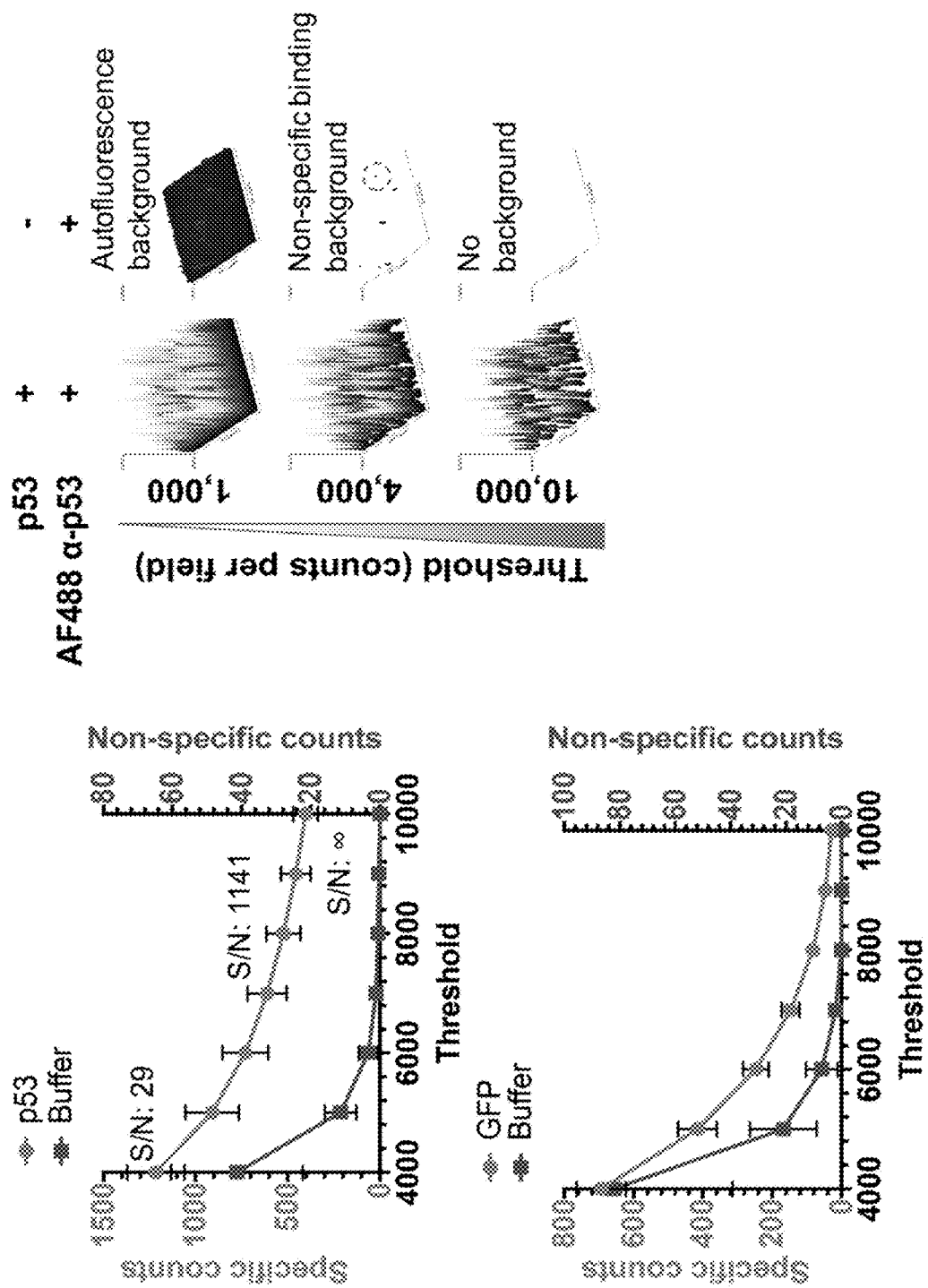
FIG. 6 Specific and non-specific protein binding levels as a function of analysis threshold. SMAC chips conjugated with α-p53 Ab were incubated with or without p53 (1 pM) or GFP (100 fM) under continuous circulation. Samples were probed for p53 or GFP and then examined by single molecule imaging. The number of p53 or GFP protein counts per imaging field was quantified at various absolute threshold values (no signal processing filter applied). Our data indicate exponential decay at similar rates for GFP and buffer fluorescence as the threshold is increased. By contrast, in the p53 system, signal decay in the buffer group was much more rapid than that in the p53 group, because multiple polyclonal p53 detection Ab can cluster around a single p53 molecule. However, the probability of detection Ab aggregation in the absence of p53 is extremely low. Therefore, this analysis method allows us to discriminate between on-target and off-target protein detection. With threshold values >7,000 we could achieve signal: noise ratios approaching infinity even for very low protein concentrations (fM range).
Figure 7:
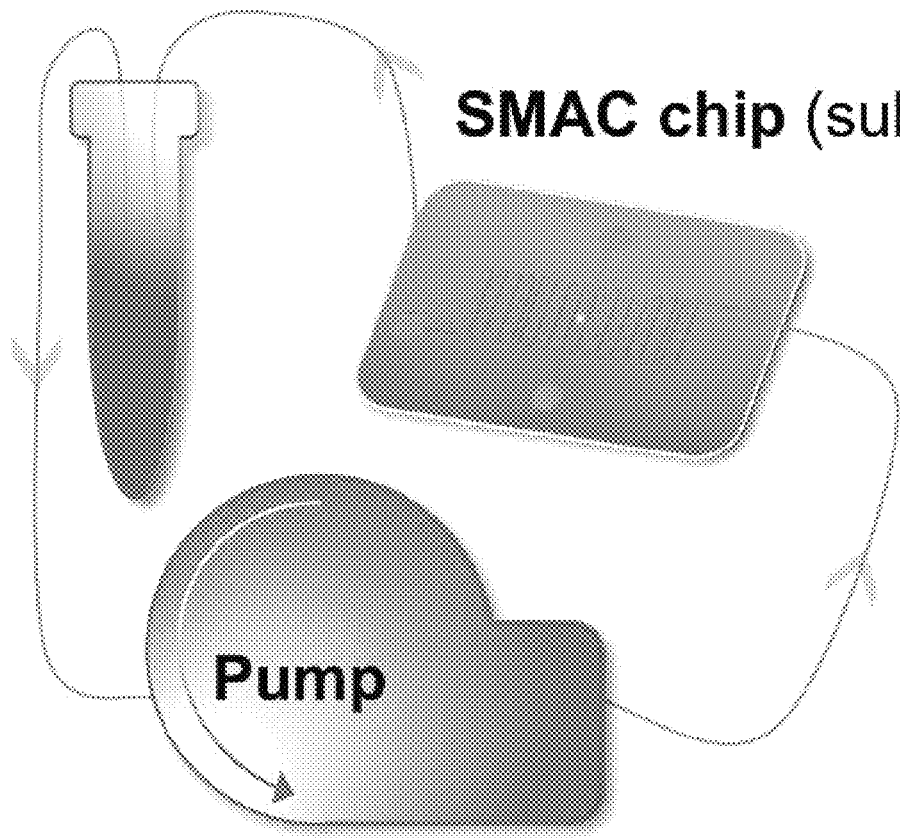
FIG. 7 Schematic diagram of the circulation system. Automated, closed-loop circulation from the sample through the SMAC chip is actuated by a pump (e.g., peristaltic, syringe, pneumatic type). Circulation may be set up in a positive pressure (shown) or negative pressure loop. The circulation system can accommodate flow rates from <1 μl/min to >1 ml/min, with an optimal range of 500-800 μl/min for protein capture.
Figure 8:
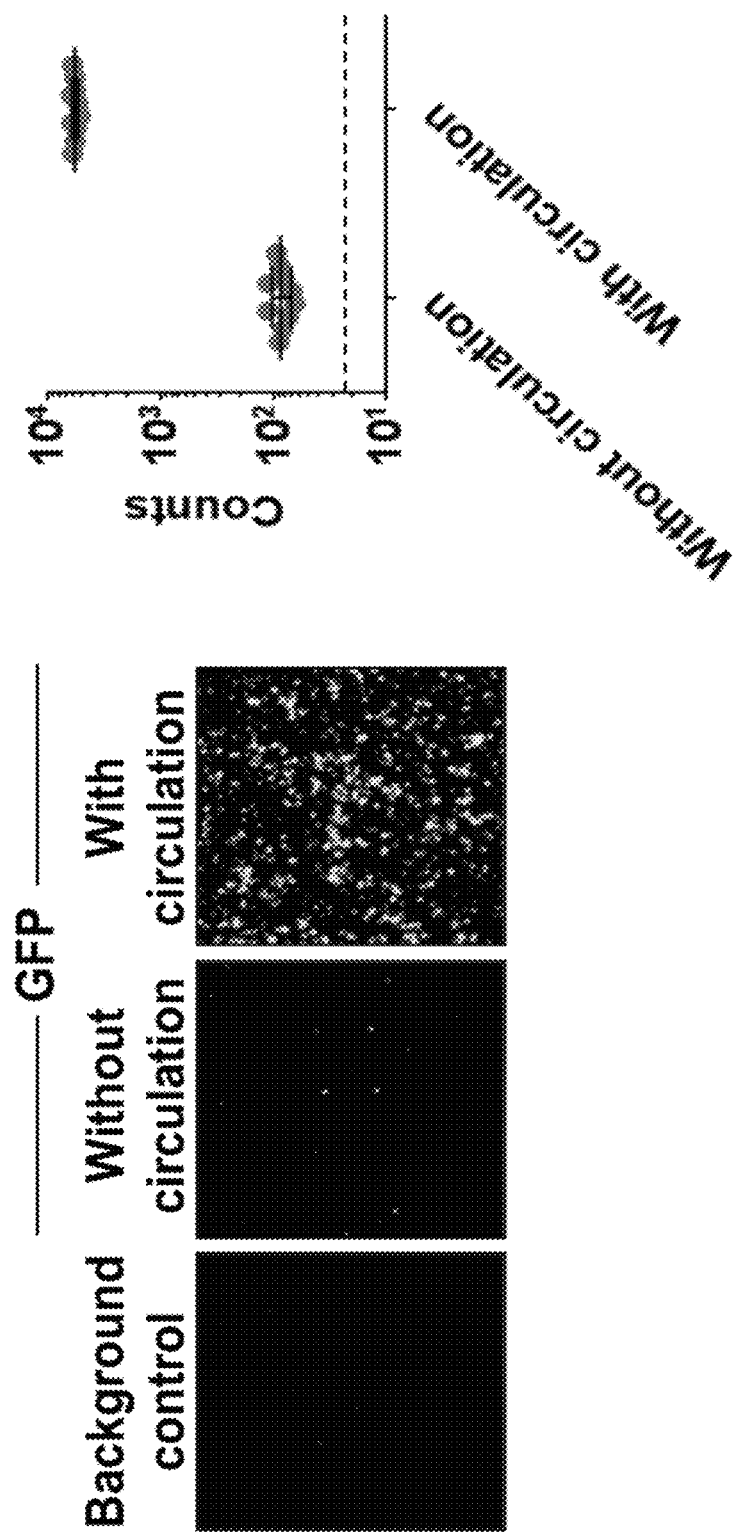
FIG. 8 Target molecule concentration by the circulation system. SMAC chips conjugated with α-GFP mAb were incubated with GFP for 30 min either with or without continuous circulation (700 μl/min flow rate) actuated via a peristaltic pump. Chips were visualized by SMAC and GFP spots were measured. Left: Representative SMAC micrographs. Right: The incorporation of a circulation system improves target capture by >100-fold. The dashed line depicts the noise floor (i.e. counts due to background autofluorescence).
Figure 9:
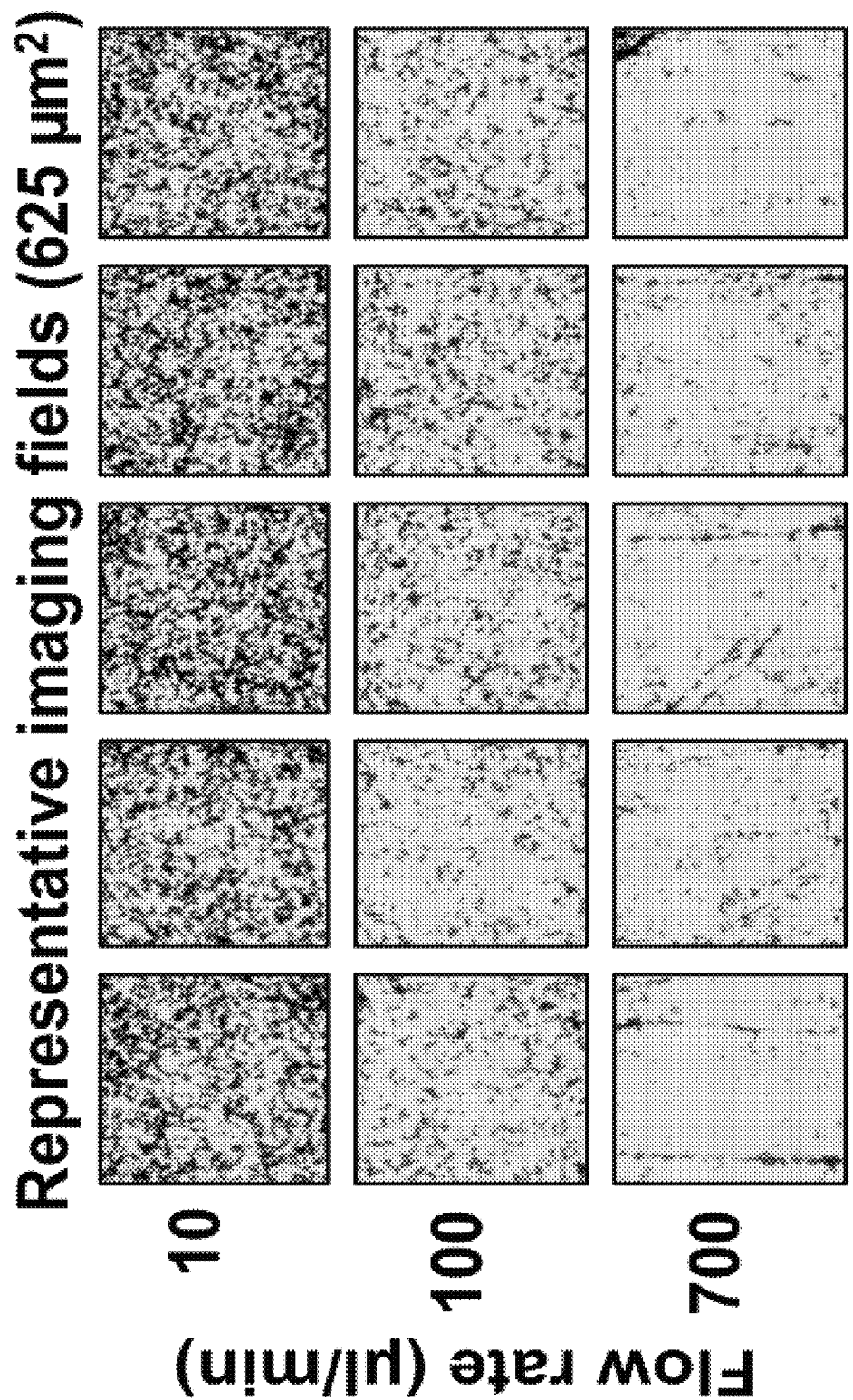
FIG. 9 Effect of flow rate on target capture and detection. Microfluidic chips conjugated with α-GFP mAb were incubated with GFP (1 pM) for 2 hr under closed-loop circulation with various flow rates (10, 100, or 700 μl/min). Chips were visualized by SMAC to compare target capture/detection under different flow rates.

Third, because SMAC can visualize individual proteins in space (FIG. 5), the inventors have been able to develop a digital molecule counting algorithm that accurately discriminates between on-target and off-target detection (FIG. 6). Together, these innovations eliminate the problem of non-specific detection reagent binding that plagues virtually all other detection methods. Finally, because of integration with an automated circulation system (FIG. 7), SMAC can rapidly concentrate rare target proteins in large sample volumes by >$10^4$-fold, down to sub-μl volumes (FIG. 8 and FIG. 9).

Figure 10:
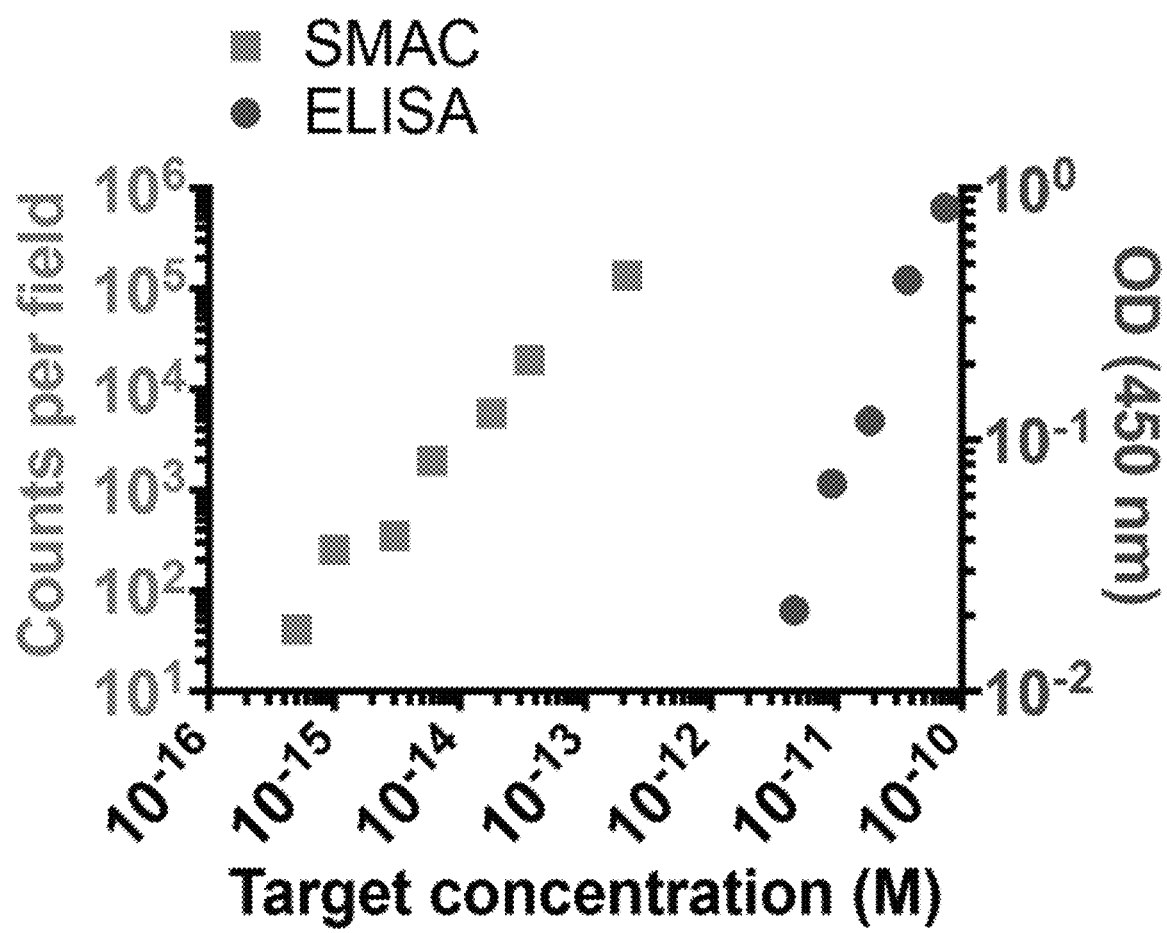
FIG. 10 Comparison of protein detection by SMAC or ELISA. SMAC chips conjugated with α-GFP mAb were incubated with recombinant GFP at various doses (from 0.5 fM to 216 fM) under continuous circulation. GFP was quantified by single-molecule imaging and presented as average background subtracted counts per field (n=10). SMAC counts scaled linearly with GFP concentration ($R^2$=0.9987). The imaging field was saturated at >300 fM GFP. For comparison, GFP ELISA was performed with a commercial kit (Cell Biolabs, Inc.). ELISA OD values also scaled linearly with GFP concentration ($R^2$=0.9893). The detection limit for SMAC was <0.5 fM GFP, while that for ELISA was ~10 pM GFP. Our data indicate that, relative to ELISA, SMAC is over 20,000 times more sensitive and covers a 100-fold wider dynamic range. We have obtained similar data for other target proteins.
Figure 11:
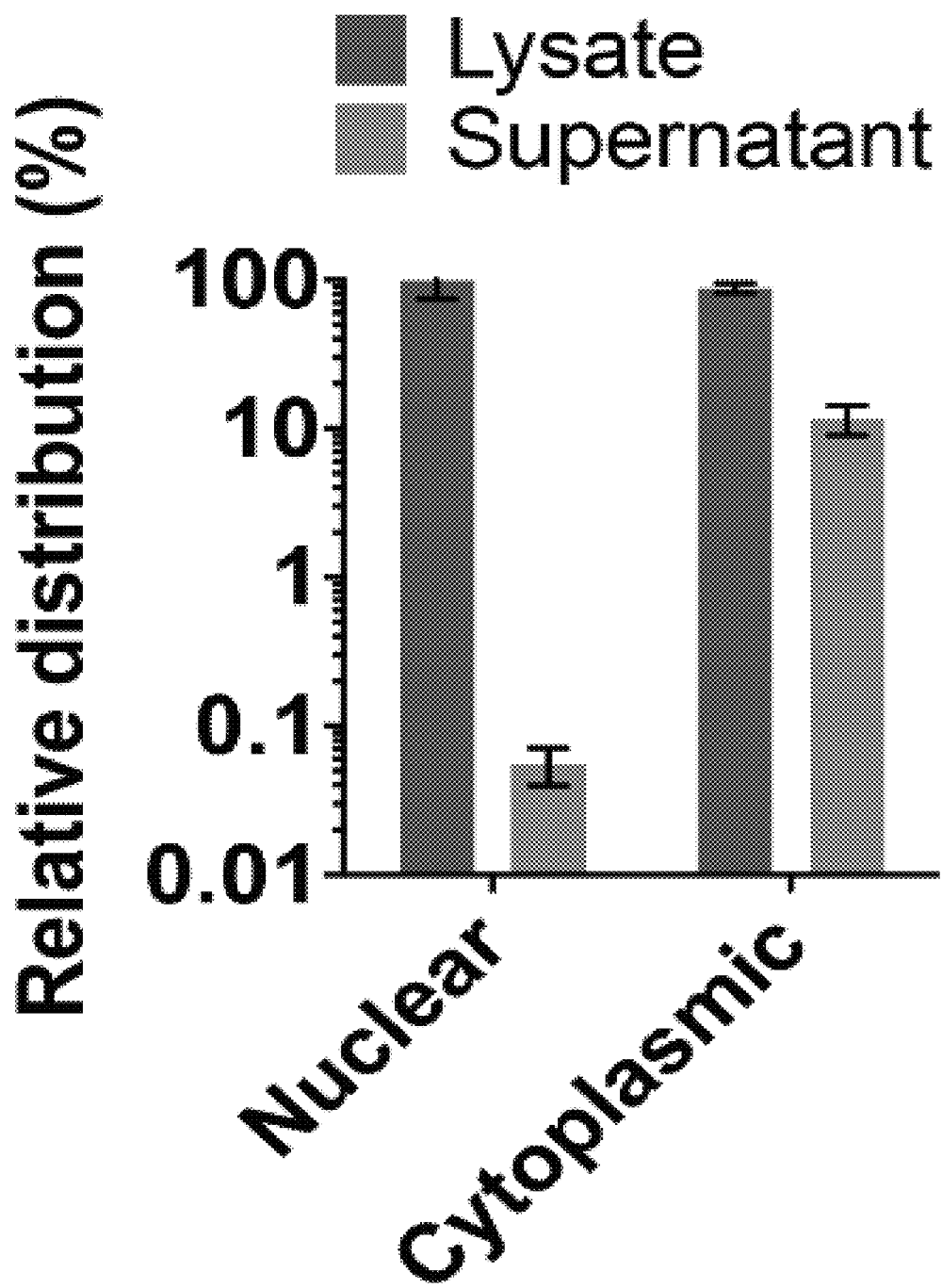
FIG. 11 SMAC reveals the steady-state leakage of nuclear and cytoplasmic proteins from tumor cells into their surrounding environment. Lysate or filtered supernatant from TC-1 tumor cells carrying cytoplasmic (GFP) or nuclear (GFP-p53) proteins was passed through α-GFP mAb-conjugated microfluidic chips and then visualized by SMAC. (A) Representative SMAC micrographs from lysate, filtered supernatant, or medium control. (B) Relative percentage of nuclear/cytoplasmic proteins inside (lysate) or released outside (supernatant) of the cells. Note: despite the miniscule percentage of nuclear proteins that are ultimately released outside of tumor cells, due to the exquisite sensitivity of SMAC, the fluorescence signal from these nuclear proteins in the supernatant is still >2×10$^6$-fold higher than background autofluorescence from culture medium.
Figures 12A, 12B:
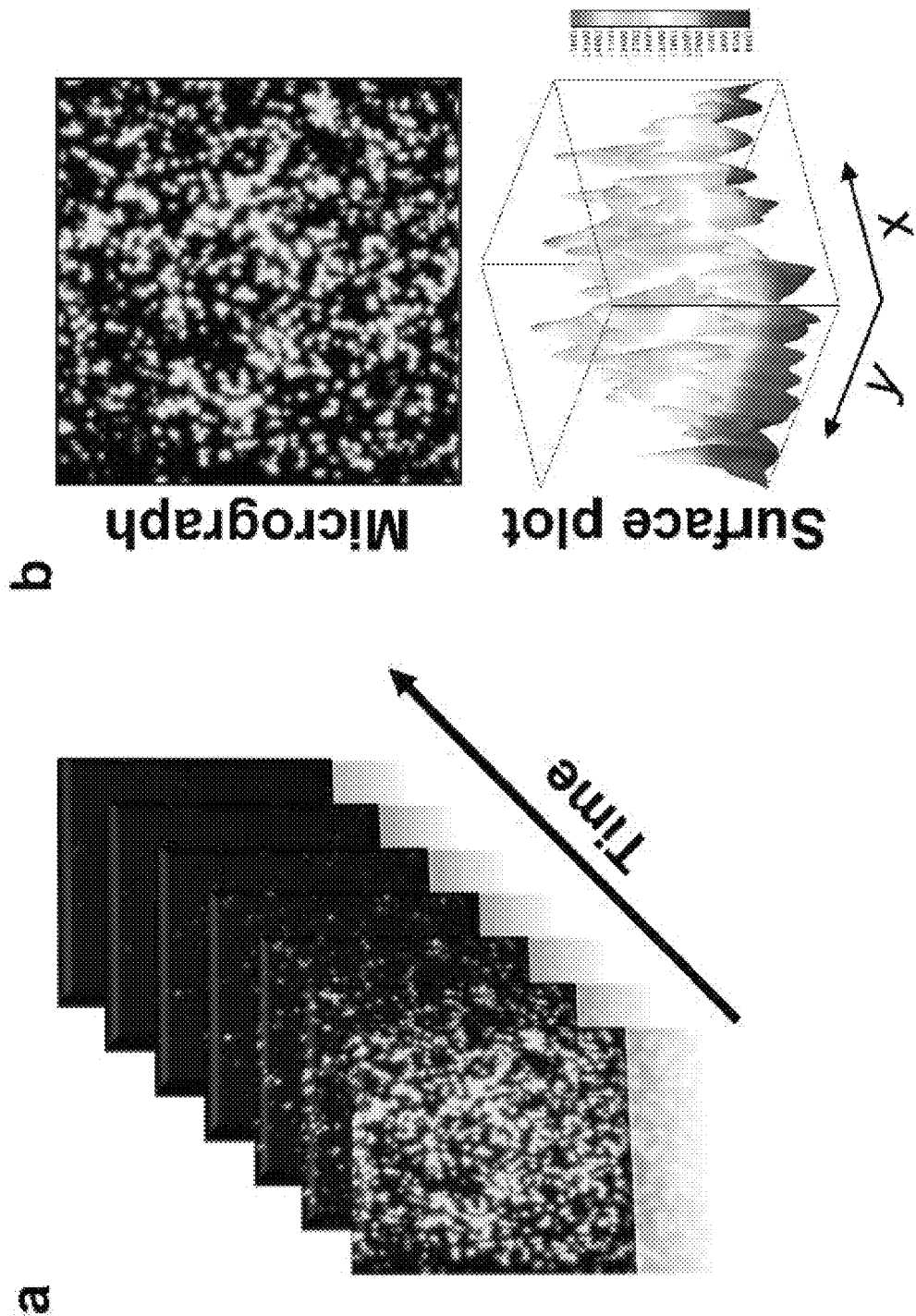
FIG. 12A-12B SMAC analysis of p53 escape from human ovarian cancer cells. (A) Filtered supernatant from human ovarian cancer cells (OVCAR3) was passed through α-p53 Ab-conjugated SMAC chips and then visualized by time-lapse single molecule imaging (500 frames, 50 ms exposure time). (B) Representative SMAC micrograph (top) and surface plot (bottom) are shown. Note: p53 is released at levels too low to be appreciated by conventional techniques such as ELISA or Western blot.

The inventors have found that SMAC has unparalleled sensitivity, with a detection limit in the attomolar (aM) range, >10,000-fold superior to ELISA-based methods (FIG. 10). The exceptionally high sensitivity of SMAC allowed the inventors to ask whether tumor-specific nucleocytoplasmic proteins are released from tumor cells into their surrounding environment. The inventors determined by SMAC that, in general, ~1-10% of cytoplasmic proteins and ~0.1% of nuclear proteins are released from tumor cells into their surrounding environment at steady state (FIG. 11). The inventors also observed the escape of mutant p53 from human ovarian cancer cells (OVCAR3) into the environment (FIG. 12). Notably, the trace levels of nuclear proteins released in vitro have been invisible to conventional detection method.

Figure 13:
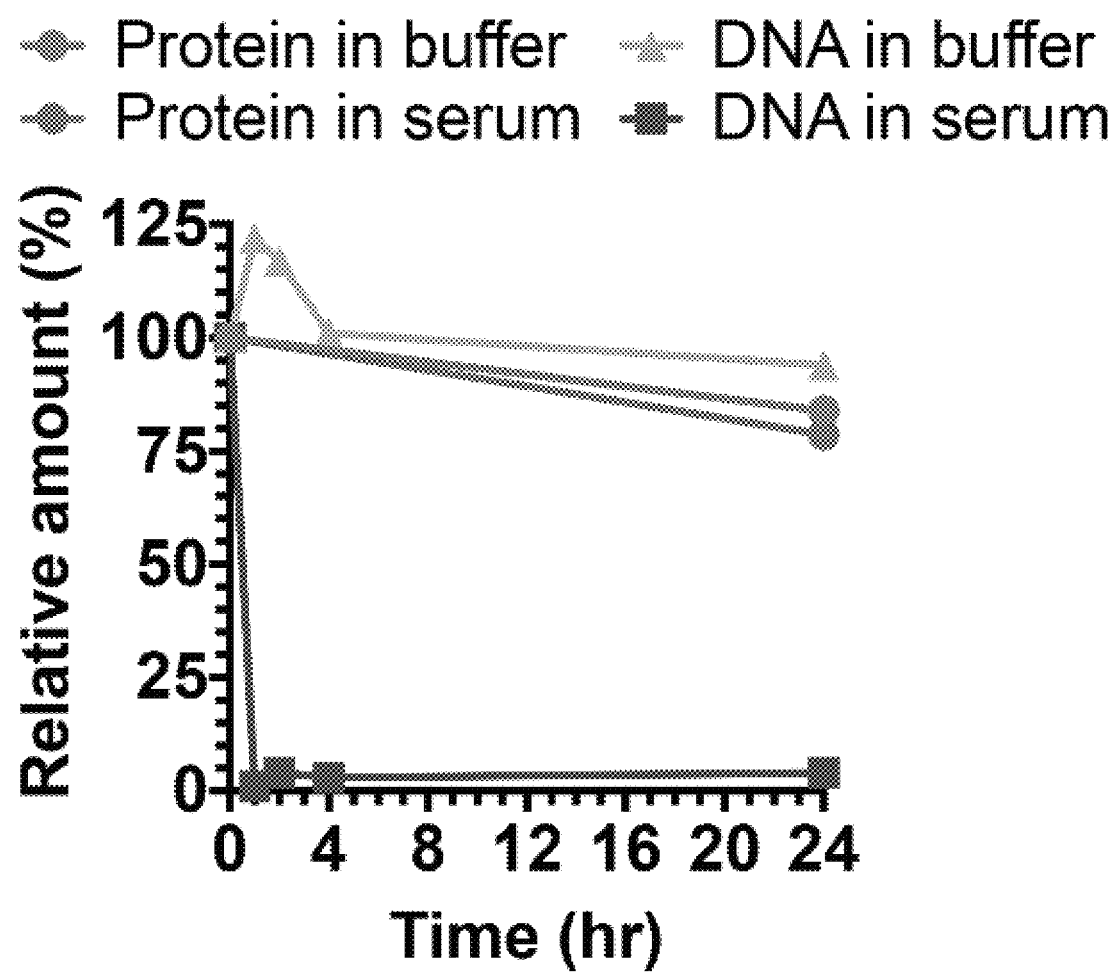
FIG. 13 Comparison of protein versus DNA stability in serum. The same amount ($5 \times 10^5$ copies) of purified GFP protein or plasmid DNA was spiked into Tris buffer pH 7.4 or mouse serum and incubated at 37° C. At the indicated time points, the amount of corresponding protein or DNA remaining in the samples was measured by SMAC or qPCR, respectively. Our data indicate that in serum the half-life of GFP protein is ~60 hr, while that of GFP DNA is only a few min. We found that this trend holds in general for nucleocytoplasmic proteins including p53.

The inventors' discovery that nucleocytoplasmic proteins are released from tumor cells into their surrounding environment raises the intriguing prospect that a fraction of these proteins may also end up in the systemic circulation. The inventors believe that SMAC detection of released nucleocytoplasmic tumor-specific proteins opens a path to early cancer detection-even more so than PCR detection of tumor-specific DNA because proteins are in principle are much more abundant in the blood than their template DNA. To explore this idea, the inventors spiked an equal amount of GFP proteins and DNA into either Tris buffer or mouse serum and measured their levels by SMAC or qPCR, respectively, at different time points after incubation at 37° C. While >80% of GFP proteins remained after 24 hr, only 1% of GFP DNA remained after just 1 hr in serum (FIG. 13). The inventors found this trend to be consistent among different nucleocytoplasmic proteins. The exceptionally labile nature of DNA in the blood (10 min half-life) has also been documented in vivo. Thus, the inventors' data indicate that proteins are 100-1,000× more stable than their corresponding DNA in the circulation.

Figures 14A, 14B:
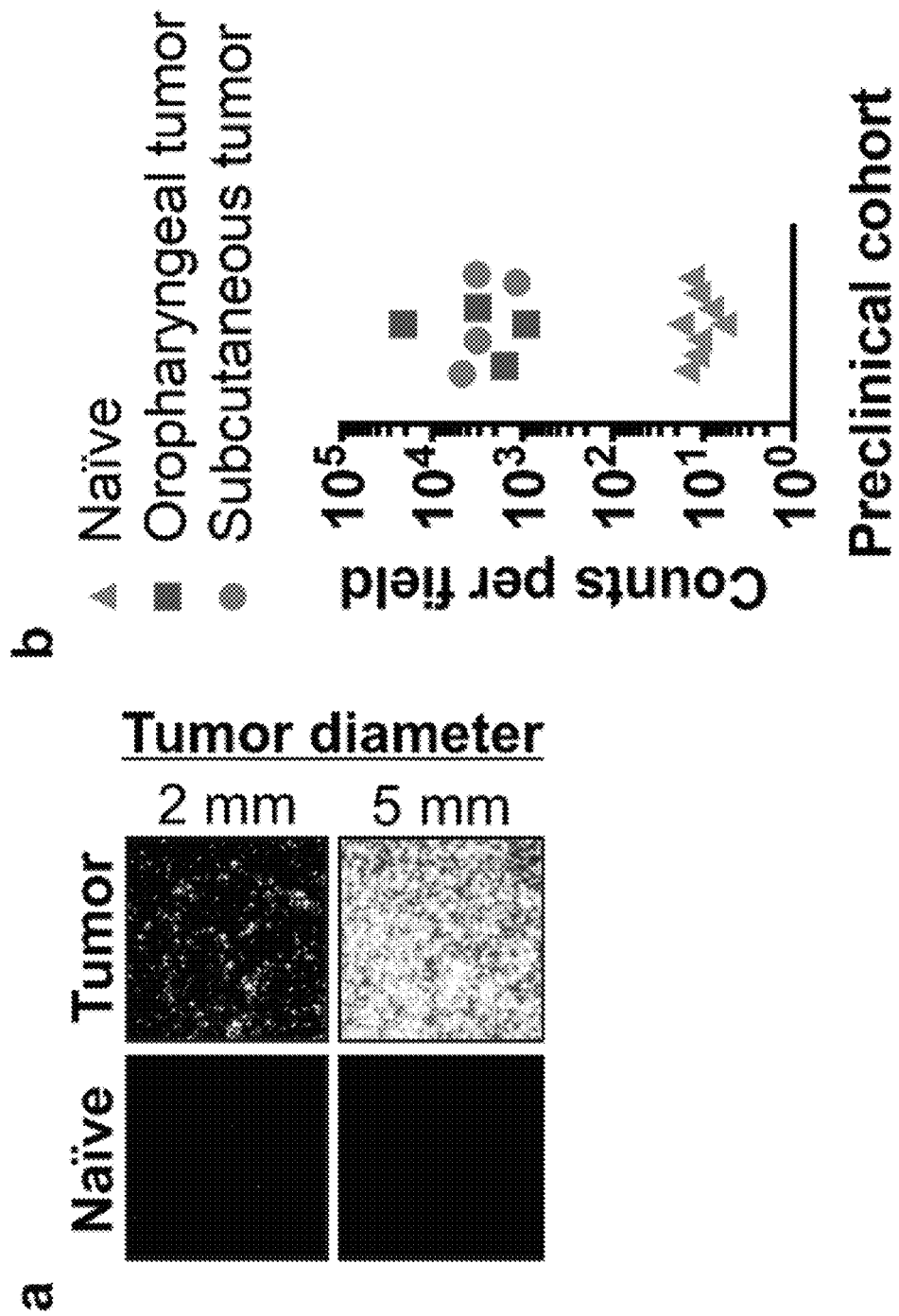
FIG. 14A-14B SMAC reveals the escape of nucleocytoplasmic proteins from tumor cells into the systemic circulation. (A) A discovery cohort of $Rag^{-/-}$ mice were inoculated with cytoplasmic $GFP^+$ TC-1 tumor cells by subcutaneous injection. Serum was collected from naïve or tumor-bearing mice at 7 or 14 days, when the tumor was 2 or 5 mm in diameter, respectively, and examined for GFP by SMAC. (B) Validation experiments were performed in mice that received either subcutaneous or oropharyngeal challenge with cytoplasmic $GFP^+$ TC-1 cells. Serum GFP was quantified by SMAC 14 days after tumor challenge. Note: Serum GFP levels in all tumor-bearing mice were 100-1,000× above background levels in naïve mice. These serum GFP levels, however, fall below the ELISA detection limit.

To test whether tumor-specific nucleocytoplasmic proteins are released into the circulation, the inventors administered $Rag^{-/-}$ mice with TC-1 tumor cells carrying cytoplasmic GFP by subcutaneous or oropharyngeal injection (to simulate $HPV^+$ oropharyngeal cancer). At 14 days after tumor challenge, when the tumor was 3-5 mm diameter, the inventors found by SMAC that serum GFP counts in tumor-bearing mice were >100-1,000× higher than background fluorescence in naïve control mice (FIG. 14a, b), demonstrating escape of tumor-specific nucleocytoplasmic proteins into the peripheral circulation. Notably though, the levels of these systemic nucleocytoplasmic proteins still fall >100-fold below the ELISA detection limit (FIG. 10), highlighting the need for SMAC technology.

Figures 15A, 15B, 15C:
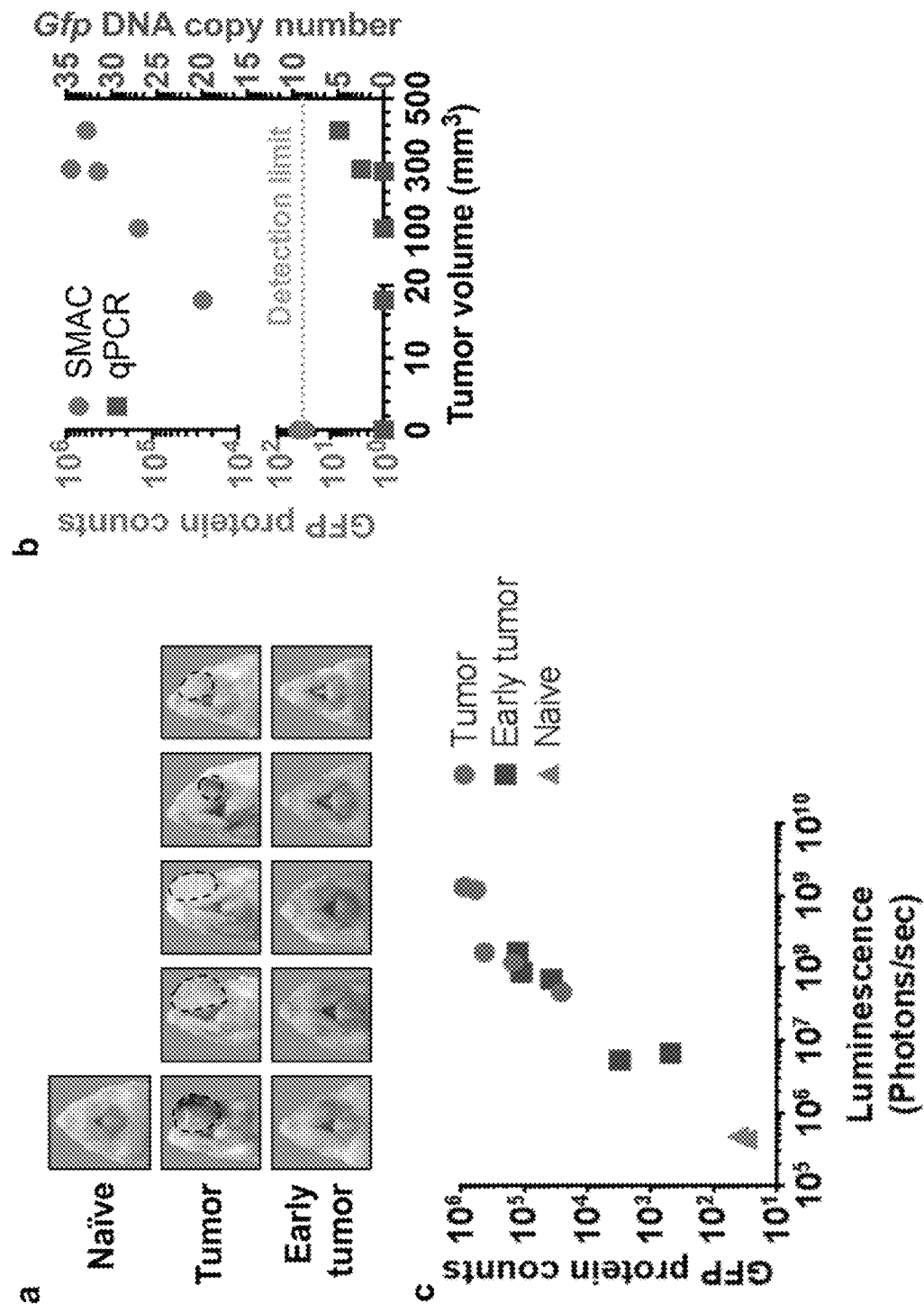
FIG. 15A-15C Non-invasive early cancer detection by SMAC in a pre-clinical tumor model. Athymic nude mice received buccal electroporation with $Ras^{G12V}$, shP53-Gfp, and Sb13-Luciferase transposase to induce spontaneous tumor formation. In this model, the tumor becomes appreciable ~8-10 wk after electroporation. (A) Digital photographs of mice with well-established tumor (readily visible and palpable) (n=5) or early-stage tumor (not visible but appreciable by luminescence imaging) (n=5). (B) Serum was collected from mice with well-established tumor and examined for GFP protein or DNA by SMAC or qPCR, respectively. (C) Serum GFP SMAC counts were correlated with buccal luminescence in naïve mice or mice with either well-established or early-stage tumor.

Because only a minor fraction of nucleocytoplasmic tumor-derived proteins is released into the circulation, the inventors wondered: (1) how early in the course of cancer progression could we identify these nucleocytoplasmic markers in the circulation by SMAC, and (2) how SMAC detection of tumor-derived nucleocytoplasmic proteins stacks up against qPCR detection of the corresponding DNA. To address these issues, the inventors adopted a spontaneous preclinical model of oropharyngeal cancer recently developed in our laboratory, based on the Sleeping Beauty (SB) transposase system (FIG. 15a). In this model, in vivo transformation is induced by buccal electroporation with DNA encoding $Ras^{G12V}$ and shP53-Gfp; the emergent tumor cells carry a luciferase expression cassette (for non-invasive monitoring of disease progression by luminescence imaging), together with cytoplasmic GFP, which allows us to trace the escape of tumor-derived nucleocytoplasmic proteins. At 8 wk after electroporation into athymic nude mice, the inventors observed serum GFP counts by SMAC at >100-1,000× above background counts in serum from naïve mice (but again far below the ELISA detection limit ((FIG. 10)), which increased as an exponential function with tumor volume (FIG. 15b). Remarkably, even an animal with a very small tumor (<20 mm³ volume) had serum GFP counts of >100-fold above background (FIG. 15b). Furthermore, mice with early stage tumor—defined as the presence of buccal luminescence without overt clinical signs—had readily appreciable serum GFP which scaled linearly with buccal luciferase intensity (FIG. 15c). By contrast, serum GFP DNA was below the real-time qPCR detection limit (~10 GFP DNA copies) until the tumor reached a large size (~500 mm³) (FIG. 15b). These minute levels of tumor-specific DNA in the circulation in mice are consistent with the literature. Therefore, the inventors conclude that: (1) SMAC can readily identify established cancer, even when the tumor size is very small, and (2) the serum levels of tumor-derived nucleocytoplasmic proteins exceeds that of the corresponding DNA by nearly $10^6$-fold.

Figure 16:
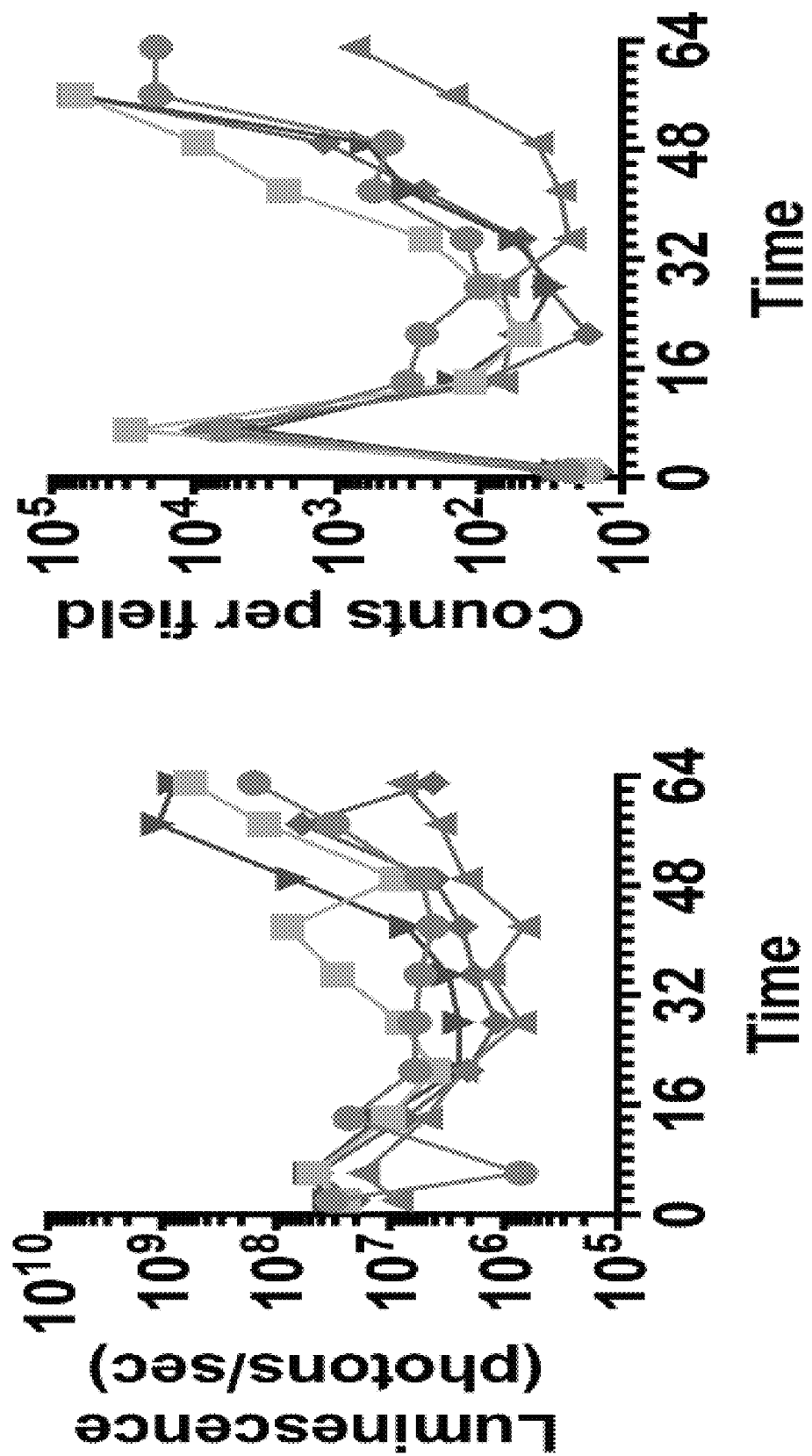
FIG. 16 Tracing the release kinetics of nucleocytoplasmic proteins from tumor cells into the circulation by SMAC. Athymic nude mice (n=5) received buccal electroporation with $Ras^{G12V}$ shP53-Gfp, and Sb13-Luciferase transposase to induce spontaneous tumor formation. Buccal luciferase intensity (left) and serum GFP levels (right) were measured over time by SMAC and non-invasive luminescence imaging, respectively. Note: for each animal, an exponential increase in serum GFP was observed by SMAC ~2 wk before any change was observed in buccal luminescence, indicating that SMAC is capable of detecting early transformation events in cancer onset.

The inventors next examined the kinetics of escape into the circulation for tumor-specific nucleocytoplasmic proteins in relationship to tumor progression in a separate cohort of mice that received $Ras^{G12V}$ shP53-Gfp electroporation. The inventors observed a spike in serum GFP by SMAC within the first several days after electroporation (due to transient transfection of buccal cells) (FIG. 16). Notably, serum GFP levels started to rise sharply around 5 wk after electroporation, prior to the appearance of a visible tumor, and ~3 wk before any increase in buccal luciferase activity could be measured by luminescence imaging (FIG. 16), indicating the detection of cancer at the early onset of oncogenic transformation. Altogether, the inventors' preliminary data demonstrate the SMAC detection of cancer, even at early stage, with 100% sensitivity and specificity.

Figures 17A, 17B:
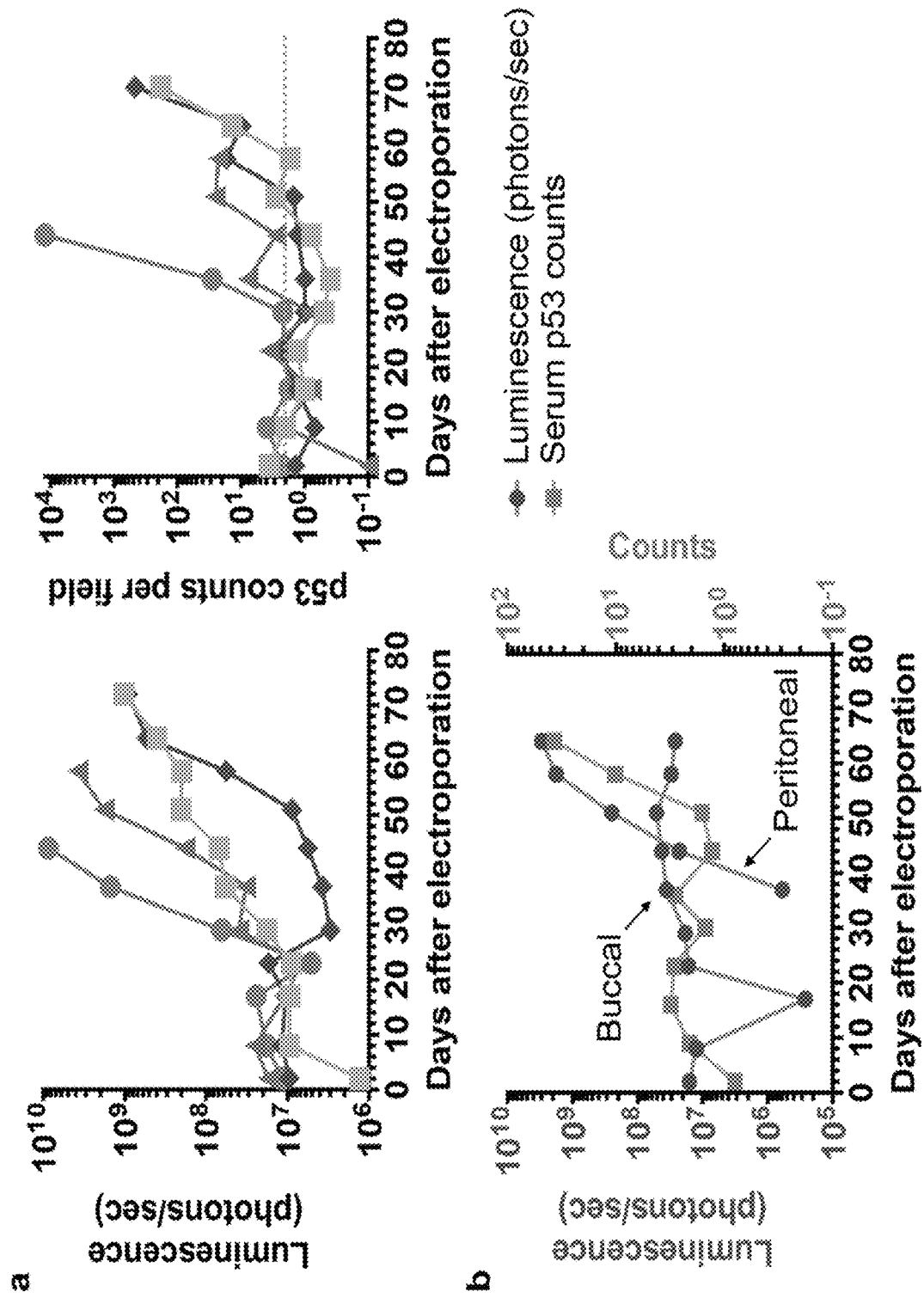
FIG. 17A-17B Non-invasive detection of p53 by SMAC in a pre-clinical tumor model. Athymic nude mice received buccal electroporation with $Ras^{G12V}$, $p53^{R172H}$ and Sb13-Luciferase transposase to induce spontaneous tumor formation. (A) Buccal luciferase intensity (left) and serum p53 levels (right) were measured over time by SMAC and non-invasive luminescence imaging, respectively. Gray dotted line depicts SMAC detection limit. (B) A representative animal from the cohort described above presented with a peritoneal metastasis without a buccal primary tumor. By p53 SMAC, we could readily monitor the emergence of metastasis in this animal.
Figure 18:
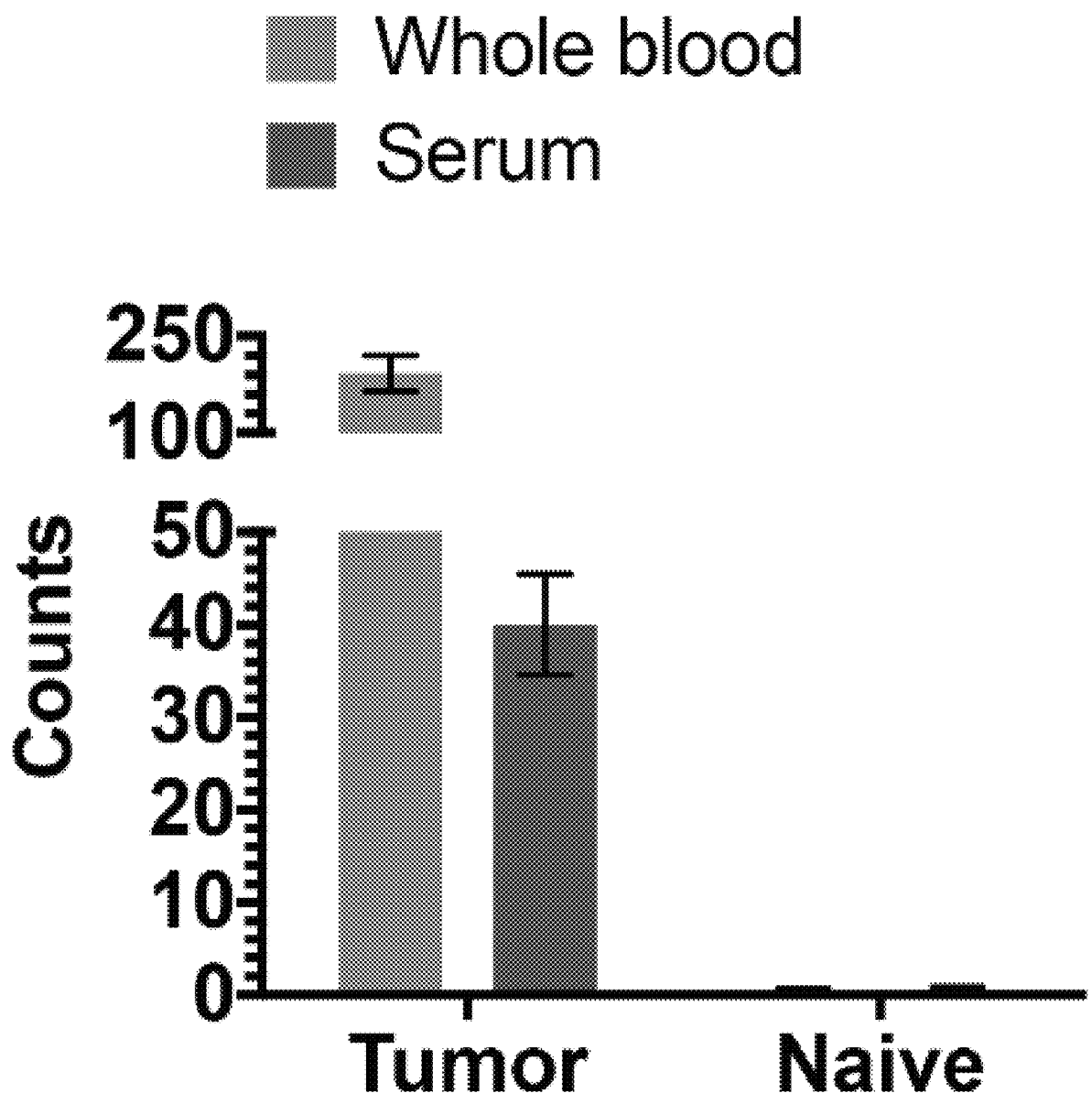
FIG. 18 SMAC detection of p53 in whole blood of tumor-bearing mice. Athymic nude mice received buccal electroporation with $Ras^{G12V}$, shP53-Gfp, and Sb13-Luciferase transposase to induce spontaneous tumor formation. Whole blood or serum was collected from mice that received electroporation or from naïve control mice, and p53 levels were measured by SMAC.

To extend the inventors' results to a clinically relevant scenario, the inventors performed analysis for mutant p53 in the blood by SMAC. The inventors chose the p53 transcription factor for the following reasons: (1) it is extremely unstable in the wildtype form and thus undetectable in normal tissue; (2) it is found in mutant form in most human cancer cases, including over 96% of high grade serous ovarian cancer cases; and (3) the mutant form is an essential driver of cancer onset and progression and has a markedly prolonged half-life compared to the wildtype form. The inventors have observed that p53 is released at steady state from human ovarian cancer cells (FIG. 12). To study p53 escape into the circulation, the inventors employed the SB transposase-luciferase spontaneous oropharyngeal tumor model described above; tumor formation was induced by $Ras^{G12V}$ and $p53^{R172H}$. In this model, tumor formation occurs ~6-7 wk after oncogene electroporation and can be seen by an increase in buccal luminescence (FIG. 17a). At around the same time as this luminescence increase, the inventors found an exponential rise in serum p53 by SMAC in all mice that received electroporation (FIG. 17a). The presence of a tumor could also be traced by SMAC analysis of p53 in whole blood (FIG. 18). Because SMAC can be broadly applied in multiple types of complex biological matrices, even unprocessed whole blood, it is well-suited for rapid, non-invasive disease detection and diagnosis. Furthermore, in the $p53^{R172H}$ spontaneous tumor model, mice develop peritoneal metastasis with ~20% frequency. The emergence of peritoneal metastasis coincided with a sharp rise in serum p53 (FIG. 17b). Therefore, the SMAC system may be applied for both early cancer detection and monitoring of cancer progression and metastasis.

Figure 19:
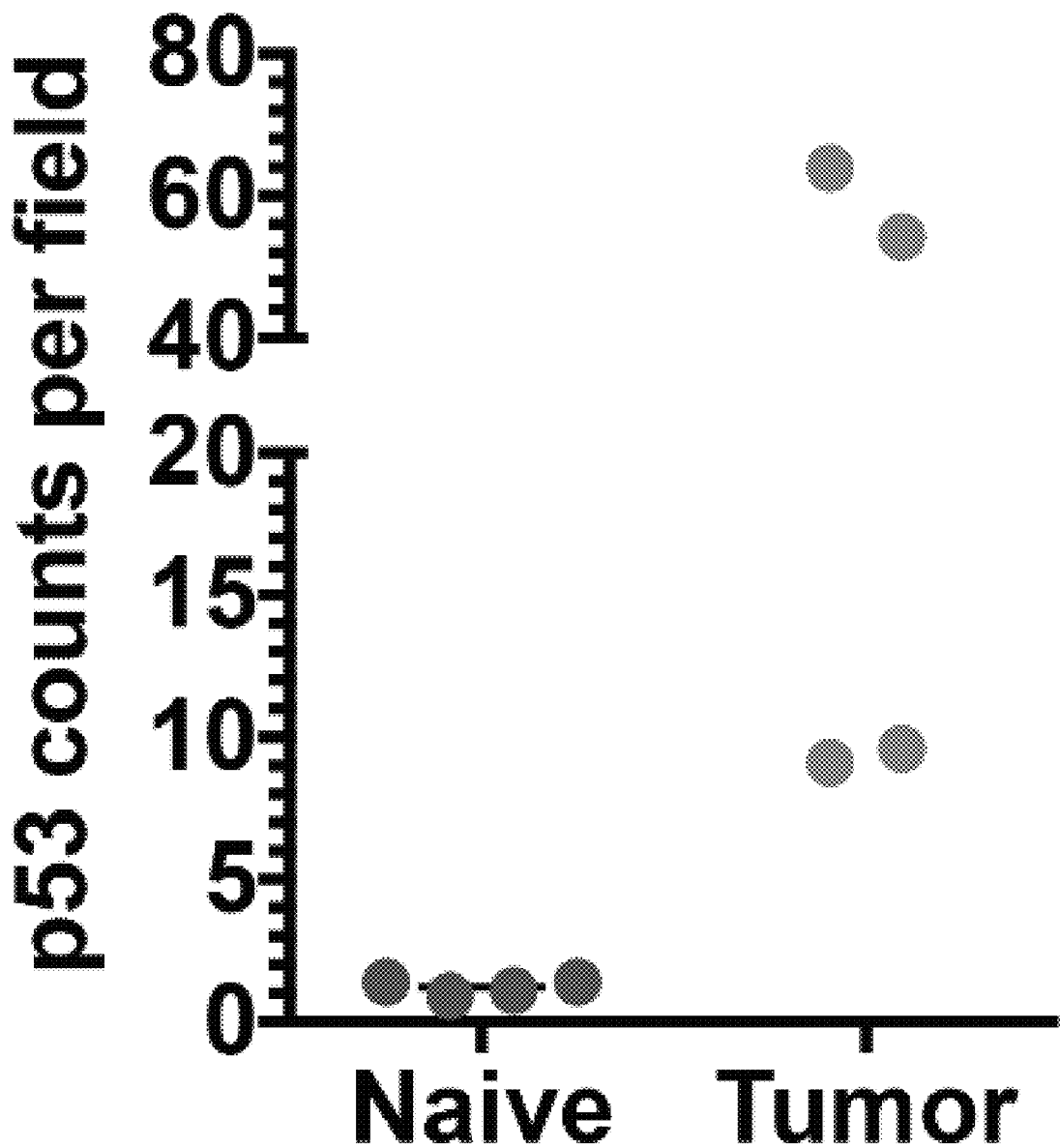
FIG. 19 Non-invasive early stage detection of human ovarian cancer in a xenograft preclinical model. Athymic nude mice were inoculated with OVCAR3 human ovarian cancer cells by intraperitoneal injection. 2 days after tumor challenge, blood was collected and examined for p53 by SMAC. Naïve nude mice served as control. The data indicate that SMAC could identify early stage ovarian cancer with 100% sensitivity and specificity in this preclinical model.

To study p53 escape in a human tumor model, the inventors inoculated athymic nude mice intraperitoneally with OVCAR3 human ovarian cancer cells, which carry mutant $p53^{R248Q}$. After 2 days, before any clinical signs were apparent, the inventors probed the serum of these mice for mutant p53. The inventors observed p53 in the serum of all tumor-bearing mice but in none of the naïve mice (FIG. 19). Therefore, altogether these preclinical data demonstrate early stage, non-invasive SMAC detection of cancer with 100% sensitivity and specificity by analysis of tumor-specific nucleocytoplasmic proteins.

Figure 20:
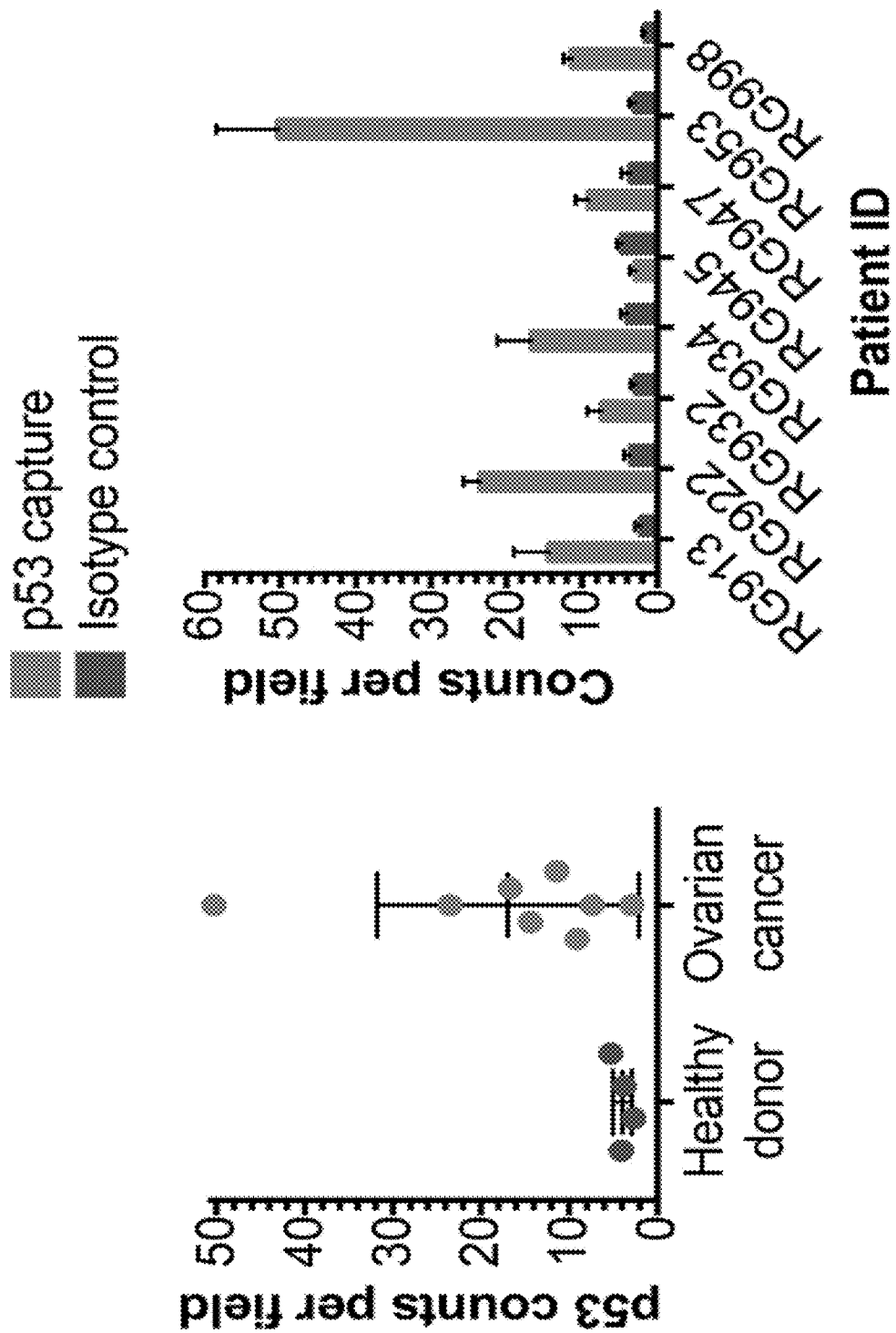
FIG. 20 SMAC analysis of p53 in the circulation of ovarian cancer patients. Plasma samples from healthy donors (n=4) or ovarian cancer patients (n=8) were examined for p53 by SMAC. Left: quantification of plasma p53 levels in healthy donors versus ovarian cancer patients. Right: for each ovarian cancer patient, plasma samples were passed through SMAC chips conjugated with either α-p53 Ab (red bar) or isotype control (blue bar) and then probed with fluorophore-labeled α-p53 detection Ab. Fluorescence counts per field are presented.

The inventors next performed SMAC blood analysis of mutant p53 in a cohort of ovarian cancer patients (n=8) and healthy donors (n=4). In high grade serous ovarian cancer patients, mutant p53 is found in tumor cells in nearly all cases. Notably, the inventors could monitor this mutant p53 in the circulation in 7 of the 8 patients (FIG. 20). By contrast, none of the healthy donors had appreciable levels of p53 in the circulation. To validate these results, the inventors conducted parallel non-specific binding analysis with plasma samples from each of the cancer patients and found that these samples indeed contained p53 (FIG. 20). Thus, the inventors' non-invasive SMAC p53 blood test is able to identify human ovarian cancer with 90% sensitivity and 100% specificity.

Figure 21:
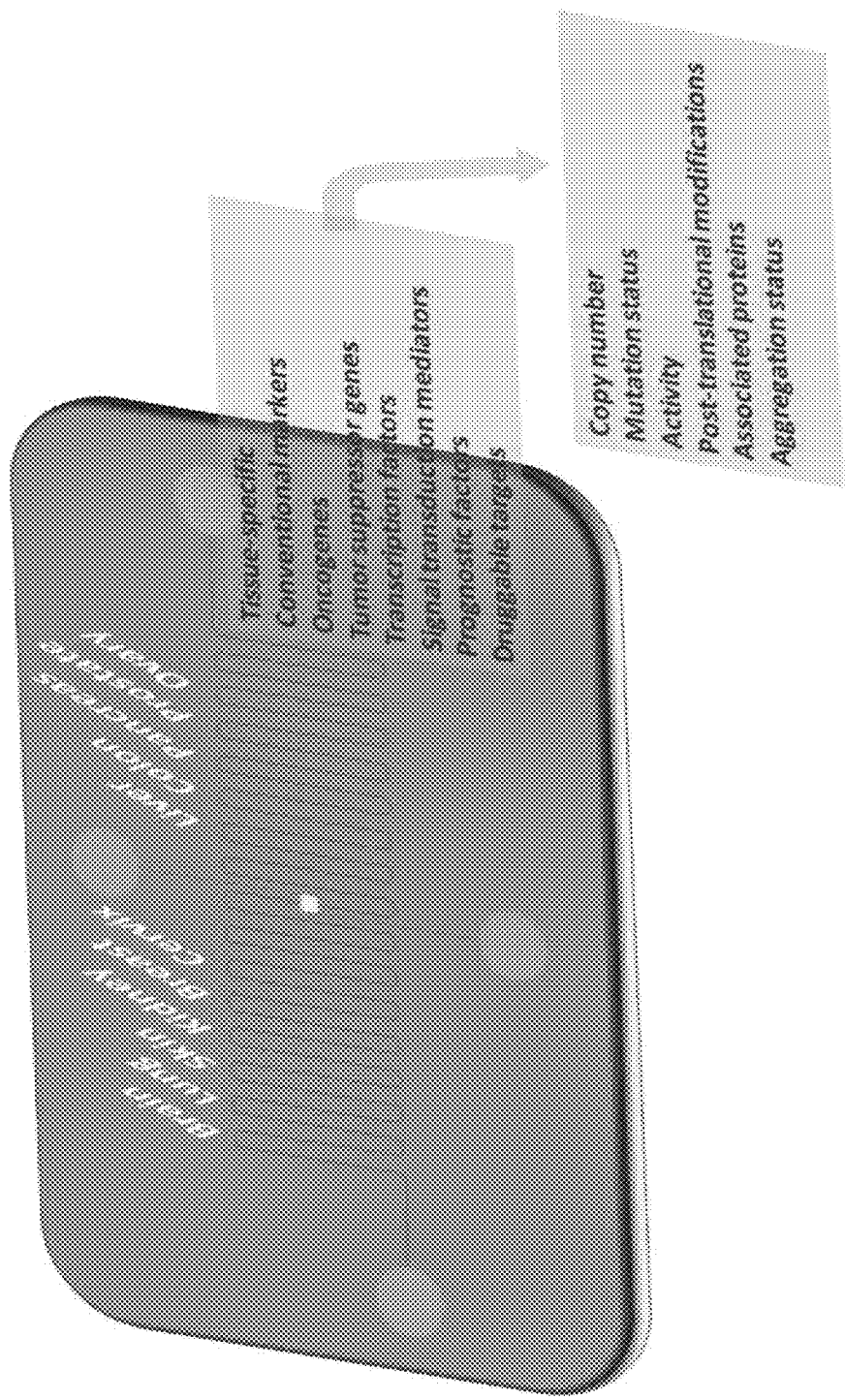
FIG. 21 Concept for a universal, non-invasive cancer detection, diagnosis, and monitoring SMAC chip. In this prototype, the chip may be organized on a single axis with multiple different tissue types (e.g., lung, pancreas, and ovary). On the orthogonal axis, proteins relevant to that tissue or cancer type (e.g., oncogenes, transcription factors, drug targets) may be pulled down and probed. The digital nature of SMAC detection enables structural and functional information (e.g., mutation status, activity, post-translational modifications) about these proteins to be elucidated. In principle, the SMAC chip can readily accommodate a high-throughput format for the simultaneous detection and characterization of hundreds or thousands of cancer-relevant biomarkers.

The SMAC platform in principle could be applied for the analysis of any true tumor-specific biomarker, including mutant oncoproteins (e.g., RAS, BRAF, PIK3CA, and EGFR), mutant tumor suppressor proteins (e.g., p53, CDKN2A, PTEN, RB, APC, SMAD) or pathogen-encoded oncoproteins (e.g. E6 and E7 from HPV). Furthermore, the design of the SMAC chip is exceptionally well-suited for multiplex, high-throughput, and even genome-wide analysis (FIG. 21). The inventors envision that non-invasive SMAC profiling of the tumor will yield insight into the gene expression signature of a tumor. Moreover, because of the digital detection features of SMAC, gene expression information can be readily layered with multi-dimensional functional information about the tumor, such as transcription networks, core signaling pathways, and the effector or biochemical status of key proteins. Altogether, this information will enable a comprehensive map of the tumor to be built, which will facilitate the early detection, diagnosis, and management of cancer.

SMAC has the potential to realize the promise of non-invasive early cancer detection because of several key innovations that underlie this technology. The following table lists these innovations and along with their significance.

| SMAG innovation | Significance |
| --- | --- |
| High density PEG/biotin-PEG capture surface coating | Achieves high target molecule capture efficiency with ultra-low background and non-specific binding |
| 'Plasma protection' bonding of SMAC chip | Achieves precision (μm-scale resolution) assembly of SMAC chip without disrupting capture surface coating in any way |
| Automaled, computer-controlled circulation system in a microfluidic chip with integrated fluid mixers | Achieves high target molecule capture efficiency and target concentration from the sample by a factor of >10,000 |
| Automated, parallel washing steps | Achieves rapid washing and ultra-low background |
| Single molecule TIRF microscopy for non-invasive biomarker detection in clinical samples | Brings TIRF-based single molecule imaging technology into the disease detection, diagnosis, and monitoring arena |
| Threshold-based 'cluster analysis' algorithm to discriminate between specific and non-specific binding | Solves the challenge of non-specific binding of detection reagent, essentially filtering out all assay background |

Furthermore, an overview of the workflow and processes involved in the SMAC system is illustrated below. These steps can be categorized into 3 main steps: (1) SMAC chip synthesis, (2) target molecule capture and detection, and (3) single-molecule imaging and analysis.

| SMAC chip synthesis | Target capture and detection | Single molecule imaging and analysis |
| --- | --- | --- |
| Capture surface coating | Capture reagent conjugation | Single molecule total internal reflection fluorescence microscopy |
| Channel enclosure synthesis | Automated sample circulation | |
| Chip bonding and assembly | Detection reagent incubation | Digital signal quantification |
| | Automated washing | |

The various components of the SMAC system and its innovations are explained in detail throughout. Explained in a step-by-step format are the procedures for synthesizing the SMAC chip, running a SMAC assay, and analyzing the resultant data.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

SMAC Chip Components

Figure 22:
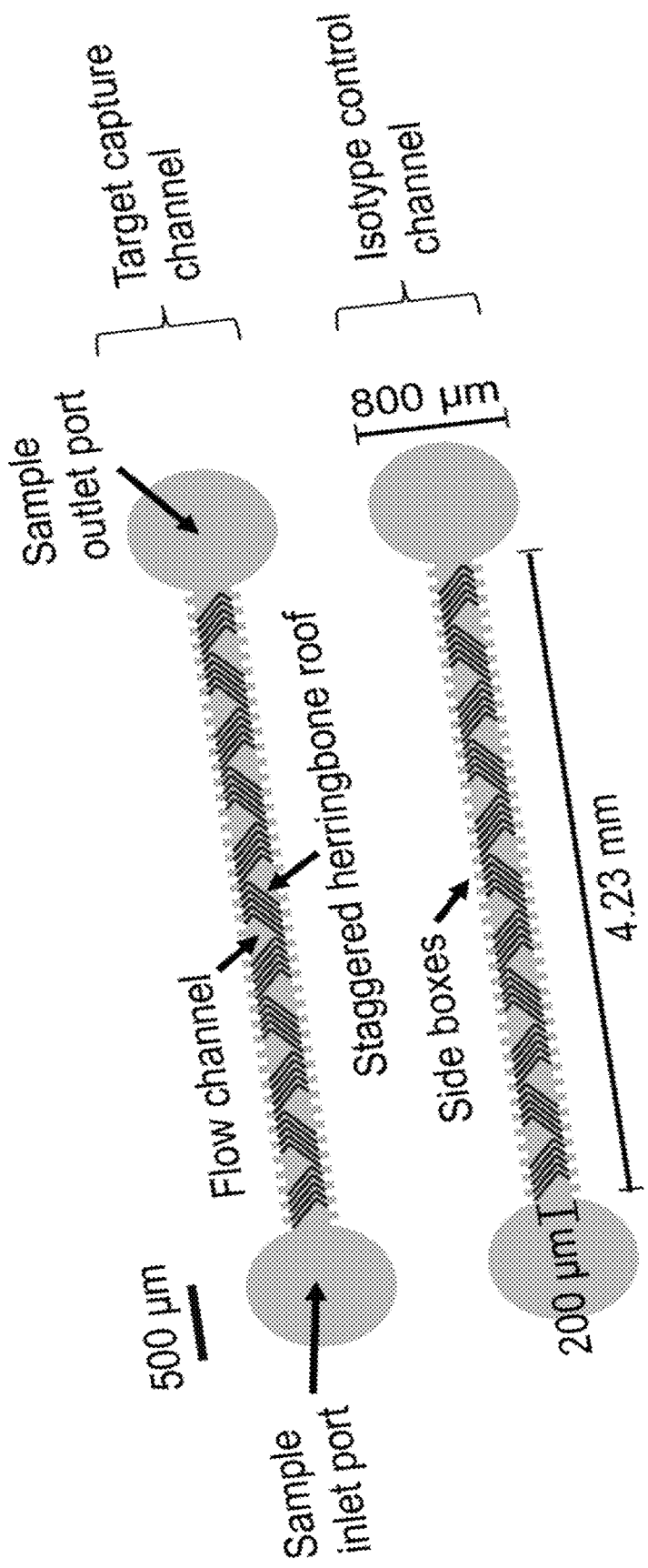
FIG. 22 Schematic drawing of SMAC chip. Shown is a 2D horizontal cross-section drawing of a SMAC chip. This SMAC chip contains 2 independent flow channels per chip. The inlet and outlet ports have a radius of 400 µm. The flow channel has a length of 4.23 mm and a width of 0.2 mm, with 42 boxes composed of 50×50 µm squares along each side. The channel also contains a roof with staggered herringbone geometry. Alternating arrays of 5 herringbone grooves (11 per channel) are offset at 33% distance into the channels. Multiple channel and roof heights are possible depending on the intended application. In general, the roof depth is ~25-50% of the channel height. We have fabricated devices over a wide range of total heights, from 20 µm to >250 µm. The side boxes and staggered herringbone roof create counter-rotating microvortices which increase the probability of collisions between target proteins in solution and capture reagent on the chip surface, thereby enhancing capture efficiency.
Figure 23:
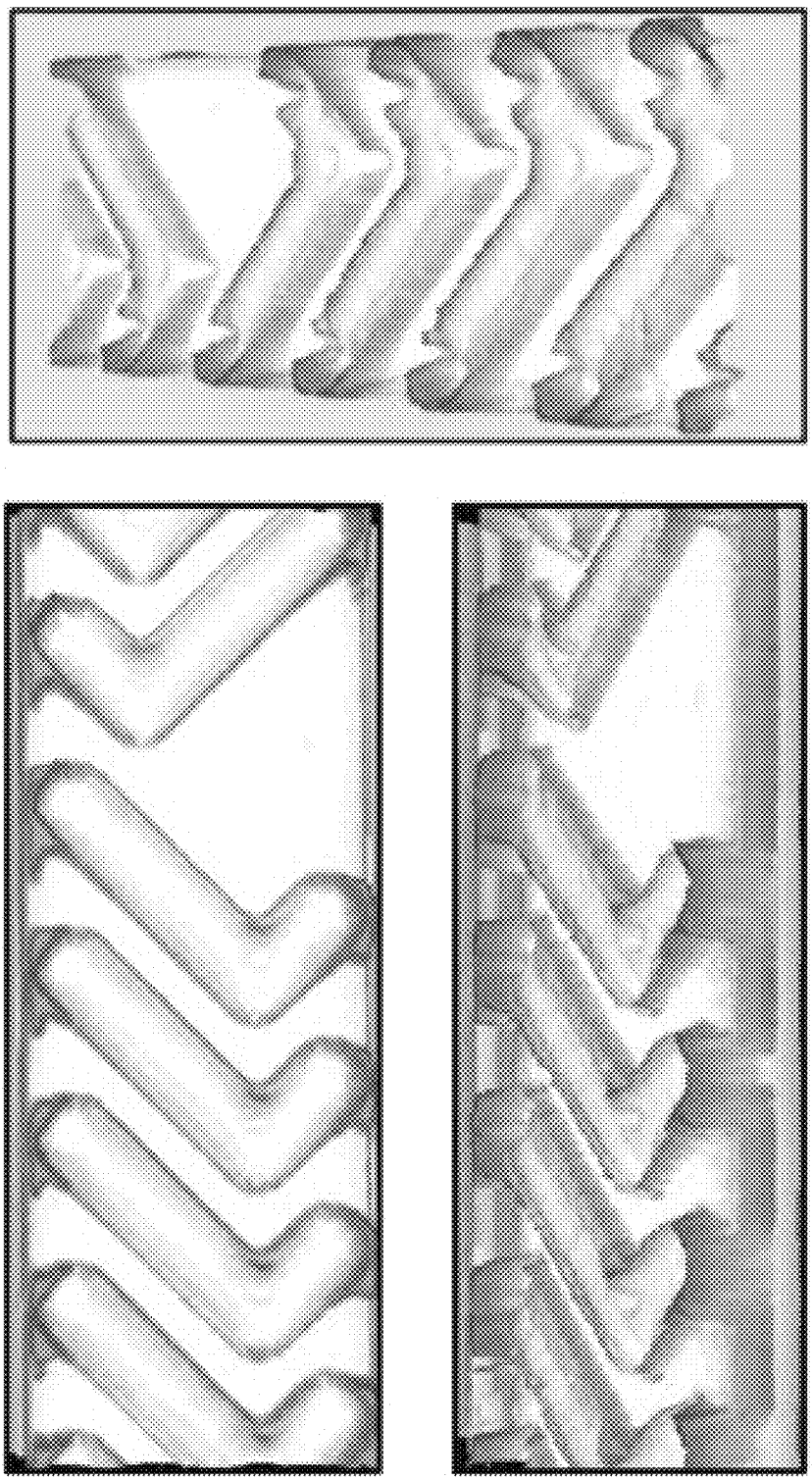

A SMAC chip of the present invention consists of 2 fundamental components: a capture surface and a microfluidic flow chamber. The microfluidic flow chamber serves as an enclosure that creates flow channels within the chip. A schematic diagram of one embodiment of a microfluidic flow chamber of a SMAC chip is shown in FIG. 22 wherein this top-down view depicts the two separate SMAC flow channels (grey region) residing on a single SMAC chip; for clarity the capture surface has been omitted from the diagram. In this one embodiment depicted in FIG. 22, the inlet and outlet ports (for solution entry and exit, respectively) are visible on the sides of each of the channels. The specific microfluidic flow channels depicted possess arrays of staggered herringbone grooves (black lines) at the top (or 'roof'). A 3D diagram of a SMAC chip, showing both the surface and the roof from a side view, is depicted in FIG. 25. The grooves function as a chaotic micromixer that increases the probability of collisions between one or more target molecule(s) in a solution and capture reagent on a capture surface of a SMAC chip, thereby improving capture efficiency. Shown in FIG. 23 are 3D confocal micrographs from different view angles (a: top down, b: side, c: front) of a roof of a SMAC chip illustrating the staggered herringbone grooves that are part of a flow channel enhancing the mixing of a solution. For clarity, only the roof specific to one or more channels of a microfluidic flow chamber of a SMAC chip are shown, and the roof has been flipped upside down to show the grooves of a channel. Notably, the staggered herringbone micromixer is just one example of a micromixer that could be used in the present invention and other micromixer designs able to promote chaotic flow may be used in the present invention.

The sides of a flow chamber of a microfluidic flow chamber may contain indentations such as boxes (FIG. 22), or grooves, as examples that further promote chaotic flow and also serve as guide markers that identify specific positions along the channels during imaging. Many indentation designs may be used in the present invention on the sides of a channel, as the indentations promote chaotic flow. Furthermore, positional markers such as numbers and/or letters could be etched in to the sides of a chamber and may be used to label coordinates in a channel.

Though FIG. 22 depicts only two flow channels in a microfluidic flow chamber of a SMAC chip of the present invention, a SMAC chip of the present invention may have many flow channels; for example, in the range of 2 to 1,000 flow channels, 10 to 900 flow channels, 50 to 500 flow channels, 100 to 400 flow channels, or greater than 1,000 flow channels on a SMAC chip. These channels may be used to run an assay in a multiplex or high throughput manner. For example each channel of a SMAC Chip may be used to detect a specific target molecule; for example, a SMAC chip may be able to identify in the range of 2 to 1,000 target molecules, 10 to 900 target molecules, 50 to 500 target molecules, 100 to 400 target molecules, or greater than 1,000 target molecules (i.e. the simultaneous detection of 2 to >1,000 different target molecules from a single sample). An application of such a SMAC chip design might be, for instance, to characterize global gene expression patterns in a clinical sample to identify potential diseases an individual may have. Another potential application might be to characterize the comprehensive gene profile of a tumor from a blood sample to choose the most promising therapy for that particular patient.

Alternatively, or in conjunction with the above, certain channels may be used as positive or negative controls to validate each SMAC assay and to account for possible minor chip-to-chip variability. For example, in FIG. 22, the bottom channel has been designated as an 'isotype control channel', which will be conjugated with isotype control IgG instead of target-specific capture Ab. The isotype control channel is used to assess the amount of potential non-specific binding attributable to each individual sample matrix and therefore allows one to identify and exclude false positive results from an assay. See FIG. 20 for an example of the isotype control channel in practice.

Assembly of a SMAC Chip

The purpose of SMAC chip assembly is to sequentially build up a series of preferably 6 dependent chemical 'layers', within a SMAC chip flow channel, as illustrated in FIG. 25.

Layer B (bottom) is preferably a glass bottom, and layer T (top) is preferably a PDMS enclosure of a flow channel, respectively. In between these layers lies the space in which layers 1-6 will be deposited and through which sample solution will flow. Layers 1 (aminosilane) and 2 (biotin-PEG/PEG) are deposited during SMAC chip synthesis, prior to chip assembly. These layers form the 'immature capture surface' upon which the other layers will be formed. Layers 3 (NeutrAvidin) and 4 (biotin-labeled capture reagent, such as a capture Ab) are deposited in solution phase after SMAC chip assembly. Together, layers 1-4 form the 'mature capture surface' that is capable of recognizing target molecules in the sample.

Layer 5 consists of the target molecules themselves and is deposited by continuous circulation of the sample within the chip via the automated circulation system. Layer 6 is the final layer and consists of fluorescence-labeled detection reagent molecules (such as a detection Ab against (i.e. that specifically binds to) the target molecules). Because layer 6 displays fluorescence, the number of detection reagent molecules in this layer can be read by single-molecule TIRF imaging, which can then be converted to the number of target molecules (layer 5) in the sample. Note that layer 6 is a 'dependent layer'; that is, layer 6 cannot be deposited in the absence of layer 5 (or any layer below it) as described in the section titled, Methods for Single-Molecule Detection. Furthermore, any background fluorescence-labeled detection reagent molecules in the space between layer 6 and the PDMS roof (layer T) are not read by our TIRF imaging system; thereby guaranteeing extremely high signal-to-noise ratios (described in detail in section titled, Methods for Single-Molecule Detection).

Covalent Coating of a SMAC Chip Capture Surface

The capture surface is typically composed of glass (e.g. borosilicate or quartz) but may also be composed of other materials (e.g., silicon, PDMS, polystyrene, polycarbonate, polyvinylchloride, polymethyl methacrylate, cyclic olefin copolymer) depending on the specific application. For TIRF imaging, a glass surface is required, and the glass should have a preferred thickness of 100-200 µm. For other application types (such as those that do not involve microscopy), a thickness >200 µm (up to >2 mm thickness) is possible.

A preferred SMAC chip utilizes a borosilicate glass substrate with a thickness in the range of 100-500 µm, 150-400 µm, 130-170 µm, 140-200 µm, or 200-500 µm for the capture surface. The length and width of the substrate may have a range of possible dimensions, from 1 mm to 100 mm, 10 mm to 90 mm, 20 mm to 80 mm, 30 mm to 70 mm, less than 5 mm or greater than 100 mm. A preferred substrate size is a 22×22 mm square.

For passivation of the capture surface, the glass substrate (or bottom) is first cleaned with ultrapure water in an ultrasonic bath for 10 min, dried under a stream of filtered air, exposed to high power atmospheric plasma for 5 min for surface activation, and then immediately placed in methanol. Note that the substrate may also be cleaned by other methods such as with Piranha solution (sulfuric acid, hydrogen peroxide mixture) or with 1 M potassium hydroxide. Plasma exposure for surface activation is chosen because it is an efficient and rapid procedure. Alternative methods to plasma for surface activation that could be employed include UV/ozone and corona discharge among others.

The glass substrate is then covalently coated with a coupling agent such as aminosilane (e.g., N-(2-aminoethyl)-3-aminopropyltrimethoxysilane, 3-aminopropyldimethyloxysilane, 3-aminopropyltrimethoxysilane, propyldimethylmethoxysilane, N-(6-aminohexyl)aminomethyltriethoxysilane); the deposition of aminosilane may be carried out in either a liquid phase in organic solvents (e.g. methanol, toluene) or in vapor phase, either once or multiple times sequentially. This reaction may also occur over a range of temperatures from 25° C. to over 150° C. In our experience, liquid phase aminosilane deposition is in general superior to vapor phase deposition, and a single round reaction at ambient temperature is sufficient for high passivation density; we have observed that a reaction temperature above 120° C. generates strong autofluorescence on single molecule imaging. For the liquid phase reaction, 1% (v/v) aminosilane with 5% (v/v) glacial acetic acid in methanol is optimal; excess (>1%) aminosilane may produce autofluorescence background.

After aminosilane deposition, the glass substrate is washed thoroughly with ultrapure water, dried under a stream of filtered air, and conjugated with a reactive agent such as biotin-PEG-succinimidyl valerate (SVA) (0.3 mg) in 10 mM sodium bicarbonate (pH 8.5) or other similar solvent. Besides the SVA reactive group, multiple other chemical reactive group types are possible, including but not limited to NHS ester, imidoester, epoxide, isothiocyanate, isocyanate, sulfonyl chloride, aldehyde, carbodiimide, acyl azide, anhydride, fluorobenzene, carbonate, and fluorophenyl ester. The PEG polymer may be of various sizes from <2 kD to >20 kD; 5 kD PEG is a preferred size. This reaction may be carried out from <3 hr to >12 hr. The glass surface is then washed thoroughly with ultrapure water, dried under a stream of filtered air, and conjugated with a mixture of biotin-PEG-SVA (0.3 mg) and PEG-SVA (16 mg) (1:50 mass ratio) from <3 hr to >12 hr. The 2-step PEG/biotin-PEG passivation procedure described above is superior to conventional 1-step passivation (FIG. 3).

Note that for both the biotin-PEG-SVA first coating step and biotin-PEG-SVA/PEG-SVA second coating step, a range of biotin-PEG-SVA and/or PEG-SVA dosages are possible. The dosages listed above are preferred values for single-molecule studies, but the optimal dosages may vary for other SMAC application types. Furthermore, a coating time of >3 hr is sufficient for high density passivation; the first step biotin-PEG-SVA coating is typically performed for 4 hr and the second step biotin-PEG-SVA/PEG-SVA coating overnight, although it should be recognized that these time lengths could vary without substantial effect on coating quality.

After coating, the glass surface is washed thoroughly with ultrapure water and dried under a stream of filtered air. The surface is placed in a clean container, vacuumed, flushed with pure nitrogen, sealed, and stored at −20° C. Under these conditions, the biotin-PEG/PEG conjugated substrate is stable for at least several wk.

Multiple variations of the coating scheme described above are possible. For example, instead of aminosilane, other types of silane coupling agents may be used, including those that contain vinyl, epoxy, acryloxy, methacryloxy, styryl, isocyanurate, ureide, sulfide, isocyanate, or mercapto groups, among others, rather than amino groups. In these cases, it is important that the biotin-PEG and PEG reagents used for coating contain reactive groups that are compatible with the particular silane. Furthermore, the need for first coating with a silane-based compound followed by a PEG-based compound can be bypassed with a biotin-PEG-silane or PEG-silane, which directly generates biotin-PEG/PEG groups on the glass substrate. The inventors have shown that this is an effective and rapid alternative coating approach. Furthermore, a biotin reaction scheme can be bypassed with a dual reactive PEG moiety, such as SVA-PEG-SVA, which could covalently link to any amine-bearing capture reagents. Either of the SVA groups that flank the PEG could be substituted with any of the other reactive groups listed above. Moreover, besides PEG, a variety of other materials may be used for surface passivation, including but not limited to polyacrylamide, poly(acrylic acid), poly(N-hydroxyethyl acrylamide), poly(2-hydroxyethyl methacrylate), poly(2-methacryloyloxyethyl phosphorylcholine), poly(vinyl alcohol), poly(vinyl pyrrolidone), hydroxyethylcellulose, hydroxypropyl methylcellulose, dextran, or hyaluronic acid.

Microfluidic Flow Chamber

The SMAC chip enclosure is assembled on top of the glass substrate and creates open flow channels through which solutions may flow. The design of the chip enclosure dictates the shapes of these flow channels, and specific shapes may be introduced to control flow patterns within the channels. For instance, to maximize capture of target molecules, a chaotic micromixer could be incorporated into the design to promote encounters between target molecules and capture reagent. Alternatively, the flow channels could be partitioned into separate 'zones' segregated by valves to trap target molecules in a desired region. Shown in FIG. 26 are representative samples of different SMAC chip design flow chamber variations (with combinations of staggered herringbone, serpentine, split, intersect, trap, and/or spiral features) that were developed. Each of these design variations is intended to serve a different purpose. As shown in FIG. 26, the outer squares delineate the boundaries of the glass substrate. The black lines indicate the channels as they would appear in a top-down view. For the bottom two channels in the left column, grey regions indicate the channels and the black lines indicate staggered herringbone grooves on the roof that penetrate into the channels.

A wide range of other microfluidic design types are conceivable for the SMAC chip depending on the specific application. Channel length may vary from 100 μm to 10 cm (preferred range 1-10 mm), and channel width may vary from 25 μm to 1 cm (preferred range 100-500 μm), depending on the intended application. The channel height may range from 1 μm to 2 mm, with a preferred range of 100-300 μm, and a most preferred height of 200 μm.

The SMAC circulation system acts synergistically with chaotic micromixers to efficiently pull down target molecules onto the capture surface. Therefore, integration of these micromixers into the SMAC chip design is preferred. Below is a summary of different types of passive and active chaotic micromixers that are known in the field. Active micromixers are those which require an external energy supply to operate while passive micromixers rely on structures built into the microfluidic device itself and therefore require no external energy outside of the circulation pump. Any of these micromixers could in principle be incorporated into the SMAC chip, although the performance of each should be evaluated empirically.

| Table of active and passive microfluidic chaotic mixers. | |
| --- | --- |
| Active micromixers | Passive micromixers |
| Acoustic/ultrasonic | Embedded barriers |
| Dielectrophoretic | Grooved staggered herringbone |
| Electrohydrodynamic force | Intersecting channels |
| Electrokinetic instability | Lamination |
| Electrokinetic time-pulsed | Serpentine structure |
| Magnetic | Slanted wells |
| Magneto-hydrodynamic force | Surface chemistry technology |
| Pressure perturbation | Twisted channels |
| Thermal | Zigzag channels |

A preferred SMAC chip enclosure forming one or more flow channel(s) is made of a silicone elastomer PDMS due to its low cost and ease of handling. Nonetheless, other materials are possible for the enclosure, such as silicon, glass, or polymer (e.g., polystyrene, polycarbonate, polyvinylchloride, polymethyl methacrylate, and cyclic olefin copolymer).

For fabrication of the SMAC chip enclosure forming one or more flow channel(s) in PDMS, standard photolithography techniques are used. For high quality of fabrication, these techniques should be performed in at least a class 100 cleanroom. Note that photolithography techniques are well-established and should be familiar to those skilled in the art. As such, variations on the fabrication process are possible and the procedure provided below is merely intended as an example of a fabrication process that may be used to create a SMAC chip.

A silicon wafer is cleaned with acetone and isopropanol, and then subjected to dehydration bake. The wafer is exposed to high power oxygen plasma (e.g. 100 W for 3 min at 300-500 mTorr oxygen pressure) to promote photoresist adhesion. Photoresist (e.g. SU-8) is spin coated onto the wafer to a desired thickness (e.g. 10 µm to 500 µm). The wafer is then subjected to a soft bake (65° C./95° C.) and subjected to UV exposure in a mask aligner loaded with a high-resolution mask. The wafer is then subjected to post-exposure bake (65° C./95° C.). Multiple layers of photoresist may be deposited onto the wafer by repeating the steps above. In a preferred SMAC chip design, the first layer consists of the main channel with side boxes while the second layer consists of the arrays of staggered herringbone grooves. After all layers of photoresist have been deposited, the wafer is developed under agitation to yield a master template for synthesis of the silicone elastomer SMAC chip enclosure.

To produce the chip enclosure and form flow channels, PDMS elastomer is mixed with curing agent in a 10:1 ratio (by weight), poured onto the patterned wafer master, degassed, and incubated at 80° C. overnight. The PDMS is then removed from the master, cut into individual devices (may range from 1 to 100 devices per wafer in a single PDMS casting round depending on the size of the SMAC chip) with a razor blade, and bored with inlet/outlet tubing holes (typically 750 µm diameter, but may vary from <500 µm to >5 mm) under a stereomicroscope. The PDMS devices are washed in an ultrasonic bath with isopropanol for 20 min and then with ultrapure water for 5 min. Devices are dried under a stream of filtered air. Note that the procedure for PDMS casting and handling is well-established in the field, and variations of the above procedure are possible.

The 'Plasma Protection' Bonding Technique

Because of bonding constraints, state-of-the-art methods are currently incapable of producing microfluidic devices with precise (m resolution) geometry that also exhibit the extremely low levels of background and non-specific surface binding required for single molecule imaging. Thus, in order to create this type of chip, the inventors engineered a new way of bonding microfluidic devices. Conventional methods for bonding microfluidic devices require harsh conditions (such as exposure to atmospheric or oxygen plasma followed by high temperature) and are incompatible with coated substrates. Shown in the FIG. 27 is a non-specific binding test in which fluorophore-labeled detection reagent was added to SMAC chips with pre-coated glass substrate that underwent either conventional plasma bonding (top panel) or adhesive bonding of the present invention (bottom panel). As can be seen, there is strong non-specific binding in SMAC chips assembled by conventional plasma bonding, as evidenced by the strong fluorescence. However, in SMAC chips assembled by adhesive bonding the non-specific binding is minimal. This illustrates that plasma exposure severely damages the PEG coating on the chips.

A potential solution to this problem is to carry out in situ coating in SMAC chips after bonding. However, PEG/biotin-PEG passivation of the glass surface within a microchannel after bonding generates strong autofluorescence background likely originating from multi-layer aminosilane deposition. Shown in FIG. 28 is a specific binding and background comparison of SMAC chips conjugated with PEG/biotin-PEG by either in situ coating or the standard coating technique. The chips were incubated with or without GFP, and the fluorescence signal was then examined by single molecule imaging. As can be seen, in situ coating leads to strong autofluorescence background in the SMAC chips, precluding the use of this technique for single molecule analysis. Note that the inventors have developed a technique for in situ coating of SMAC chips which eliminates this background problem (see above section on Covalent Coating of the SMAC Chip Capture Surface) and is thus suitable for single molecule analysis.

Single molecule imaging on coated glass using conventional methods is performed in flow chambers sealed by adhesives (e.g. tape or epoxy). These bonding methods, however, are prone to leakage under prolonged, high velocity flow and, critically, suffer from lack of precise control over chip size and shape. With the novel bonding technique reported here, rapid (in the range of 1 to 5 min., 2 to 4 min., approximately 3 min, or less than 3 min bonding time), high-resolution (m scale), covalent bonding of microfluidic devices can be achieved without altering the coated surface in any way.

Precision bonding of the PDMS devices to a coated glass substrate may be conducted either inside or outside of a cleanroom environment, but in general the work area should be kept free of particles; the presence of particles on the PDMS or glass substrate could impair the bonding process. Prior to bonding, the coated glass substrate is attached to an alignment guide featuring an imprint that matches the shape and size of the flow channel. An elastomer cover fabricated with µm precision to the exact dimensions of the flow channel is then placed on top of the glass surface at the position of the channel imprint on the alignment guide. This cover allows us to activate the glass surface for bonding via oxygen plasma while preserving the high density PEG/ biotin-PEG passivation in the flow channel. Lack of this cover would cause the PEG/biotin-PEG layer to be destroyed by oxygen plasma bombardment (or similar harsh bonding techniques). BINDING METHOD. The coated glass surface (with elastomer cover, that may be made of PDMS) and PDMS devices (Roof in FIG. 25) are placed inside a plasma etcher and treated with oxygen plasma for 30 sec at 40 W RF power (pressure of 0.4-0.5 torr). The precise plasma RF power and oxygen pressure may vary. In addition, other bonding energy sources (e.g. UV/ozone or corona discharge) are possible. The elastomer cover is removed, and PDMS devices are then assembled to the coated glass substrate under a stereomicroscope with the alignment guide as a reference for the channel position. The assembled SMAC chips are incubated at 80° C. for 3 min to drive the bonding to completion. Chips are placed in a clean container, vacuumed, flushed with pure nitrogen, sealed, and stored at −20° C. SMAC chips may be stored for at least several weeks without significant loss of performance.

FIG. 29 illustrates the outcome of a non-specific binding test of a SMAC chip in which the elastomer cover was placed on only part of the PEG/biotin-PEG-conjugated glass substrate in the channel. Thus, after chip assembly, a hybrid channel is formed in which a portion of the channel inside the plasma protection zone (bottom panel) has an intact PEG/biotin-PEG coating, while the portion outside the protection zone (middle panel) has a damaged coating. As can be seen, when a non-specific fluorophore-labeled detection reagent is added to the SMAC chip, the region of the channel outside the protection zone displays strong non-specific binding background, while the region inside the protection zone displays minimal background. This proof-of-principle experiment demonstrates that the plasma protection bonding technique maintains the integrity of the surface coating inside our SMAC chip while permitting precise plasma bonding.

Alternatives to Plasma Protection Bonding

Although plasma protection bonding achieves precise bonding geometry without chip leakage while maintaining an intact surface coating on the glass substrate, alternatives to this bonding approach are possible. For instance, as mentioned above, the flow chambers could be attached to the glass substrate via adhesives such as tape or epoxy. Furthermore, the inventors have developed methods for in situ surface coating that exhibit high coating density and no background autofluorescence. These methods are useful for situations in which plasma protection bonding is unfeasible, such as with very intricate chip designs that complicate the process of cover alignment (see above). An example of a step-by-step procedure for in situ coating with biotin-PEG-silane is described below. Note that besides biotin-PEG-silane, other types of coating materials could be deposited on the glass substrate in a similar manner.

First, a glass substrate is cleaned with ultrapure water in an ultrasonic bath for 10 min, dried under a stream of filtered air, and exposed to high power atmospheric plasma for 5 min for surface activation. Note that the variations to this procedure described in the above section titled, Covalent coating of the SMAC Chip Capture Surface. The glass substrate is then immediately attached to a PDMS device via conventional bonding methods (e.g. atmospheric or oxygen plasma bonding) to form the SMAC chip. Pure methanol is introduced into the chip, and the chip is then vacuumed briefly to remove bubbles. 10% biotin-PEG-silane (by weight) in methanol is then passed into the chip and incubated for 30 min at 25° C. Then the chip is washed twice with methanol followed by twice with ultrapure water, dried, and incubated for 30 min at 80° C. to promote biotin-PEG-silane cross-linking. Afterwards, the chip is vacuumed, flushed with pure nitrogen, sealed, and stored at −20° C. Note that all variations to this procedure—including those that use different coating materials, time, or temperature—described in the above section titled Covalent Coating of the SMAC chip capture Surface apply here as well. For instance, the inventors have examined the effect of number of coating rounds, different coating duration, and different bake time and temperature on the quality of biotin-PEG-silane coating (data not shown).

The Conjugation Process and Buffer Selection

After SMAC chip synthesis and the formation of the microfluidic flow chamber, liquid-phase conjugation is performed to add layers 3 (NeutrAvidin) and 4 (biotin-labeled capture reagent) to the SMAC chip (as illustrated in FIG. 25) in preparation for sample circulation. These layers sequentially added preferably by automated flow through the chip via an external multi-channel pump (e.g., peristaltic, pneumatic, or infusion/withdrawal pump). However, the layers may also be introduced manually with a syringe, pipette, or other instrument. Note that NeutrAvidin is chosen because it is less prone to non-specific interactions compared to its counterparts avidin and streptavidin yet retains the same ultra-high affinity for biotin (Kd ~10-15 M). However, both avidin and streptavidin, as well as other biotin-binding proteins, may be used. Furthermore, the NeutrAvidin/biotin reaction scheme is relevant for coating methods that involve biotin conjugation to the chip surface, such as that described above and in FIG. 25, but not for coating methods that do not involve biotin conjugation. In situations that do not involve biotin, the contents of the capture layers need to be appropriate for the specific types of coating employed. For example, if the surface coating is with SVA-PEG-SVA (as mentioned above.), NeutrAvidin would not be needed, and the capture reagent would not need to be biotin-labeled. In this case, an unmodified capture Ab could directly be introduced into the SMAC chip. This same line of reasoning holds for other coating types.

Note also that intermediate layers could be included between layers 3 and 4 as illustrated in FIG. 25 (e.g., layers 3.1, 3.2, 3.3 . . . 3.n) to expand the total amount of capture reagent that can be conjugated to the chip. For example, the inventors have developed methods that use multi-arm (e.g., 4- or 8-arm) biotin-PEG to amplify the number of capture Ab binding sites. Since each molecule of NeutrAvidin has 4 biotin binding sites, and since each molecule of 8-arm biotin PEG has 8 NeutrAvidin binding sites, the insertion of additional intermediate 8-arm biotin-PEG/NeutrAvidin layers would amplify the number of capture Ab binding sites by 21-fold (7 unoccupied NeutrAvidin-binding sites from each 8-arm biotin PEG×3 unoccupied biotin-binding sites from each partner NeutrAvidin) each cycle. Thus, the number of capture Ab binding sites with each 8-arm biotin-PEG/NeutrAvidin coating cycle (n) would scale as a factor of 21n; after only 2 coating rounds, the capture Ab binding capacity of the SMAC chip would expand by 441-fold. This is an exceptionally powerful approach to boost the sensitivity of a SMAC assay when required.

An additional important consideration is the buffer system in which the NeutrAvidin and biotin-labeled capture reagent are deposited. For devices made of hydrophobic materials, such as PDMS, there is a large tendency for non-specific absorption of proteins to the walls of the chip. Therefore, any biotin-labeled capture reagent that adheres to the chip walls could in principle capture target molecules, thereby interfering with the accumulation of target molecules on the glass imaging surface. To circumvent this problem, the inventors equilibrate the SMAC chip in a buffer system containing nonionic surfactant, such as polysorbate (20) sorbitan monolaurate (Tween-20) and related compounds (e.g., CHAPS, Triton X-100, NP40), which blocks the absorption of proteins to PDMS and other hydrophobic materials. Alternative choices for surfactant with similar mechanisms of action include Pluronic F-127 or polyoxyethyleneglycol dodecyl ether (Brij 35) and related compounds. Both NeutrAvidin and biotin-labeled capture reagent should also be prepared in buffer containing these surfactant compounds. A step-by-step procedure of the liquid-phase conjugation process is provided below.

Conjugation Procedure with Variations

All reagent/sample introduction and removal, as well as wash, steps described below are performed under automated flow actuated by an external multi-channel pump (e.g., peristaltic, pneumatic, infusion/withdrawal pump). The preferred flow rate for wash steps is 500 µl/min, with a range of <1 µl/min to >10 µl/min. The preferred setup is to control the flow with a peristaltic pump that draws solutions through the SMAC chips and into a waste reservoir. Solutions can also be passed through the chips manually with a syringe, pipette, or other instrument if desired but the automated setup is preferred due to its convenience, speed, and uniformity. Note that the values for volume and concentration of all solutions mentioned below are provided for reference; these values are representative for typical SMAC experiments but may vary depending on the specific application and size of the SMAC chips.

SMAC chips stored at −20° C. are first thawed to ambient temperature, connected to connected to inlet and outlet polytetrafluoroethylene tubing (381 µm internal diameter, 229 µm wall thickness), and equilibrated with 10 mM Tris-HCl pH 8.0, 50 mM NaCl, 0.05% Tween-20 (T50) buffer. Multiple other tubing dimensions (internal diameter and thickness from 100 µm to 1 cm) and materials (e.g., silicone, polypropylene, C-Flex, Viton, Tygon, Norprene, Santoprene) are possible depending on the specific application. Chips may also be equilibrated in other buffer conditions, including under various salt or surfactant concentrations. Chips may be equilibrated under static (i.e. no flow) conditions or dynamic conditions (i.e. continuous flow through the channels); the preferred setup is automated continuous flow actuated by an external pump at 50 µl/min. Chips may be vacuumed for ~1 min as they are equilibrated in order to prevent bubble formation in the channels.

The chips are then incubated with NeutrAvidin (20 µl; 0.1 mg/ml) in T50 buffer for 10 min. The preferred flow rate for introduction of NeutrAvidin is 50 µl/min, with a range of <1 µl/min to >10 ml/min. Chips are then washed via pump with T50 buffer (1 ml) and incubated with capture reagent (e.g. biotin-labeled capture Ab) (2 µl; 0.1-1 mg/ml) in T50 buffer with 0.1 mg/ml BSA (T50-BSA). Note that the capture reagent is in excess and may be diluted to <0.001 mg/ml with minimal loss in SMAC sensitivity. Further note that the capture reagent may be incubated at a temperature range from 4° C. to 37° C. and for a duration of <5 min to >24 hr; a duration of 30 min at ambient temperature is preferred. However, capture reagent may be incubated at 4° C. overnight with minimal loss in SMAC sensitivity. The chips are then washed with T50-BSA (1 ml) and at this point are ready for sample circulation.

The Circulation System and Different Configurations

The automated circulation system is a critical feature of SMAC technology. As shown in FIG. 8, the circulation system enhances the sensitivity of SMAC by over 100-fold. Note that the circulation system acts synergistically with the chaotic micromixer design (staggered herringbone grooves in our preferred prototypes with variations and other design types allowed) of the SMAC chip; as time progresses, target molecules accumulate on the surface of the chip under continuous closed-loop flow and become concentrated by a factor of >10,000. Due to the presence of the chaotic micromixer, a high flow rate (e.g. 500-1,000 µl/min) yields an improved capture efficiency compared to a low flow rate (as shown in FIG. 9). Thus, even large sample volumes (ml scale) can be readily run in the SMAC system, with a pass through time of only a few min. The inventors have found empirically that if the circulation period is sufficient (>2 hr), >50% of target molecules in a sample can be precipitated on the SMAC chip with readily available capture Ab of reasonable affinity (KD ~1-10 nM).

Figure 24:
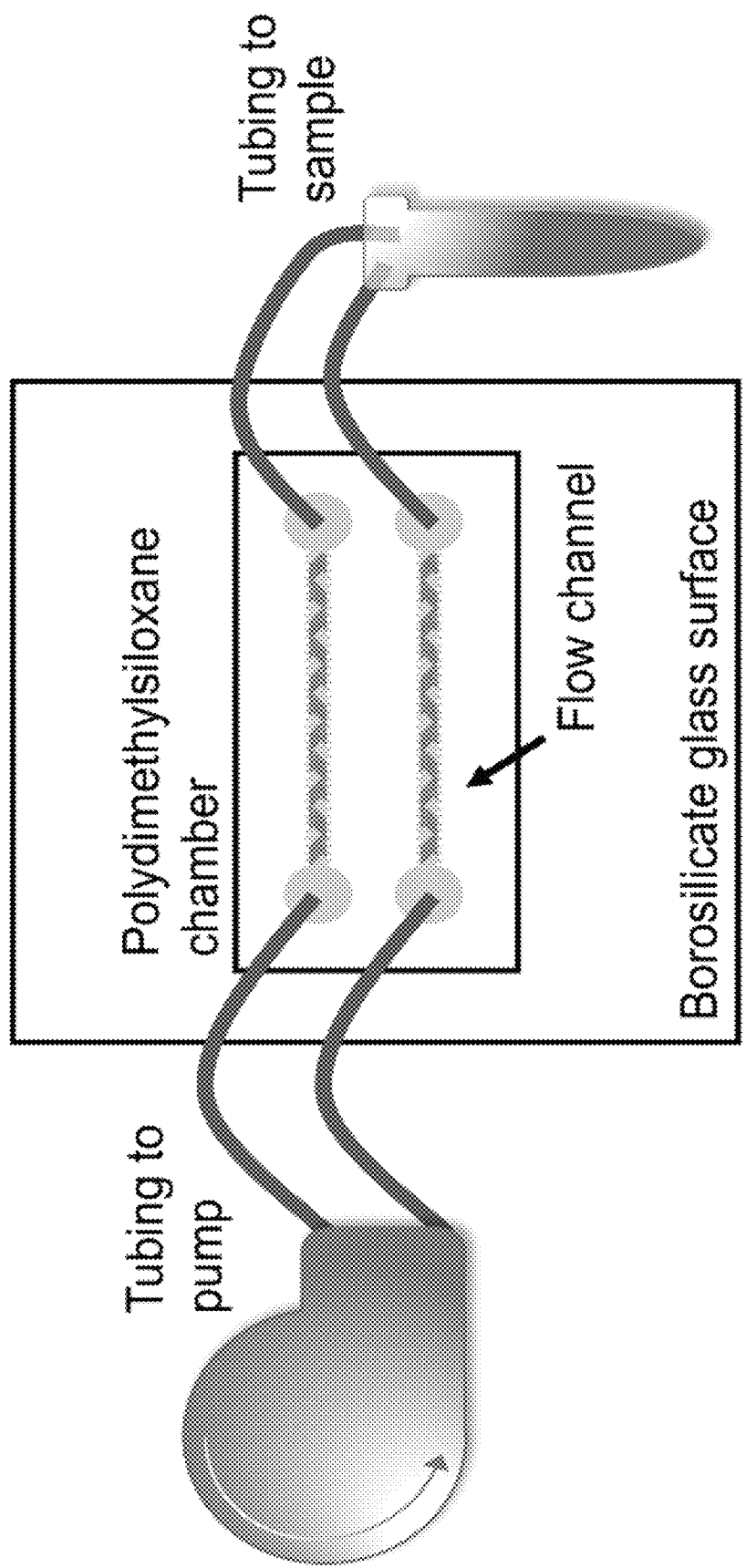
FIG. 24 Schematic diagram of SMAC chip connected to circulation system. The SMAC chip consists of a 22×22 mm borosilicate glass surface coated with high density PEG/biotin-PEG and then covalently attached to a polydimethylsiloxane chamber via our precision bonding technique (see below). The chamber is etched with flow channels that facilitate access of the clinical sample to the glass surface.

There are multiple potential configurations for the circulation system. This system is comprised of 3 basic interconnected parts: (1) sample, (2) SMAC chip, and (3) external pump to drive fluid flow. FIG. 24 illustrates a schematic diagram of one embodiment of a SMAC chip (top-down view) connected to a pump for fluid circulation and to a sample such as a biomaterial including blood, urine, saliva, or a combination thereof. The inner black rectangle delineates the boundaries of the microfluidic flow chamber (which is composed of the silicone elastomer polydimethylsiloxane (PDMS) in this example), while the outer black square delineates the boundaries of the capture surface (which is composed of borosilicate glass in this example). The microfluidic flow chamber may have 2 to over 1,000 flow channels though only two flow channels are depicted in FIG. 24.

The purpose of the pump is to constantly recycle the sample throughout the chip, and the pump may function via peristaltic, infusion/withdrawal, or pneumatic mechanisms, each of which results in different flow patterns within the chip. The choice of pump type is dictated in large part by specific application. For example, in the experience of the inventors a peristaltic pump is useful for experiments demanding very high sensitivity in non-complex sample matrices, such as PBS or Tris buffer. On the other hand, an infusion/withdrawal pump is useful for experiments in complex matrices such as human serum or plasma. Schematic diagrams of 2 potential configurations for the circulation system, with either a unidirectional pump or bidirectional pump, are shown in FIG. 30. A step-by-step procedure for setting up and operating the circulation system is provided below.

Procedure for Circulation System Setup

Note that the values for volume and concentration of all solutions mentioned below are provided for reference; these values are representative for typical SMAC experiments but may vary depending on the specific application and size of the SMAC chips. For circulation actuated by an infusion/withdrawal pump (bidirectional flow), SMAC chips conjugated with capture reagent are connected to a multi-channel infusion/withdrawal pump fitted with 26-gauge 1 cc syringes. Note that the needle sizes may vary depending on the tubing internal diameter. Chips are connected at the other tubing port to the sample prepared in T50-BSA or other suitable buffer. The sample may be any non-clinical or clinical fluid. Potential sources of clinical fluid include whole blood, plasma, serum, RBC fraction, urine, saliva, cerebrospinal fluid, semen, sweat, bile, gastric contents, breast milk, exudates, ascites, lymph, sputum, lavage fluid, and bronchial fluid. As discussed above, the presence of Tween-20 in the sample buffer is critical for preventing absorption of target proteins to the chamber walls due to the hydrophobic nature of PDMS, which would greatly diminish capture efficiency. Tween-20 may be included at varying concentration or substituted with other types of nonionic or ionic detergents (e.g., CHAPS, Triton X-100, NP40, Pluronic F-127, Brij 35). Depending on the specific application, other sample dilution buffer conditions may be adjusted, including the presence of additives (e.g., glycerol, ethylene glycol) and salt concentration. In general, the inventors have found that 50-150 mM salt concentration is an optimal range for capture of most target proteins, with a possible range of 0 mM to >1 M. For circulation, the pump is programmed to carry out repeated cycles of infusion/withdrawal at different flow rates (from 1 μl/min to >10 ml/min); circulation at 500 μl/min over a 2 hr period is preferred in most cases. In the most demanding cases, circulation may be performed for >24 hr for maximum SMAC sensitivity. Furthermore, depending on the intended application, flow rates may be adjusted. In general capture efficiency is improved with high velocity flow, due to increased chaotic mixing and antigen-Ab collisions at high flow rates (see FIG. 9). The circulation temperature may range from 4° C. to 37° C.; circulation at ambient temperature is preferred.

For circulation actuated by a peristaltic pump (unidirectional flow), multiple types of pump tubing material (e.g., silicone, polypropylene, C-Flex, Viton, Tygon, Norprene, Santoprene) are possible depending on the specific application. The inventors typically use platinum-cured silicone as the tubing material because of its low tendency for non-specific absorption of proteins. The peristaltic pump may be operated in a positive or negative pressure loop with a preferred flow rate of 800 μl/min for 2 hr at ambient temperature. Furthermore, the SMAC chips may be fabricated to different channel heights (in some cases from 1 μm to 2 mm). In general, circulation in chips with low channel heights yields improved capture efficiency compared to high channel heights. However, low channel heights may lead to low recovery of target proteins in a complex biologic matrix such as human serum or plasma. The potential variations (i.e. buffer conditions, flow rate, circulation time, and circulation temperature) for circulation via peristaltic pump are the same as that for circulation via infusion/withdrawal pump.

After the circulation period, chips are washed with T50-BSA buffer (1 ml) and incubated with fluorescence-labeled detection reagent (such as a fluorescence-labeled Ab) (10 μl, 1 nM) for 30 min. Note that 1 nM is a preferred detection reagent concentration; the actual concentration may range from 1 pM to 1 mM. Chips are then washed on pump with T50 buffer (1 ml) and subjected to downstream applications, such as single molecule TIRF microscopy.

TIRF Microscopy as a Single Molecule Detection Tool

The inventors have developed single molecule TIRF microscopy into a platform for non-invasive disease detection from clinical specimens or samples (e.g., whole blood, plasma, serum, RBC fraction, urine, saliva, cerebrospinal fluid, semen, sweat, bile, gastric contents, breast milk, exudates, ascites, lymph, sputum, lavage fluid, bronchial fluid). Based on the principle of TIRF, incident light of a specific wavelength generated from a laser source will undergo the phenomenon of 'total internal reflection' as it passes from the glass substrate of the SMAC chip towards the sample buffer if the light strikes the glass substrate at a large enough angle θ, where θ represents the angle between the incident light and a plane perpendicular to the glass surface. Consequently, the incident light will not enter into the sample buffer but rather produce an evanescent field of identical wavelength that penetrates ~100 nm into the sample buffer from the glass surface. Thus, only the capture surface itself (<0.05% of the channel height)—where complexes form between target molecule and fluorophore-labeled detection reagent—will be excited; the other >99.95% of the channel outside the capture surface will not be excited. Thus, any fluorophore-labeled detection reagent that remains as background in the channel is essentially invisible by TIRF imaging, allowing for extremely high signal-to-noise ratios. Furthermore, because the TIRF microscopy signal is collected by an electron multiplying charge coupled device camera with single photon sensitivity, even a single fluorophore-labeled target molecule can be visualized by TIRF imaging. Therefore, SMAC does not require any biochemical signal amplification steps, circumventing the background levels inherent in ELISA-based methods.

The inventors have built a fully computer-controlled TIRF microscopy system and programmed this system to streamline SMAC data acquisition. In this setup, the SMAC chip is placed on a motorized stage on the imaging apparatus, the capture surface is brought into focus, and SMAC micrographs are collected in a time stream for 500 frames with 50 ms exposure time under continuous excitation by a laser of defined wavelength (e.g., 405 nm, 488 nm, 561 nm, 647 nm). The laser power is typically set at 10 mW but may be adjusted (along with the number of acquisition frames and exposure time) depending on the specific application. A step-by-step procedure for operating our SMAC TIRF microscopy system is provided below.

Procedure for TIRF Microscopy of a SMAC Chip

The imaging system is first turned on, and the incident laser angle is adjusted to full TIRF mode with a prism. The inventors use an objective-based TIRF setup with a 60× or 100× objective of extremely high numerical aperature (>1.45) in order to achieve the proper incident light angle for full TIRF mode. The objective is cleaned with isopropanol and air dried. Low autofluorescence immersion oil is then applied to the objective, and the SMAC chip to be examined is placed on the motorized stage. The inventors use MetaMorph software to control the imaging system and manage data acquisition. The inventors have developed a program in MetaMorph to streamline the data acquisition process. First the laser is activated, and the capture surface is brought into focus. The flow channel in the SMAC chip is readily identified by the integrated side boxes, which delineate the boundaries of the channel. An imaging region of 150×150 pixels, which translates to a physical area of 25×25 μm, is then set. The size of this region corresponds to the approximate size of the laser spot. The imaging region may range from 1×1 to 1,500×1,500 pixels. Sample information is then entered into our MetaMorph program, and the program is initiated. The inventors have set the program to capture a time stream of 500 consecutive frames with 50 ms exposure time under a constant laser power of 10 mW. These parameters may vary according to the specific application. For example, the number of frames may range from 1 to 10,000; the exposure time may range from 10 ms to 500 ms; the laser power may range from 1 mW to 100 mW. After imaging each region, the program instructs the stage to move 50 μm down the length of the channel, and imaging is performed again as above. This process is carried out until 10 SMAC micrographs are taken per SMAC sample. The micrographs are saved automatically as TIFF file format, and data analysis is carried out with our SMAC algorithm as described below.

Digital Analysis Algorithm to Eliminate Background from the SMAC Assay

The inventors have developed a digital molecule counting algorithm that accurately discriminates between on-target and off-target detection based on threshold adjustment, thereby allowing them to reach signal-to-noise ratios approaching infinity (see FIG. 6). The threshold adjustment algorithm of the present invention capitalizes on the ability of polyclonal fluorophore-labeled detection antibodies (Ab) (or a mixture of monoclonal detection Ab) to form clusters of high fluorescence intensity around single cognate target proteins. By contrast, detection Ab that adhere to the surface through non-specific binding have an extremely low probability to form clusters and will have relatively low fluorescence. In fact, the inventors have estimated that, based on the xy resolution of our imaging system and the area per imaging field, the theoretical probability of non-specific detection Ab associating into clusters by chance on any particular field is ~1 in $4 \times 10^{13}$. The threshold adjustment algorithm of the present invention therefore functions by differentiating fluorescence spots that pass a certain fluorescence threshold (i.e. specific binding of detection Ab to target proteins) from spots that fail to pass this threshold (i.e. non-specific detection Ab binding).

In the algorithm of the present invention, a test is first applied to every pixel p in an imaging area of 150×150 pixels (25×25 μm physical size). Note that the imaging area could range from 1×1 to >1,500×1,500 pixels. The criteria for this test are that: (1) p has an intensity value that exceeds a defined threshold value, and (2) the intensity value of p exceeds the intensity value of all its 4-connected or 8-connected neighbors. For example, if p has coordinates of (x, y) in the imaging field, then its 4-connected neighbors include all 4 pixels with the coordinates (x±1, y) and (x, y±1); its 8-connected neighbors include all 8 pixels with the coordinates (x±1, y), (x, y±1), and (x±1, y±1). If p satisfies the criteria above, then it is chosen for further data processing; otherwise, p is excluded from further analysis.

The exact positions of fluorophore-labeled target molecules within each pixel p that passes the above test are then determined by analysis of its point spread function. The number of target molecules with unique positions is counted; molecules separated in the imaging field by a distance below a certain value (for example 1-50 nm) are assumed to be a single entity and hence are only counted once. Because in SMAC data acquisition is performed as a stream over 500 consecutive frames, target molecules may appear in 2 or more frames, which would cause the same molecules to be counted multiple times. To account for this, our algorithm merges molecules that have identical positions over all imaging frames. Thus, the final readout is the total number of unique fluorophore-labeled target molecules in each imaging field (displayed as 'counts per field').

The cutoff threshold is a critical parameter in SMAC analysis and must be set for each type of target molecule. The ideal threshold is influenced by a variety of parameters, including fluorophore brightness, fluorophore conjugation density of the detection reagent, and size of target molecule clusters. To determine the ideal threshold for a particular target molecule, a SMAC assay similar to that described in FIG. 6. should be performed with 2 groups: (1) a defined concentration of the target molecule in buffer (positive control), and (2) buffer only without the target molecule (negative control). The algorithm described above is applied to both control groups, and the number of counts per field in each control is determined over a range of different threshold intensities (for example, from 1,000 to 16,000). The number of counts per field in the positive control is divided by that in the negative control for each threshold value to compute the signal-to-noise ratio for that threshold value. The threshold that yields the highest signal-to-noise ratio is chosen for future SMAC analysis of the particular target molecule. This algorithm is so efficient in discriminating the presence of a true target molecule from off-target background that the signal-to-noise ratio becomes infinity once a certain threshold is reached (i.e. the negative control goes to 0 counts per field without substantial signal loss in the positive control). In these cases, the lowest threshold value that yields a signal-to-noise ratio of infinity should be chosen.

Alternatives to TIRF Microscopy Readout of the SMAC Chip

Although TIRF microscopy is an excellent technique for the digital analysis of a SMAC chip, other detection modalities are possible. In fact, the SMAC chip represents a universal device for the specific, efficient capture of target molecules of interest from a relatively large sample volume onto a miniscule surface, and these molecules could in principle be interrogated by any approach. For instance, SMAC may be used with traditional fluorescence microscopy methods. In this case, it may be preferred to first amplify the fluorescence signal, either through an enzymatic reaction or through introducing additional rounds of detection reagent (such as a fluorophore-labeled secondary Ab against the primary detection Ab). Alternatively, instead of a fluorescence-based approach, the detection reagent could be labeled with a different tag, such as a colorimetric, chemiluminescent, or radioactive tag, followed by signal readout with a technique suitable for the particular tag. Furthermore, SMAC may be used with label-free detection methods, such as those that involve electrical or magnetic detection modalities. Alternatively, target molecules of interest may be eluted from the SMAC chip and subjected to other downstream applications, such as mass spectrometry. The SMAC system may also be adapted to incorporate particles as part of the readout design, including quantum dots, microparticles, nanoparticles, and beads. Note that SMAC may also be employed for nucleic acid analysis, and as such, may be used with PCR-based methods, DNA/RNA hybridization probes, and DNA/RNA sequencing including next-generation sequencing. The various detection schemes mentioned above are not intended to be comprehensive but rather to provide some examples of other methods, in addition to TIRF microscopy, that could be used to extract information from a SMAC chip.

Broad Applications of SMAC Technology

SMAC may be used in either non-clinical or clinical applications. Non-clinical applications include any experiments performed in a laboratory setting which do not involve clinical specimens; experiments that involve pre-clinical specimens (such as those derived from common model organisms) fall under this category. Non-clinical applications include the detection of target molecules in a sample over a wide concentration range, from exceedingly rare molecules (down to 10-21 M) to abundant molecules (up to 10-3 M). Reasons to conduct SMAC in a non-clinical setting include but are not limited to the study of fundamental scientific problems that require a high degree of accuracy or sensitivity, the detection of certain molecules in the environment, the discovery/validation of new biomarkers or drugs, the development of new techniques and/or instruments (either related or unrelated to SMAC itself), or the development of new SMAC assays (either for future clinical translation or for other purposes).

Clinical applications of SMAC include any experiments which involve clinical specimens or samples. These specimens or samples may be from healthy human volunteers or patients with a variety of medical conditions. Subjects may be of any age, race, or gender. The specimens or samples could be taken from multiple areas of the body, such as whole blood, plasma, serum, RBC fraction, WBC fraction, urine, saliva, cerebrospinal fluid, semen, sweat, bile, gastric contents, breast milk, exudates, ascites, lymph, sputum, lavage fluid, bronchial fluid, or solid tissue biopsies. The volume of these samples could range from 0.5 µl to 1 ml, 1 ml to 10 ml, greater than 1 µl, or less than 1 L, as examples, with a preferred range of 10 µl to 10 ml. SMAC could be performed directly on these samples or after the samples have undergone processing. Possible processing steps include but are not limited to addition/removal of any substances, dilution, centrifugation, filtration, depletion, homogenization, fractionation, purification, and fixation. Clinical applications of SMAC include the detection of medical conditions, such as cancer, heart disease, stroke, lung disease, infection, metabolic disorders, autoimmune disorders, injury, neurologic disease, genetic disorders. The detection of these medical conditions could occur at any phase in their progression, from onset to advanced stage. In addition to detection of the above conditions, other applications of SMAC include their diagnosis, characterization, profiling, and monitoring at any stage of the disease. SMAC may be performed for simultaneous detection of a single target molecule (uniplex format), 2 target molecules (duplex format), or multiple target molecules (multiplex format).

Both non-clinical and clinical applications of SMAC may involve the detection of a variety of target molecule types. These include but are not limited to peptides, proteins, nucleic acids (DNA/RNA), lipids, carbohydrates, and small organic or non-organic compounds. SMAC may be used for the detection of combinations of the above substances, either in complex with each other or as part of a particle. The term particle here may refer to exosomes, microvesicles, apoptotic bodies, organelles, bacteria, and viruses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for making a chip for detecting of a target in a sample comprising:
   providing a microfluidic flow chamber comprising one or more flow channels comprising a capture surface and at least one micromixer
   providing a binding molecule, and
   binding the binding molecule to the capture surface by positioning an elastomer on top of the one or more flow channels and subjecting the capture surface to oxygen plasma for 1 to 300 seconds at an RF power in the range of 5-500 W at a pressure of 10 to 1,000 mtorr.

2. The method of claim 1 wherein the capture surface is composed of a material selected from the group comprising glass, silicon, PDMS, polystyrene, polycarbonate, polyvinylchloride, polymethyl methacrylate, a cyclic olefin polymer or a combination thereof.

3. The method of claim 1 wherein the binding molecule is a chemical conjugate.

4. The method of claim 3 wherein the chemical conjugate is a silane based compound.

5. The method of claim 4 wherein the silane based compound is a silane comprising one or more moieties selected from the group comprising an amino, a vinyl, an epoxy, an acryloxy, a methacryloxy, a styryl, an isocyanurate, an ureide, a sulfide, an isocyanate, a mercapto group, or a combination thereof.

6. The method of claim 3 wherein the chemical conjugate comprises:
   (a) one or more reactive groups selected from the group comprising succinimidyl valerate, N-hydroxysuccinimide ester, imidoester, epoxide, isothiocyanate, isocyanate, sulfonyl chloride, aldehyde, carbodiimide, acyl azide, anhydride, fluorobenzene, carbonate, fluorophenyl ester, or a combination thereof; and
   (b) one or more passivation groups with or without biotin modification selected from the group comprising polyethylene glycol, polyacrylamide, poly(acrylic acid), poly(N-hydroxyethyl acrylamide), poly(2-hydroxyethyl methacrylate), poly(2-methacryloyloxyethyl phosphorylcholine), poly(vinyl alcohol), poly(vinyl pyrrolidone), hydroxyethylcellulose, hydroxypropyl methylcellulose, dextran, hyaluronic acid, or a combination thereof.

7. The method of claim 4 wherein the silane based compound is conjugated to a chemical compound comprising:
   (a) one or more reactive groups selected from the group comprising succinimidyl valerate, N-hydroxysuccinimide ester, imidoester, epoxide, isothiocyanate, isocyanate, sulfonyl chloride, aldehyde, carbodiimide, acyl azide, anhydride, fluorobenzene, carbonate, fluorophenyl ester, or a combination thereof; and (b) one or more passivation groups with or without biotin modification selected from the group comprising polyethylene glycol, polyacrylamide, poly(acrylic acid), poly(N-hydroxyethyl acrylamide), poly(2-hydroxyethyl methacrylate), poly(2-methacryloyloxyethyl phosphorylcholine), poly(vinyl alcohol), poly(vinyl pyrrolidone), hydroxyethylcellulose, hydroxypropyl methylcellulose, dextran, hyaluronic acid, or a combination thereof.

8. The method of claim 3 wherein the binding molecule is covalently conjugated to the capture surface by the chemical conjugate.

9. The method of claim 1 wherein the binding molecule contains a first biotin binding complex selected from the group comprising biotin, avidin, NeutrAvidin, streptavidin, or a combination thereof.

10. The method of claim 9 wherein the chip further comprises a capture molecule that comprises a second biotin complex that is bound to the chip by the first biotin binding complex.

11. The method of claim 1 wherein the one or more micromixer is a passive micromixer selected from the group comprising embedded barriers, staggered herringbone grooves, intersecting channels, lamination, serpentine structure, slanted walls, walls with boxes, twisted channels, surface chemistry, zigzag channels or a combination thereof.

12. The method of claim 1 wherein the micromixer is an active micromixer selected from the group comprising acoustic, dielectophoretic, electrohydrodynamic force, electrokinetic instability, electrokinetic time-pulsed, magnetic, magneto-hydrodynamic force, pressure perturbation, thermal, or a combination thereof.

13. The method of claim 1 wherein the micromixer is a combination of a passive micromixer and an active micromixer.

14. The method of claim 1 wherein the microfluidic flow chamber comprises a material selected from the group comprising polydimethylsiloxane (PDMS), silicon, glass, polystyrene, polycarbonate, polyvinylchloride, polymethyl methacrylate, cyclic olefin copolymer, or a combination thereof.

15. The method of claim 1 wherein the one or more flow channels have a width in the range of 0.025 mm to 10 mm, a length in the range of 0.1 mm to 10 mm, and a height in the range of 0.001 mm to 2 mm.

* * * * *